(12) United States Patent
Brown et al.

(10) Patent No.: US 7,741,352 B2
(45) Date of Patent: Jun. 22, 2010

(54) KCNQ CHANNEL MODULATING COMPOUNDS AND THEIR PHARMACEUTICAL USE

(75) Inventors: William Dalby Brown, Ballerup (DK); Lene Teuber, Ballerup (DK); Bjarne H. Dahl, Ballerup (DK)

(73) Assignee: Neurosearch A/S, Ballerup (DK)

( * ) Notice: Subject to any disclaimer, the term of this patent is extended or adjusted under 35 U.S.C. 154(b) by 1307 days.

(21) Appl. No.: 10/546,533

(22) PCT Filed: Mar. 11, 2004

(86) PCT No.: PCT/EP2004/050290

§ 371 (c)(1),
(2), (4) Date: Aug. 22, 2005

(87) PCT Pub. No.: WO2004/080377

PCT Pub. Date: Sep. 23, 2004

(65) Prior Publication Data

US 2006/0173058 A1   Aug. 3, 2006

(30) Foreign Application Priority Data

Mar. 11, 2003   (DK) ............................. 2003 00370

(51) Int. Cl.
| | | |
|---|---|---|
| A61K 31/41 | (2006.01) | |
| A61K 31/19 | (2006.01) | |
| A61K 31/275 | (2006.01) | |
| A61K 31/165 | (2006.01) | |
| C07C 255/03 | (2006.01) | |
| C07C 65/01 | (2006.01) | |
| C07C 233/01 | (2006.01) | |
| C07D 257/02 | (2006.01) | |

(52) U.S. Cl. ...................... 514/381; 514/520; 514/568; 514/621; 514/640; 558/411; 548/252; 562/475; 564/123

(58) Field of Classification Search ................. 514/381, 514/568, 520, 621, 640; 558/411; 548/252; 562/475; 564/123
See application file for complete search history.

(56) References Cited

U.S. PATENT DOCUMENTS

| 2,852,557 | A | | 9/1958 | Schraufstatter | |
|---|---|---|---|---|---|
| 5,610,156 | A | * | 3/1997 | Albright et al. | ............. 514/220 |
| 5,700,796 | A | * | 12/1997 | Albright et al. | ............. 514/220 |
| 5,753,648 | A | | 5/1998 | Albright et al. | |

FOREIGN PATENT DOCUMENTS

| DE | 2 232 462 A | 1/1974 |
|---|---|---|
| WO | WO-96/03380 A | 2/1996 |
| WO | WO-01/10380 A | 2/2001 |
| WO | WO-02/062295 A | 8/2002 |

OTHER PUBLICATIONS

Sugiyama et al., Database Chemabs, Chemical Abstracts Service, Columbus, Ohio, Database Accession No. 1992:612486 & JP 04/154773; Green Cross Corp; May 27, 1992.

Database Beilstein, Beilstein Institute for Organic Chemistrym Frankfurt-Main, Germany; Database Accession No. BRN 4865050 & Naito et al., Chem. Pharm. Bull., vol. 39, No. 7, 1991, pp. 1736-1745.

Database Beilstein, Beilstein Institute for Organic Chemistry, Frankfurt-Main, Germany; Database Accession No. BRN2653068 & Kametani: Yakugaku Zasshi, vol. 72, 1952, pp. 1081-1083.

Database Beilstein, Beilstein Institute for Organic Chemistry, Frankfurt-Main, Germany, Database Accession No. BRN 8724243 & Marriot et al.: Chem Soc. perkin Trans, vol. 1, No. 24, 2000, pp. 4265-4278.

Database Beilstein, Beilstein Institute for Organic Chemistry, Frankfurt-Main, Germany, Database Accession No. BRN 2652765 & Berdaque et al., Bull. Chim. Soc. FR., vol. 130, 1993, pp. 475-480.

Database Beilstein, Beilstein Institute for Organic Chemistry, Frankfurt-Main, Germany, Database Accession No. BRN 5869057 & Binnemans et al.: J. Amer. Chem. Soc., vol. 122, No. 18, 2000, pp. 4335-4344.

Database Beilstein, Beilstein Institute for Organic Chemistry, Frankfurt-Main, Germany, Database Accession No. BRN 5869062 & Mikhaleva et al., Chem. Heterocycl. Compd, vol. 28, No. 3, 1992, pp. 316-320.

Database Beilstein, Beilstein Institute for Organic Chemistry, Frankfurt-Main, Germany, Database Accession No. BRN 3318003 & Nodzu et al.: Yakugaku Zasshi, vol. 79, 1959, p. 1378.

Database Beilstein, Beilstein Institute for Organic Chemistry, Frankfurt-Main, Germany, Database Accession No. BRN 1104542 & Yamamoto et al.: Chem. Pharm. Bull., vol. 44, No. 4, 1996, pp. 734-745.

Database Beilstein, Beilstein Institute for Organic Chemistry, Frankfurt-Main, Germany, Database Accession No. BRN 1825682 & Rose et al.: J. Americ. Chem. Soc., vol. 93, 1971, p. 4350, 4352 and 4353.

Database Beilstein, Beilstein Institute for Organic Chemistry, Frankfurt-Main, Germany, Database Accession No. BRN 208772 & Klosa: Arch. Pharm. vol. 289, 1956, pp. 196-199.

Database Beilstein, Beilstein Institute for Organic Chemistry, Frankfurt-Main, Germany, Database Accession No. BRN 2865481 & Walker et al.: J. Med. Chem., vol. 9, 1966, pp. 624-630.

Database Beilstein, Beilstein Institute for Organic Chemistry, Frankfurt-Main, Germany, Database Accession No. Reaction ID 4725290 & Astles et al.: Eur. J. Med. Chem. Chi., vol. 32, No. 5, 1997, pp. 409-424.

(Continued)

*Primary Examiner*—James O Wilson
*Assistant Examiner*—Ebenezer Sackey
(74) *Attorney, Agent, or Firm*—Birch, Stewart, Kolasch & Birch, LLP.

(57) ABSTRACT

This invention relates to novel compounds useful as modulators of the KCNQ channel, to pharmaceutical compositions comprising these compounds, and to methods of treatment herewith.

8 Claims, No Drawings

OTHER PUBLICATIONS

Database Beilstein, Beilstein Institute for Organic Chemistry, Frankfurt-Main, Germany, Database Accession No. BRN 5033009 & Tighineanu et al.: Tetrahedron, vol. 36, 1980, pp. 1385-1397.

Database Beilstein, Beilstein Institute for Organic Chemistry, Frankfurt-Main, Germany, Database Accession No. BRN 37756 & Shirley: J. Americ. Chem. Soc. vol. 74, 1952, p. 664.

Database Beilstein, Beilstein Institute for Organic Chemistry, Frankfurt-Main, Germany, Database Accession No. BRN 6983888 & Marcos et al.: J. Chem. Soc. Chem. Commun., vol. 21, 1989, pp. 1641-1643.

Database Beilstein, Beilstein Institute for Organic Chemistry, Frankfurt-Main, Germany, Database Accession No. BRN 3404241 & Purrello: Boll. Sedute Accad. Gioenia Sci. Nat. Catania, vol. 4, No. 3, 1957, pp. 446-450.

Database Beilstein, Beilstein Institute for Organic Chemistry, Frankfurt-Main, Germany, Database Accession No. BRN 2096811 & Kostanecki et al.: Chem. Ber, vol. 28, 1985, pp. 2302-2309.

Database Beilstein, Beilstein Institute for Organic Chemistry, Frankfurt-Main, Germany, Database Accession No. BRN 8482080 & Nishioka et al.: Synthesis, vol. 2, 2000, pp. 243-246.

Wang, Q. et al., Nature Genetics; vol. 12, pp. 17-13 (Jan. 1996).

Biervert, Christian et al., Science, vol. 279, pp. 403-406 (Jan. 1998).

Schroeder, B. C. et al.; Nature, vol. 396, pp. 687-690 (Dec. 1998).

Kubisch, Christian et al.; Cell, vol. 96, pp. 437-446 (Feb. 1999).

Schroeder, B.C. et al.; The Journal of Biological Chemistry, vol. 275, No. 31, pp. 24080-24095 (2000).

XP-002292398, Green Cross Corp.; JP 04154773 published May 27, 1992; Category: X.

Naito, Y. et al.; Chem. Pharm. Bull., vol. 39, No. 7, pp. 1736-1745 (1991).

Kametani, T. et al.; Synthesis of Isoquinoline Derivatives; Yakugaku Zasshi, vol. 72; pp. 1081-1083 (1952).

Marriott, Jonathan H. et al.; J. Chem. Soc.; Perkin Trans. 1, pp. 4265-4278 (2000).

Berdague, P. et al.; Bull. Soc. Chim. Fr.; vol. 130; pp. 475-480 (1993).

Binnemans, Koen et al.; J. Am. Chem. Soc.; vol. 122, pp. 4335-4344 (2000).

* cited by examiner

KCNQ CHANNEL MODULATING COMPOUNDS AND THEIR PHARMACEUTICAL USE

TECHNICAL FIELD

This invention relates to novel compounds useful as modulators of the KCNQ channel, to pharmaceutical compositions comprising these compounds, and to methods of treatment herewith.

BACKGROUND ART

Potassium ($K^+$) channels are structurally and functionally diverse families of $K^+$-selective channel proteins, which are ubiquitous in cells, indicating their central importance in regulating a number of key cell functions. While widely distributed as a class, $K^+$ channels are differentially distributed as individual members of this class or as families.

Recently a new family of potassium channels, the KCNQ channels, has attracted attention as target for therapeutic development. The human KCNQ1 channel was disclosed by Wang, Q et al. [Wang, Q et al.; *Nature Genet.* 1996 12 17-23], the human KCNQ2 channel was disclosed by Biervert et al. [Biervert et al.; *Science* 1998 279 403-406]; the human KCNQ3 channel was disclosed by Schroeder et al. [Schroeder et al.; *Nature* 1998 396 687-690]; the human KCNQ4 channel was disclosed by Kubisch et al. [Kubisch et al; *Cell* 1999 96 (3) 43746]; and the human KCNQ5 channel was disclosed by Schroeder et al. [Schroeder et al.; *J. Biol. Chem.* 2000 275 (31) 24089-24095].

Due to the distribution of KCNQ channels within the organism, KCNQ channel modulators are considered potentially useful for the treatment or alleviation of conditions as diverse as pain, migraine, tension type headache, CNS disorders, CNS damage caused by trauma, stroke or neurodegenerative illness or diseases, learning and cognitive disorders, motion and motor disorders, multiple sclerosis, heart failure, cardiomyopathia, cardiac disorders, inflammatory diseases, ophthalmic conditions, progressive hearing loss or tinnitus, obstructive or inflammatory airway diseases, for inducing or maintaining bladder control including the treatment or prevention of urinary incontinence.

SUMMARY OF THE INVENTION

It is an object of the invention to provide novel compounds useful as modulators of the KCNQ channels. Accordingly, in its first aspect, the invention provides compounds represented by Formula I

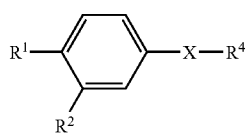

(I)

any of its enantiomers or any mixture of its enantiomers, or a prodrug, or a pharmaceutically-acceptable addition salt thereof, wherein $R^1$ represents —OH, —CN, —(CO)OH, —CO—R', —(CO)NH—R', —(CO)NH—NHR', —CHNO—R'; —NH(CO)—R', —(SO$_2$)NH—R', —NH(SO$_2$)—R', a tetrazolyl group, an oxadiazolyl group or an oxathiadiazolyl group; wherein R' represents hydrogen, alkyl, cycloalkyl, cycloalkyl-alkyl, alkyl-cycloalkyl, alkyl-cycloalkyl-alkyl, haloalkyl;

$R^2$ represents halo, haloalkyl, hydroxy, alkoxy, cycloalkoxy, cycloalkyl-alkoxy, phenoxy, phenyl-alkoxy, amino, nitro or cyano;

X represents O, OCH$_2$, OCH$_2$CH$_2$, O(CO), CO, (CO)O, NR", NR"CH$_2$, NR"(CO), (CO)NR", N═CH, CH═N, N═N, S, (SO$_2$)NR" or NR"(SO$_2$) (read in the stated direction); wherein R" represents hydrogen, alkyl or cycloalkyl;

$R^4$ represents alkyl, cycloalkyl, cycloalkyl-alkyl, alkoxy-alkyl, cycloalkoxy-alkyl, cycloalkoxy-cycloalkyl, cycloalkoxy-cycloalkoxy, alkoxy-alkoxy, alkoxy-alkoxy-alkyl, cycloalkoxy-alkoxy-alkyl, carboxy-alkyl, alkyl-carbonyl-alkyl, alkenyl, alkenyl-alkenyl, carboxy-alkenyl, alkyl-carbonyl-alkenyl, alkynyl, hydroxy-alkyl or dihydroxy-alkyl; or $R^4$ represents aryl, aryl-alkyl, heteroaryl or heteroaryl-alkyl, which aryl or heteroaryl groups may be mono-, bi- or poly-cyclic, and which aryl or heteroaryl groups may optionally be substituted one or more times with substituents selected from the group consisting of halo, alkyl, haloalkyl, cycloalkyl, cycloalkyl-alkyl, hydroxy, alkoxy, haloalkoxy, cycloalkoxy, hydroxyalkyl, alkoxy-alkyl, alkenyl, alkenyloxy, alkynyl, hydroxyalkynyl, nitro, amino, N-alkyl-amino, N,N-dialkyl-amino, cyano, carboxy, alkyl-carbonyl, alkyloxalyl, alkoxyoxalyl, alkyloxalyl-amino, alkoxyoxalyl-amino, alkoxy-carbonyl, carbamoyl, N-alkyl-carbamoyl, N-(alkyl-carbonyl)amino, N,N-di(alkyl-carbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, propylenedioxy, aryl, aryloxy, aralkyl and aralkyloxy; or $R^4$ represents a group of formula Y or -L'-Y; wherein Y represents a non-aromatic heterocyclic group, which heterocyclic group may optionally be substituted once or twice with substituents selected from the group consisting of alkyl, cycloalkyl and cycloalkyl-alkyl; and L' represents alkyl or alkenyl; or $R^4$ represents a group of formula -Z'-L"-Z"; wherein Z' and Z", independently of one another, represent a mono-, bi- or poly-cyclic aryl or heteroaryl group, which aryl or heteroaryl group may optionally be substituted one or more times with substituents selected from halo, alkyl, haloalkyl, cycloalkyl, cycloalkyl-alkyl, hydroxy, alkoxy, haloalkoxy, cycloalkoxy, hydroxyalkyl, alkoxy-alkyl, alkenyloxy, alkynyl, hydroxyalkynyl, nitro, amino, N-alkyl-amino, N,N-dialkyl-amino, cyano, carboxy, alkyl-carbonyl, alkyloxalyl, alkoxyoxalyl, alkyloxalyl-amino, alkoxyoxalyl-amino, alkoxy-carbonyl, carbonyl, N-alkyl-carbamoyl, N-(alkyl-carbonyl)amino, N,N-di(alkyl-carbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, propylenedioxy, phenyl, phenyloxy, benzyl and benzyloxy; and L" represents a single (covalent) bond, or a linker selected from alkyl, O, OCH$_2$, S, SCH$_2$, (CO), (CO)CH$_2$, NH, NHCH$_2$, (SO$_2$)NH, NH(SO$_2$), pyrrolidinyl and piperidinyl.

In another aspect the invention provides pharmaceutical compositions comprising a therapeutically effective amount of a compound of the invention, or a pharmaceutically-acceptable addition salt thereof.

Viewed from another aspect the invention relates to the use of a compound of the invention, or a pharmaceutically-acceptable addition salt thereof, for the manufacture of a pharmaceutical composition.

Finally the invention provides a method of treatment, prevention or alleviation of a disease or a disorder or a condition of a living animal body, including a human, which disorder, disease or condition is responsive to modulation of a KCNQ potassium channel, which method comprises the step of administering to such a living animal body in need thereof, a therapeutically effective amount of the compound of the invention.

Other objects of the invention will be apparent to the person skilled in the art from the following detailed description and examples.

DETAILED DISCLOSURE OF THE INVENTION

In its first aspect the invention provides a compound represented by Formula I

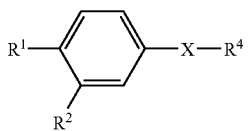

(I)

any of its enantiomers or any mixture of its enantiomers, a prodrug or a pharmaceutically-acceptable addition salt thereof, wherein $R^1$ represents —OH, —CN, —(CO)OH, —CO—R', —(CO)NH—R', —(CO)NH—NHR', —CHNO—R'; —NH(CO)—R', —(SO$_2$)NH—R', —NH(SO$_2$)—R', a tetrazolyl group, an oxadiazolyl group or an oxathiadiazolyl group, which heterocyclic groups may optionally be substituted with oxo and/or alkyl; wherein R' represents hydrogen, alkyl, cycloalkyl, cycloalkyl-alkyl, alkyl-cycloalkyl, alkyl-cycloalkyl-alkyl, haloalkyl;

$R^2$ represents halo, haloalkyl, hydroxy, alkoxy, cycloalkoxy, cycloalkyl-alkoxy, phenoxy, phenyl-alkoxy, amino, nitro or cyano;

X represents O, OCH$_2$, OCH$_2$CH$_2$, O(CO), CO, (CO)O, NR", NR"CH$_2$, NR"(CO), (CO)NR", N=CH, CH=N, N=N, S, (SO$_2$)NR" or NR"(SO$_2$) (read in the stated direction); wherein R" represents hydrogen, alkyl or cycloalkyl;

$R^4$ represents alkyl, cycloalkyl, cycloalkyl-alkyl, alkoxy-alkyl, cycloalkoxy-alkyl, cycloalkoxy-cycloalkyl, cycloalkoxy-cycloalkoxy, alkoxy-alkoxy, alkoxy-alkoxy-alkyl, cycloalkoxy-alkoxy-alkyl, carboxy-alkyl, alkylcarbonyl-alkyl, alkenyl, alkenyl-alkenyl, carboxy-alkenyl, alkyl-carbonyl-alkenyl, alkynyl, hydroxy-alkyl or dihydroxy-alkyl; or $R^4$ represents aryl, aryl-alkyl, heteroaryl or heteroaryl-alkyl, which aryl or heteroaryl groups may be mono-, bi- or poly-cyclic, and which aryl or heteroaryl groups may optionally be substituted one or more times with substituents selected from the group consisting of halo, alkyl, haloalkyl, cycloalkyl, cycloalkyl-alkyl, hydroxy, alkoxy, haloalkoxy, cycloalkoxy, hydroxyalkyl, alkoxy-alkyl, alkenyl, alkenyloxy, alkynyl, hydroxyalkynyl, nitro, amino, N-alkyl-amino, N,N-dialkyl-amino, cyano, carboxy, alkylcarbonyl, alkyloxalyl, alkoxyoxalyl, alkyloxalyl-amino, alkoxyoxalyl-amino, alkoxy-carbonyl, carbamoyl, N-alkyl-carbamoyl, N-(alkyl-carbonyl)amino, N,N-di(alkylcarbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, propylenedioxy, aryl, aryloxy, aralkyl and aralkyloxy; or $R^4$ represents a group of formula Y or -L'-Y; wherein Y represents a non-aromatic heterocyclic group, which heterocyclic group may optionally be substituted once or twice with substituents selected from the group consisting of alkyl, cycloalkyl and cycloalkyl-alkyl; and L' represents alkyl or alkenyl; or $R^4$ represents a group of formula -Z'-L"-Z"; wherein Z' and Z", independently of one another, represent a mono-, bi- or poly-cyclic aryl or heteroaryl group, which aryl or heteroaryl group may optionally be substituted one or more times with substituents selected from halo, alkyl, haloalkyl, cycloalkyl, cycloalkyl-alkyl, hydroxy, alkoxy, haloalkoxy, cycloalkoxy, hydroxyalkyl, alkoxy-alkyl, alkenyloxy, alkynyl, hydroxyalkynyl, nitro, amino, N-alkyl-amino, N,N-dialkyl-amino, cyano, carboxy, alkylcarbonyl, alkyloxalyl, alkoxyoxalyl, alkyloxalyl-amino, alkoxyoxalyl-amino, alkoxy-carbonyl, carbamoyl, N-alkyl-carbamoyl, N-(alkyl-carbonyl)amino, N,N-di(alkylcarbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, propylenedioxy, phenyl, phenyloxy, benzyl and benzyloxy; and L" represents a single (covalent) bond, or a linker selected from alkyl, O, OCH$_2$, S, SCH$_2$, (CO), (CO)CH$_2$, NH, NHCH$_2$, (SO$_2$)NH, NH(SO$_2$), pyrrolidinyl and piperidinyl.

In a preferred embodiment the compound of the invention is a compound of Formula I, wherein $R^1$ represents —OH, —CN, —(CO)OH, —CO—R', —(CO)NH—R', —CHNO—R'; —NH(CO)—R', —(SO$_2$)NH—R', —NH(SO$_2$)R', a tetrazolyl group, [1,2,4]-oxadiazol-5-on-3-yl, 5-methyl-2,5-dihydro-[1,2,4]-oxadiazol-3-yl or [1,2,3,5]-oxathiadiazol-2-oxide-4-yl; wherein R' represents hydrogen, alkyl, cycloalkyl, cycloalkyl-alkyl, alkyl-cycloalkyl, alkyl-cycloalkyl-alkyl or haloalkyl.

In a more preferred embodiment $R^1$ represents —OH, —CN, —(CO)OH, —CO-alkyl, —(CO)NH$_2$, —(CO)NH-alkyl, CHNOH; —NH(CO)-haloalkyl, —NH(SO$_2$)alkyl, 1H-tetrazolyl, [1,2,4]-oxadiazol-5-on-3-yl, 5-methyl-2,5-dihydro-[1,2,4]-oxadiazol-3-yl or [1,2,3,5]-oxathiadiazol-2-oxide-4-yl.

In another preferred embodiment the compound of the invention is a compound of Formula I, wherein $R^2$ represents halo, haloalkyl, hydroxy, alkoxy, cycloalkoxy, cycloalkyl-alkoxy, phenoxy, phenyl-alkoxy, amino, nitro or cyano.

In a more preferred embodiment $R^2$ represents halo, CF$_3$, hydroxy, alkoxy, phenyl-alkoxy, amino, nitro or cyano.

In a third preferred embodiment the compound of the invention is a compound of Formula I, wherein X represents O, OCH$_2$, OCH$_2$CH$_2$, O(CO), CO, (CO)O, NH, NHCH$_2$, N(CH$_3$), N(CH$_3$)CH$_2$, NH(CO), (CO)NH, N=CH, CH=N, N=N, S, (SO$_2$)NH or NH(SO$_2$) (read in the stated direction)

In a more preferred embodiment X represents O, OCH$_2$, O(CO), (CO)O, NH, NHCH$_2$, NH(CO), (CO)NH, N=CH, N=N or (SO$_2$)NH (read in the stated direction).

In an even more preferred embodiment X represents O, OCH$_2$, O(CO), NH, NHCH$_2$, N(CH$_3$), N(CH$_3$)CH$_2$, NH(CO) or N=N (read in the stated direction).

In a fourth preferred embodiment the compound of the invention is a compound of Formula I, wherein $R^4$ represents alkyl, cycloalkyl, cycloalkyl-alkyl, alkoxy-alkyl, cycloalkoxy-alkyl, cycloalkoxy-cycloalkyl, cycloalkoxy-cycloalkoxy, alkoxy-alkoxy, alkoxy-alkoxy-alkyl, cycloalkoxy-alkoxy-alkyl, carboxy-alkyl, alkyl-carbonyl-alkyl, alkenyl, alkenyl-alkenyl, carboxy-alkenyl, alkyl-carbonyl-alkenyl, alkynyl, hydroxy-alkyl, dihydroxy-alkyl.

In a more preferred embodiment $R^4$ represents alkyl, cycloalkyl, cycloalkyl-alkyl, alkoxy-alkyl, alkoxy-alkoxy, alkoxy-alkoxy-alkyl, cycloalkoxy-alkoxy-alkyl, carboxy-alkyl, alkyl-carbonyl-alkyl, alkenyl, alkenyl-alkenyl, carboxy-alkenyl, alkyl-carbonyl-alkenyl, alkynyl, hydroxy-alkyl or dihydroxy-alkyl.

In an even more preferred embodiment $R^4$ represents methyl, ethyl, propyl, butyl, pentyl, hexyl, heptyl, octyl, nonyl, methoxy-ethyl, methoxy-ethoxy-ethyl, butenyl, pentenyl, hexenyl, heptenyl, octenyl, nonenyl, octa-2,6-dienyl, 3,7-dimethyl-octa-2,6-dienyl, hydroxyhexyl, hydroxyoctyl, 2,3-dihydroxypropyl, 3,4-dihydroxybutyl, 5,6-dihydroxy-hexyl, 7,8-dihydroxyoctyl, 7,7-dihydroxy-3,6-dimethyl-octyl, —(CO)OH, carboxymethoxy or acryloyl.

In a most preferred embodiment the compound of the invention is
4-Octyloxy-benzene-1,2-diol;
2-Hydroxy-4-octyloxy-benzaldehyde;
1-(2-Hydroxy-4-octyloxy-phenyl)-ethanone;
4-(3-Carboxy-acryloylamino)-2-hydroxy-benzoic acid;
4-Carboxymethoxy-2-hydroxy-benzoic acid;
4-[(Biphenyl-4-carbonyl)-amino]-2-methoxy-benzoic acid;
4-[(Biphenyl-4-carbonyl)amino]-2-hydroxy-benzoic acid;
2-Hydroxy-4-octyloxy-benzoic acid;
2-Hydroxy-4-octyloxy-benzoic acid;
2-Hydroxy-4-octyloxy-benzamide;
2-Hydroxy-4-octyloxy-benzaldehyde oxime;
2-Hydroxy-4-octyloxy-benzonitrile;
2,2,2-Trifluoro-N-(2-hydroxy-4-octyloxy-phenyl)-acetamide;
N-(2-Hydroxy-4-octyloxy-phenyl)-methanesulfonamide;
4-(3,4-Dihydroxybutoxy)-2-hydroxy-benzoic acid;
4-Hex-5-enyloxy-2-hydroxy-benzoic acid;
4-(5,6-Dihydroxhexoxy)-2-hydroxy-benzoic acid;
2-Hydroxy-4-oct-7-enyloxy-benzoic acid;
4-(3,7-Dimethyl-octa-2,6-dienyloxy)-2-hydroxybenzoic acid;
2-Hydroxy-4-(6-hydroxyhexyloxy) benzoic acid;
2-Hydroxy-4-(2-methoxy-ethoxy)-benzoic acid;
4-(7,8-Dihydroxyoctyloxy-2-hydroxy-benzoic acid;
4-(2,3-Dihydroxypropoxy)-2-hydroxy-benzoic acid;
2-Hydroxy-4-(8-hydroxy-octyloxy) benzoic acid;
2-Chloro-4-oct-7-enyloxy-benzoic acid;
2-Chloro-4-(7,8-dihydroxy-octyloxy) benzoic acid;
4-(7,7-Dihydroxy-3,6-dimethyl-octyloxy)-2-hydroxy benzoic acid;
2-Fluoro-4-oct-7-enyloxy-benzoic acid;
2-Hydroxy-4-[2-(2-methoxy-ethoxy)-ethoxy]-benzoic acid;
4-But-3-enyloxy-2-hydroxy-benzoic acid;
2-Fluoro-4-(7,8-dihydroxy-octyloxy) benzoic acid; or
5-Octyloxy-2-(1H-tetrazol-5-yl)-phenol;
or a pharmaceutically-acceptable addition salt thereof.

In a fifth preferred embodiment the compound of the invention is a compound of Formula I, wherein $R^4$ represents aryl, aryl-alkyl, heteroaryl or heteroaryl-alkyl, which aryl or heteroaryl groups may be mono-, bi- or poly-cyclic, and which aryl or heteroaryl groups may optionally be substituted one or more times with substituents selected from the group consisting of halo, alkyl, haloalkyl, cycloalkyl, cycloalkyl-alkyl, hydroxy, alkoxy, haloalkoxy, cycloalkoxy, hydroxyalkyl, alkoxy-alkyl, alkenyloxy, alkynyl, hydroxyalkynyl, nitro, amino, N-alkyl-amino, N,N-dialkyl-amino, cyano, carboxy, alkyl-carbonyl, alkyloxalyl, alkoxyoxalyl, alkyloxalyl-amino, alkoxyoxalyl-amino, alkoxy-carbonyl, carbamoyl, N-alkyl-carbamoyl, N-(alkyl-carbonyl)amino, N,N-di(alkyl-carbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, propylenedioxy, aryl, aryloxy, aralkyl or aralkyloxy.

In a more preferred embodiment $R^4$ represents aryl, aryl-alkyl, heteroaryl or heteroaryl-alkyl, which aryl or heteroaryl groups may optionally be substituted one or two times with substituents selected from the group consisting of halo, alkyl, haloalkyl, cycloalkyl, cycloalkyl-alkyl, hydroxy, alkoxy, haloalkoxy, hydroxyalkynyl, nitro, amino, cyano, carboxy, N-alkyl-carbamoyl, N-(alkyl-carbonyl)amino, N,N-di(alkyl-carbonyl)amino, alkoxyoxalyl-amino, sulfamoyl, N-alkyl-sulfamoyl, N,N-dialkyl-sulfamoyl, methylenedioxy, ethylenedioxy, propylenedioxy, phenyl, phenoxy, benzyl or benzyloxy.

In an even more preferred embodiment $R^4$ represents phenyl; benzyl; naphthyl; furanyl, in particular 2- or 3-furanyl; thienyl, in particular 2-thienyl; pyridinyl, in particular 2-, 3- or 4-pyridinyl; isoxazolyl, in particular 3-, 4- or 5-isoxazolyl; pyrazolyl, in particular 1-, 3- or 4-pyrazolyl; in particular [1,2,3]triazolyl or [1,2,4]triazolyl; benzo[b]furanyl, in particular 2-, 5- or 6-benzofuranyl; benzo[b]thienyl, in particular 2-, 5- or 6-benzothienyl; benzimidazolyl, in particular 2-, 5- or 6-benzoimidazolyl; quinolinyl, in particular 2-, 3-, 6- or 7-quinolinyl; isoquinolinyl, in particular 3-, 6- or 7-isoquinolinyl; or cinnolinyl, in particular 6- or 7-cinnolinyl; which aryl or heteroaryl groups may optionally be substituted one or two times with substituents selected from the group consisting of halo, alkyl, haloalkyl, cycloalkyl, cycloalkyl-alkyl, hydroxy, alkoxy, haloalkoxy, cycloalkoxy, hydroxyalkyl, alkoxy-alkyl, alkenyloxy, alkynyl, hydroxyalkynyl, nitro, amino, N-alkyl-amino, N,N-dialkyl-amino, cyano, carboxy, alkyl-carbonyl, alkyloxalyl, alkoxyoxalyl, alkyloxalyl-amino, alkoxyoxalyl-amino, alkoxy-carbonyl, carbamoyl, N-alkyl-carbamoyl, N-(alkyl-carbonyl)amino, N,N-di(alkyl-carbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, propylenedioxy, aryl, aryloxy, aralkyl and aralkyloxy.

In a yet more preferred embodiment $R^4$ represents phenyl; benzyl; naphthyl; furanyl, in particular 2- or 3-furanyl; thienyl, in particular 2-thienyl; pyridinyl, in particular 2-, 3- or 4-pyridinyl; isoxazolyl, in particular 3-, 4- or 5-isoxazolyl; pyrazolyl, in particular 1-, 3- or 4-pyrazolyl; in particular [1,2,3]triazolyl or [1,2,4]triazolyl; benzo[b]furanyl, in particular 2-, 5- or 6-benzofuranyl; benzo[b]thienyl, in particular 2-, 5- or 6-benzothienyl; benzimidazolyl, in particular 2-, 5- or 6-benzoimidazolyl; quinolinyl, in particular 2-, 3-, 6- or 7-quinolinyl; isoquinolinyl, in particular 3-, 6- or 7-isoquinolinyl; or cinnolinyl, in particular 6- or 7-cinnolinyl; which aryl or heteroaryl groups may optionally be substituted one or two times with substituents selected from the group consisting of halo, alkyl, haloalkyl, hydroxy, alkoxy, haloalkoxy, hydroxyalkynyl, nitro, amino, cyano, carboxy, alkyloxalyl, alkoxyoxalyl, alkyloxalyl-amino, alkoxyoxalyl-amino, alkoxy-carbonyl, carbamoyl, N-alkyl-carbamoyl, N-(alkyl-carbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, propylenedioxy, phenyl, phenyloxy, benzyl and benzyloxy.

In a still more preferred embodiment $R^4$ represents phenyl, 2-nitro-phenyl, 3-nitro-phenyl, 4-nitro-phenyl, 2-allyloxy-phenyl, 3-bromo-phenyl, 4-bromo-phenyl, 3-hydroxy-phenyl, 3-methoxy-phenyl, 3-carboxy-phenyl, 3-amino-phenyl, 4-amino-phenyl, 2-cyano-phenyl, 3-(N-acetylamino)phenyl, 3,4-dimethoxy-phenyl, 3,4-methylenedioxy-phenyl, 4-difluoromethoxy-phenyl, 4-hydroxymethyl-phenyl, 4-carboxy-phenyl, 4-acetylamino-phenyl, 4-fluorophenyl, 4-(ethoxyoxalyl-amino)-phenyl, benzyl, 2-nitro-benzyl, 3-nitro-benzyl, 4-nitro-benzyl, 2-allyloxybenzyl, 3-bromo-benzyl, 4-bromo-benzyl, 3-hydroxy-benzyl, 3-methoxy-benzyl, 3-carboxybenzyl, 3-amino-benzyl, 4-amino-benzyl, 2-cyano-benzyl, 3-(N-acetylamino)-benzyl, 3,4-dimethoxy-benzyl, 3,4-methylenedioxy-benzyl, 4-fluoro-benzyl, 4-difluoromethoxybenzyl, 4-hydroxymethyl-benzyl, 4-carboxy-benzyl, 4-acetylamino-benzyl, 4-(ethoxyoxalyl-amino)-benzyl, 4-(3-hydroxy-prop-1-ynyl)-benzyl, 4-fluoro-benzyl, 3,4-dichloro-benzyl, benzo[1,3]dioxol-5-ylmethyl, 2-furanyl, 3-furanyl, 2-(5-acetyl)-thienyl, 3-pyridinyl, 3-(4-methoxy)-pyridinyl, 4-pyridinyl, 4-[1,2,4]triazolyl, quinolin-2-yl or quinolin-2-ylmethyl.

In a most preferred embodiment the compound of the invention is
2-Hydroxy-4-(4-nitro-phenoxy)-benzoic acid;
4-(4-Fluoro-benzylamino)-2-hydroxy-benzoic acid;
4-(4-Amino-phenoxy)-2-hydroxy-benzoic acid;
2,2,2-Trifluoro-N-[4-(4-fluoro-benzyloxy)-2-hydroxy-phenyl]-acetamide;
4-(4-Fluoro-benzyloxy)-2-hydroxy-benzoic acid;
4-(4-Acetylamino-benzylamino)-2-hydroxy-benzoic acid;
4-(4-Difluoromethoxy-benzylamino)-2-hydroxy-benzoic acid;
2-Hydroxy-4-(3-nitro-benzylamino)-benzoic acid;
2-Hydroxy-5-(4-nitro-phenylazo)-benzoic acid;
2-Hydroxy-4-(3,5-dimethyl-isoxazol-4-yl-methyloxy)-benzoic acid;
2-Benzyloxy-4-(2-nitro-phenoxy)-benzoic acid;
2-Hydroxy-4-(2-nitro-phenylamino)-benzoic acid;
2-Hydroxy-4-(quinolin-2-ylmethoxy)-benzoic acid;
4-(3-Bromo-benzyloxy)-2-hydroxy-benzoic acid;
4-(4-Bromo-benzyloxy)-2-hydroxy-benzoic acid;
4-(3-Bromo-benzyloxy)-2-hydroxy-benzoic acid hydrazide;
2-Hydroxy-4-[4-(3-hydroxy-prop-1-ynyl)-benzylamino]-benzoic acid;
4-(4-Fluoro-benzylamino)-2-hydroxy-benzonitrile;
5-(4-Fluoro-benzylamino)-2-(1H-tetrazol-5-yl)-phenol;
3-[4-(4-Fluoro-benzylamino)-2-hydroxy-phenyl]-4H-[1,2,4]oxadiazol-5-one;
5-(4-Fluoro-benzylamino)-2-(2-oxo-2,3-dihydro-2$\lambda^4$-[1,2,3,5]oxathiadiazol-4-yl)-phenol;
5-(4-Fluoro-benzylamino)-2-(5-methyl-4,5-dihydro-[1,2,4]oxadiazol-3-yl)-phenol;
4-(3,4-Dichloro-benzylamino)-2-hydroxy-benzonitrile; or
4-[(Benzo[1,3]dioxol-5-ylmethyl)-amino]-2-hydroxy-benzonitrile;
or a pharmaceutically-acceptable addition salt thereof.

In a sixth preferred embodiment the compound of the invention is a compound of Formula I, wherein $R^4$ represents a group of formula Y or -L'-Y; wherein Y represents a non-aromatic heterocyclic group, which heterocyclic group may optionally be substituted once or twice with substituents selected from the group consisting of alkyl, cycloalkyl or cycloalkyl-alkyl; and L' represents alkyl or alkenyl.

In a more preferred embodiment $R^4$ represents pyrrolidinyl or pyrrolidinyl-alkyl, in particular pyrrolidin-1-yl or pyrrolidin-1-yl-propyl; tetrahydrofuranyl or tetrahydrofuranyl-alkyl, in particular tetrahydrofuran-3-yl or tetrahydrofuran-3-yl-propyl; tetrahydropyranyl or tetrahydropyranyl-alkyl, in particular tetrahydro-pyran-4-yl or tetrahydro-pyran-4-yl-propyl; piperidinyl or piperidinyl-alkyl, in particular piperidin-1-yl or piperidin-1-yl-propyl; which heterocyclic group may optionally be substituted once or twice with substituents selected from the group consisting of alkyl, cycloalkyl and cycloalkyl-alkyl.

In a most preferred embodiment the compound of the invention is
2-Hydroxy-4-(tetrahydro-pyran-4-yloxy)-benzoic acid; or
2-Hydroxy-4-(3-piperidin-1-yl-propoxy)-benzoic acid;
or a pharmaceutically-acceptable addition salt thereof.

In a seventh preferred embodiment the compound of the invention is a compound of Formula I, wherein $R^4$ represents a group of formula -Z'-L"-Z"; wherein Z' and Z", independently of one another, represent a mono-, bi- or polycyclic aryl or heteroaryl group, which aryl or heteroaryl group may optionally be substituted one or more times with substituents selected from halo, alkyl, haloalkyl, cycloalkyl, cycloalkyl-alkyl, hydroxy, alkoxy, haloalkoxy, cycloalkoxy, hydroxyalkyl, alkoxy-alkyl, alkenyloxy, alkynyl, hydroxyalkynyl, nitro, amino, N-alkyl-amino, N,N-dialkyl-amino, cyano, carboxy, alkyl-carbonyl, alkyloxalyl, alkoxyoxalyl, alkyloxalyl-amino, alkoxyoxalyl-amino, alkoxy-carbonyl, carbamoyl, N-alkyl-carbamoyl, N-(alkylcarbonyl)amino, N,N-di(alkyl-carbonyl)amino, alkoxyoxalyl-amino, sulfamoyl, N-alkyl-sulfamoyl, N,N-dialkyl-sulfamoyl, N-phenyl-sulfamoyl, methylenedioxy, ethylenedioxy, propylenedioxy, phenyl, phenyloxy, benzyl or benzyloxy; and L" represents a single (covalent) bond, or a linker selected from alkyl, O, OCH$_2$, S, SCH$_2$, (CO), (CO)CH$_2$, NH, NHCH$_2$, (SO$_2$)NH, NH(SO$_2$), pyrrolidinyl and piperidinyl.

In a more preferred embodiment Z' and Z", independently of one another, are selected the group of phenyl, naphthyl, furanyl, thienyl, isoxazolyl, triazolyl, pyridinyl and indolyl; which aryl or heteroaryl group may optionally be substituted one or more times with substituents selected from halo, alkyl, haloalkyl, hydroxy, alkoxy, haloalkoxy, hydroxyalkyl, alkoxy-alkyl, nitro, amino, N,N-dialkyl-amino, cyano, carboxy, alkyl-carbonyl, N-(alkyl-carbonyl)amino, N,N-di(alkyl-carbonyl)amino, alkoxyoxalyl-amino, sulfamoyl, N,N-dialkyl-sulfamoyl, methylenedioxy, ethylenedioxy, propylenedioxy, phenyl, phenyloxy, benzyl or benzyloxy.

In an even more preferred embodiment $R^4$ represents a group of formula -Z'-L"-Z"; wherein Z' represents phenyl, in particular phen-4-yl; which phenyl may optionally be substituted one or two times with substituents selected from halo, alkyl, haloalkyl, cycloalkyl, cycloalkyl-alkyl, hydroxy, alkoxy, haloalkoxy, cycloalkoxy, hydroxyalkyl, alkoxy-alkyl, alkenyloxy, nitro, amino, N-alkyl-amino, N,N-dialkyl-amino, cyano, carboxy, alkyl-carbonyl, alkyloxalyl, alkoxyoxalyl, alkyloxalyl-amino, alkoxyoxalyl-amino, alkoxy-carbonyl, carbamoyl, N-alkyl-carbamoyl, N-(alkyl-carbonyl)amino, N,N-di(alkyl-carbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, propylenedioxy, phenyl, phenyloxy, benzyl and benzyloxy; and Z" represent phenyl; naphthyl, in particular naphth-1-yl or naphth2-yl; furanyl, in particular furan-2-yl or furan-3-yl; thienyl, in particular thien-2-yl or thien-3-yl; isoxazolyl, in particular isoxazo-3-yl or isoxazo-4-yl; triazolyl, in particular [1,2,4]triazol-1-yl or [1,2,4]triazol-2-yl; pyridinyl, in particular pyridin-2-yl, pyridin-3-yl or pyridin-4-yl; indolyl, in particular indol-4-yl or indol-5-yl; which aryl or heteroaryl group may optionally be substituted one or two times with substituents selected from halo, alkyl, haloalkyl, cycloalkyl, cycloalkyl-alkyl, hydroxy, alkoxy, haloalkoxy, cycloalkoxy, hydroxyalkyl, alkoxy-alkyl, alkenyloxy, nitro, amino, N-alkyl-amino, N,N-dialkyl-amino, cyano, carboxy, alkyl-carbonyl, alkyloxalyl, alkoxyoxalyl, alkyloxalyl-amino, alkoxyoxalyl-amino, alkoxy-carbonyl, carbamoyl, N-alkyl-carbamoyl, N-(alkyl-carbonyl)amino, N,N-di(alkyl-carbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, propylenedioxy, phenyl, phenyloxy, benzyl and benzyloxy; and L" represents a single (covalent) bond, or a linker selected from alkyl, O, OCH$_2$, S, (CO), NH, (SO$_2$)NH, NH(SO$_2$), pyrrolidinyl and piperidinyl.

In a yet more preferred embodiment R$^4$ represents a group of formula -Z'-L"-Z"; wherein Z' represents phenyl, in particular phen-4-yl; which phenyl may optionally be substituted one or two times with substituents selected from halo, CF$_3$, hydroxy, alkoxy, nitro, amino, N,N-dialkyl-amino, cyano, N,N-di(alkyl-carbonyl)amino, alkoxyoxalyl-amino, phenyl, phenyloxy, benzyl and benzyloxy; and Z" represent phenyl; naphthyl, in particular naphth-1-yl or naphth2-yl; furanyl, in particular furan-2-yl or furan-3-yl; thienyl, in particular thien-2-yl or thien-3-yl; isoxazolyl, in particular isoxazo-3-yl or isoxazo-4-yl; triazolyl, in particular [1,2,4]triazol-1-yl or [1,2,4]triazol-2-yl; pyridinyl, in particular pyridin-2-yl, pyridin-3-yl or pyridin-4-yl; indolyl, in particular indol-4-yl or indol-5-yl; which aryl or heteroaryl group may optionally be substituted one or two times with substituents selected from halo, alkyl, CF$_3$, hydroxy, alkoxy, CF$_3$O, hydroxyalkyl, nitro, amino, cyano, carboxy, alkyl-carbonyl, N-(alkyl-carbonyl)amino, N,N-di(alkyl-carbonyl) amino, alkoxyoxalyl-amino, sulfamoyl, N,N-dialkyl-sulfamoyl, methylenedioxy, ethylenedioxy, propylenedioxy, phenyl, phenyloxy, benzyl and benzyloxy; and L" represents a single (covalent) bond, or a linker selected from alkyl, O, OCH$_2$, S, (CO), NH, (SO$_2$)NH, NH(SO$_2$), pyrrolidinyl and piperidinyl.

In a still more preferred embodiment R$^4$ represents 3-phenoxy-phenyl, 4-phenoxy-phenyl, 3-benzyloxy-phenyl, 4-benzyloxy-phenyl, biphenyl-2-yl, biphenyl-3-yl, biphenyl-4-yl, 3-nitro-biphenyl-4-yl, 3-amino-biphenyl-4-yl, 3-(ethoxyoxalyl-amino)-biphenyl-4-yl, 3-diacetylamino-biphenyl-4-yl, 3-dimethylamino-biphenyl-4-yl, 3-carboxy-biphen-4-yl, 3-(3,4-dihydro-2H-benzo[b][1,4]dioxepin-7-yl)-phenyl, 3-(2,3-dihydro-benzo[1,4]dioxin-6-yl)-phenyl, 4-carboxy-biphen-4-yl, 4-(4-chloro-phenylsulfanyl)-3-nitro-phenyl, 4-benzo[1,3]dioxol-5-yl-phenyl, 2'-cyano-biphenyl-4-yl, 3'-acetyl-biphenyl-3-yl, 3'-acetyl-biphenyl-4-yl, 3'-acetyl-biphenyl-4-yl, 3'-acetylamino-biphenyl-4-yl, 3'-amino-biphenyl-3-yl, 3'-amino-biphenyl-4-yl, 3'-hydroxy-biphenyl-4-yl, 3'-methoxy-biphenyl-3-yl, 3'-methoxy-biphenyl-4-yl, 3'-nitro-biphenyl-3-yl, 3'-nitro-biphenyl-4-yl, 3'-carboxyamino-biphenyl-3-yl, 4'-hydroxymethyl-biphenyl-4-yl, 4'-hydroxy-3'-methoxy-biphenyl-3-yl, 3',4'-dichloro-biphenyl-3-yl, 3',5'-dichloro-biphenyl-3-yl, 2',6'-dimethoxy-biphenyl-3-yl, 2',6'-dimethoxy-biphenyl-4-yl, 4'-dimethylsulfamoyl-biphenyl-3-yl, 3'-cyano-biphenyl-3-yl, 2',4'-dimethoxy-biphenyl-3-yl, 3',4'-dimethoxy-biphenyl-4-yl, 3',4'-dichloro-biphenyl-3-yl, 3',4'-dichloro-biphenyl-4-yl, 3',5'-dichloro-biphenyl-3-yl, 3',5'-dichloro-biphenyl-4-yl, 3',4'-(methylendioxy)-biphenyl-3-yl, 3',4'-(methylendioxy)-biphenyl-4-yl, 4'-hydroxymethyl-biphenyl-4-yl, 4'-dimethylsulfamoyl-biphenyl-3-yl, 4'-dimethylsulfamoyl-biphenyl-4-yl, 3-naphthalen-1-yl-phenyl, 3-naphthalen-2-yl-phenyl, 3-pyridin-3-yl-phenyl, 3-pyridin-4-yl-phenyl, 4-pyridin-3-yl-phenyl 4-pyridin-4-yl-phenyl, 4-(pyridin-2-ylsulfamoyl)-phenyl, 3-furan-3-yl-phenyl, 3-furan-4-yl-phenyl, 4-methoxy-pyridin-3-yl-phenyl, 4-furan-2-yl-phenyl, 4-furan-3-yl-phenyl, 4-(furan-2-ylsulfanyl)-3-nitro-phenyl, 3-(3,5-dimethyl-isoxazol-4-yl)-phenyl, 5-acetyl-thiophen-2-yl-phenyl, 4-[1,2,4]triazol-1-yl-phenyl, 3-(1-methyl-1H-indol-5-yl)-phenyl, 4-(1-methyl-1H-indol-5-yl)-phenyl, 3-(1H-indol-5-yl)-phenyl or 4-(1H-indol-5-yl)-phenyl.

In a most preferred embodiment the compound of the invention is
4-(Biphenyl-4-ylmethoxy)-2-hydroxy-benzoic acid;
2-Hydroxy-4-(3-nitro-biphenyl-4-yloxy)-benzoic acid;
4-(3-Amino-biphenyl-4-yloxy)-2-hydroxy-benzoic acid;
4-[3-(Ethoxyoxalyl-amino)-biphenyl-4-yloxy]-2-hydroxy-benzoic acid;
4-(3-Diacetylamino-biphenyl-4-yloxy)-2-hydroxy-benzoic acid;
4-(3-Dimethylamino-biphenyl-4-yloxy)-2-hydroxy-benzoic acid;
4-(Biphenyl-3-ylmethoxy)-2-hydroxy-benzoic acid;
2-Hydroxy-4-(4-[1,2,4]triazol-1-yl-benzyloxy)-benzoic acid;
4-(3'-Acetyl-biphenyl-4-ylmethoxy)-2-hydroxy-benzoic acid;
4'-(4-Carboxy-3-hydroxy-phenoxymethyl)-biphenyl-3-carboxylic acid;
2-Hydroxy-4-(3'-hydroxy-biphenyl-4-ylmethoxy)-benzoic acid;
2-Hydroxy-4-(3'methoxy-biphenyl-4-ylmethoxy)-benzoic acid;
2-Hydroxy-4-(3'-nitro-biphenyl-4-ylmethoxy)-benzoic acid;
4-[3',4'-(methylendioxy)-biphenyl-4-ylmethoxy]-2-hydroxy-benzoic acid;
4-(3'-Amino-biphenyl-4-ylmethoxy)-2-hydroxy-benzoic acid;
4-(3'-Acetylamino-biphenyl-4-ylmethoxy)-2-hydroxy-benzoic acid;
2-Hydroxy-4-(4'-hydroxymethyl-biphenyl-4-ylmethoxy)-benzoic acid;
4'-(4-Carboxy-3-hydroxy-phenoxymethyl)biphenyl-4-carboxylic acid;
2-Hydroxy-4-(3',4'-dimethoxy-biphenyl-4-ylmethoxy)-benzoic acid;
2-Hydroxy-(4-pyridin-3-yl-benzyloxy)-benzoic acid;
2-Hydroxy-4-(4-pyridin-4-yl-benzyloxy)-benzoic acid;
2-Hydroxy-4-[4-(4-methoxy-pyridin-3-yl)-benzyloxy]-benzoic acid;
4-(4-Furan-3-yl-benzyloxy)-2-hydroxy-benzoic acid;
4-[4-(5-Acetyl-thiophen-2-yl)-benzyloxy]-2-hydroxy-benzoic acid;
4-(4-Furan-2-yl-benzyloxy)-2-hydroxy-benzoic acid;
Biphenyl-4-carboxylic acid 4-carboxy-3-hydroxy-phenyl ester;
4-(Biphenyl-2-ylmethoxy)-2-hydroxy-benzoic acid;
4-[3',4'-(Methylendioxy)-biphenyl-3-ylmethoxy]-2-hydroxy-benzoic acid;
4-(2'-Cyano-biphenyl ylmethoxy)-2-hydroxy-benzoic acid;
2-Hydroxy-5-[4-(pyridin-2-ylsulfamoyl)-phenylazo]-benzoic acid;
4-[(Biphenyl-4-carbonyl)-amino]-2-methoxy-benzoic acid;
4-[(Biphenyl-4-carbonyl)-amino]-2-hydroxy-benzoic acid;
4-(3'-Acetyl-biphenyl-3-ylmethoxy)-2-hydroxy-benzoic acid;
3'-(4-Carboxy-3-hydroxy-phenoxymethyl)-biphenyl-3-carboxylic acid;
2-Hydroxy-4-(3'-methoxy-biphenyl-3-ylmethoxy)-benzoic acid;
2-Hydroxy-4-(3'-nitro-biphenyl-3-ylmethoxy)-benzoic acid;
4-(3'-Amino-biphenyl-3-ylmethoxy)-2-hydroxy-benzoic acid;
4-(3'-carboxyamino-biphenyl-3-ylmethoxy)-2-hydroxy-benzoic acid;
2-Hydroxy-4-(4'-hydroxy-3'-methoxy-biphenyl-3-ylmethoxy)-benzoic acid;
2-Hydroxy-4-(3-pyridin-3-yl-benzyloxy)-benzoic acid;

4-(3-Furan-3-yl-benzyloxy)-2-hydroxy-benzoic acid;
4-[3-(5-Acetyl-thiophen-2-yl)-benzyloxy]-2-hydroxy-benzoic acid;
4-(3',4'-Dichloro-biphenyl-3-ylmethoxy)-2-hydroxy-benzoic acid;
4-(3',5'-Dichloro-biphenyl-3-ylmethoxy)-2-hydroxy-benzoic acid;
4-(2',6'-Dimethoxy-biphenyl-3-ylmethoxy)-2-hydroxy-benzoic acid;
2-Hydroxy-4-[3-(1-methyl-1H-indol-5-yl)-benzyloxy]-benzoic acid;
2-Hydroxy-4-[3-(1H-indol-5-yl)-benzyloxy]-benzoic acid;
4-[3-(3,4-Dihydro-2H-benzo[b][1,4]dioxepin-7-yl)-benzyloxy]-2-hydroxy-benzoic acid;
4-[3-(2,3-Dihydro-benzo[1,4]dioxin-6-yl)-benzyloxy]-2-hydroxy-benzoic acid;
2-Hydroxy-4-(3-naphthalen-1-yl-benzyloxy)-benzoic acid;
2-Hydroxy-4-(3-naphthalen-2-yl-benzyloxy)-benzoic acid;
4-(4'-Dimethylsulfamoyl-biphenyl-3-ylmethoxy)-2-hydroxy-benzoic acid;
4-[3-(3,5-Dimethyl-isoxazolyl)-benzyloxy]-2-hydroxy-benzoic acid;
4-(3'-Cyano-biphenyl-3-ylmethoxy)-2-hydroxy-benzoic acid;
4-(2',4'-Dimethoxy-biphenyl-3-ylmethoxy)-2-hydroxy-benzoic acid;
4-[4-(Furan-2-ylsulfanyl-3-nitro-benzylamino]-2-hydroxy-benzoic acid;
4-[4-(4-Chloro-phenylsulfanyl)-3-nitro-benzylamino]-2-hydroxy-benzoic acid;
4-[(3',4'-Dichloro-biphenyl-4-ylmethyl)-amino]-2-hydroxy-benzoic acid;
2-Benzyloxy-4-(3-nitro-biphenyl-4-yloxy)-benzoic acid;
4-(4-Benzo[1,3]dioxol-5-yl-benzylamino)-2-hydroxy-benzoic acid;
2-Hydroxy-4-[4-(1-methyl-1H-indol-5-yl)-benzylamino]-benzoic acid;
2-Hydroxy-4-[(3'-methoxy-biphenyl-4-ylmethyl)-amino]-benzoic acid;
4-[(3'-Amino-biphenyl-4-ylmethyl)-amino]-2-hydroxy-benzoic acid;
4-(4-Benzoyl-benzyloxy)-2-hydroxy benzoic acid;
2-Hydroxy-4-(3-phenoxy-benzylamino)-benzonitrile;
4-(3-Benzyloxy-benzylamino)-2-hydroxy-benzonitrile; or
4-[(Biphenyl-4-ylmethyl)-amino]-2-hydroxy-benzonitrile;
or a pharmaceutically-acceptable addition salt thereof.

In an eight preferred embodiment the compound of the invention is a compound of Formula I, wherein $R^1$ represents —OH, —CN, —(CO)OH, —CO-alkyl, —(CO)NH$_2$, —(CO)NH-alkyl, —CHNOH; —NH(CO)haloalkyl, —NH(SO$_2$)alkyl, 1H-tetrazolyl, [1,2,4]-oxadiazol-5-on-3-yl, 5-methyl-2,5-dihydro-[1,2,4]-oxadiazol-3-yl or [1,2,3,5]-oxathiadiazol-2-oxide-4-yl;

$R^2$ represents halo, CF$_3$, hydroxy, alkoxy, phenyl-alkoxy, amino, nitro or cyano;

X represents O, OCH$_2$, O(CO), NH, NHCH$_2$, NH(CO) or N=N (read in the stated direction); and $R^4$ represents methyl, ethyl, propyl, butyl, pentyl, hexyl, heptyl, octyl, nonyl, methoxy-ethyl, methoxy-ethoxy-ethyl, butenyl, pentenyl, hexenyl, heptenyl, octenyl, nonenyl, octa-2,6-dienyl, 3,7-dimethyl-octa-2,6-dienyl, hydroxyhexyl, hydroxyoctyl, 2,3-dihydroxypropyl, 3,4-dihydroxybutyl, 5,6-dihydroxyhexyl, 7,8-dihydroxyoctyl, 7,7-dihydroxy-3,6-dimethyl-octyl, —(CO)OH, carboxymethoxy or acryloyl.

In a ninth preferred embodiment the compound of the invention is a compound of Formula I, wherein $R^1$ represents —OH, —CN, —(CO)OH, —CO-alkyl, —(CO)NH$_2$, —(CO)NH-alkyl, —CHNOH; —NH(CO)-haloalkyl, —NH(SO$_2$)-alkyl, 1H-tetrazolyl, [1,2,4]-oxadiazol-5-on-3-yl, 5-methyl-2,5-dihydro-[1,2,4]-oxadiazol-3-yl or [1,2,3,5]-oxathiadiazol-2-oxide-4-yl;

$R^2$ represents halo, CF$_3$, hydroxy, alkoxy, phenyl-alkoxy, amino, nitro or cyano;

X represents O, OCH$_2$, O(CO), NH, NHCH$_2$, NH(CO) or N=N (read in the stated direction); and $R^4$ represents phenyl, 2-nitro-phenyl, 3-nitro-phenyl, 4-nitro-phenyl, 2-allyloxy-phenyl, 3-bromo-phenyl, 4-bromo-phenyl, 3-hydroxy-phenyl, 3-methoxy-phenyl, 3-carboxy-phenyl, 3-amino-phenyl, 4-amino-phenyl, 2-cyano-phenyl, 3-(N-acetylamino)-phenyl, 3,4-dimethoxy-phenyl, 3,4-methylenedioxy-phenyl, 4-difluoromethoxy-phenyl, 4-hydroxymethyl-phenyl, 4-carboxy-phenyl, 4-acetylamino-phenyl, 4-fluorophenyl, 4-(ethoxyoxalyl-amino)-phenyl, benzyl, 2-nitro-benzyl, 3-nitro-benzyl, 4-nitro-benzyl, 2-allyloxybenzyl, 3-bromo-benzyl, 4-bromo-benzyl, 3-hydroxy-benzyl, 3-methoxy-benzyl, 3-carboxy-benzyl, 3-amino-benzyl, 4-amino-benzyl, 2-cyano-benzyl, 3-(N-acetylamino)-benzyl, 3,4-dimethoxy-benzyl, 3,4-methylenedioxy-benzyl, 4-fluoro-benzyl, 4-difluoromethoxy-benzyl, 4-hydroxymethyl-benzyl, 4-carboxy-benzyl, 4-acetylamino-benzyl, 4-(ethoxyoxalyl-amino)-benzyl, 4-(3-hydroxy-prop-1-ynyl)-benzyl, 4-fluoro-benzyl, 3,4-dichloro-benzyl, benzo[1,3]dioxol-5-ylmethyl, 2-furanyl, 3-furanyl, 2-(5-acetyl)-thienyl, 3-pyridinyl, 3-(4-methoxy)-pyridinyl, 4-pyridinyl, 4-[1,2,4]triazolyl, quinolin-2-yl or quinolin-2-ylmethyl.

In a tenth preferred embodiment the compound of the invention is a compound of Formula I, wherein $R^1$ represents —OH, —CN, —(CO)OH, —CO-alkyl, —(CO)NH$_2$, —(CO)NH-alkyl, —CHNOH; —NH(CO)-haloalkyl, —NH(SO$_2$)-alkyl, 1H-tetrazolyl, [1,2,4]-oxadiazol-5-on-3-yl, 5-methyl-2,5-dihydro-[1,2,4]-oxadiazol-3-yl or [1,2,3,5]-oxathiadiazol-2-oxide-4-yl;

$R^2$ represents halo, CF$_3$, hydroxy, alkoxy, phenyl-alkoxy, amino, nitro or cyano;

X represents O, OCH$_2$, O(CO), NH, NHCH$_2$, NH(CO) or N=N (read in the stated direction); and $R^4$ represents pyrrolidinyl or pyrrolidinyl-alkyl, in particular pyrrolidin-1-yl or pyrrolidin-1-yl-propyl; tetrahydrofuranyl or tetrahydrofuranyl-alkyl, in particular tetrahydrofuran-3-yl or tetrahydrofuran-3-yl-propyl; tetrahydropyranyl or tetrahydropyranyl-alkyl, in particular tetrahydro-pyran-4-yl or tetrahydro-pyran-4-yl-propyl; piperidinyl or piperidinyl-alkyl, in particular piperidin-1-yl or piperidin-1-yl-propyl; which heterocyclic group may optionally be substituted once or twice with substituents selected from the group consisting of alkyl, cycloalkyl and cycloalkyl-alkyl.

In an eleventh preferred embodiment the compound of the invention is a compound of Formula I, wherein $R^1$ represents —OH, —CN, —(CO)OH, —CO-alkyl, —(CO)NH$_2$, —(CO)NH-alkyl, —CHNOH; —NH(CO)-haloalkyl, —NH(SO$_2$)-alkyl, 1H-tetrazolyl, [1,2,4]-oxadiazol-5-on-3-yl, 5-methyl-2,5-dihydro-[1,2,4]-oxadiazol-3-yl or [1,2,3,5]-oxathiadiazol-2-oxide-4-yl;

$R^2$ represents halo, CF$_3$, hydroxy, alkoxy, phenyl-alkoxy, amino, nitro or cyano;

X represents O, OCH$_2$, O(CO), NH, NHCH$_2$, NH(CO) or N=N (read in the stated direction); and $R^4$ represents 3-phenoxy-phenyl, 4-phenoxy-phenyl, 3-benzyloxy-phenyl, 4-benzyloxy-phenyl, biphenyl-2-yl, biphenyl-3-yl, biphenyl-4-yl, 3-nitro-biphenylyl, 3-amino-biphenyl-4-yl, 3-(ethoxyoxalyl-amino)-biphenyl-4-yl, 3-diacetylamino-biphenyl-4-yl, 3-dimethylamino-biphenyl-4-yl, 3-carboxy-biphenyl, 3-(3,4-dihydro-2H-benzo[b][1,4]dioxepin-7-yl)-phenyl, 3-(2,3-dihydro-benzo[1,4]dioxin-6-yl)-phenyl, 4-carboxy-biphen-4-yl, 4-(4-chloro-phenylsulfanyl)-3-nitro-phenyl, 4-benzo[1,3]dioxol-5-yl-phenyl, 2'-cyano-biphenyl-4-yl, 3'-acetyl-biphenyl-3-yl, 3'-acetyl-biphenyl-4-yl, 3'-acetyl-biphenyl-4-yl, 3'-acetylamino-biphenyl-4-yl, 3'-amino-biphenyl-3-yl, 3'-amino-biphenylyl, 3'-hydroxy-biphenyl-4-yl, 3'-methoxy-biphenyl-3-yl, 3'-methoxy-biphenyl-4-yl, 3'-nitro-biphenyl-3-yl, 3'-nitro-biphenyl-4-yl, 3'-carboxyamino-biphenyl-3-yl, 4'-hydroxymethyl-biphenyl-4-yl, 4'-hydroxy-3'-methoxy-biphenyl-3-yl, 3',4'-dichloro-biphenyl-3-yl, 3',5'-dichloro-biphenyl-3-yl, 2',6'-dimethoxy-biphenyl-3-yl, 2',6'-dimethoxy-biphenyl-4-yl, 4'-dimethylsulfamoyl-biphenyl-3-yl, 3'-cyano-biphenyl-3-yl, 2',4'-dimethoxy-biphenyl-3-yl, 3',4'-dimethoxy-biphenyl-4-yl, 3',4'-dichloro-biphenyl-3-yl, 3',4'-dichloro-biphenyl-4-yl, 3',5'-dichloro-biphenyl-3-yl, 3',5'-dichloro-biphenyl-4-yl, 3',4'-(methylendioxy)-biphenyl-3-yl, 3',4'-(methylendioxy)-biphenyl-4-yl, 4'-hydroxymethyl-biphenyl-4-yl, 4'-dimethylsulfamoyl-biphenyl-3-yl, 4'-dimethylsulfamoyl-biphenyl-4-yl, 3-naphthalen-1-yl-phenyl, 3-naphthalen-2-yl-phenyl, 3-pyridin-3-yl-phenyl, 3-pyridin-4-yl-phenyl, 4-pyridin-3-yl-phenyl, 4-pyridin-4-yl-phenyl, 4-(pyridin-2-ylsulfamoyl)-phenyl, 3-furan-3-yl-phenyl, 3-furan-4-yl-phenyl, 4-methoxy-pyridin-3-yl-phenyl, 4-furan-2-yl-phenyl, 4-furan-3-yl-phenyl, 4-(furan-2-ylsulfanyl)-3-nitro-phenyl, 3-(3,5-dimethyl-isoxazol-4-yl)phenyl, 5-acetyl-thiophen-2-yl-phenyl, 4-[1,2,4]triazol-1-yl-phenyl, 3-(1-methyl-1H-indol-5-yl)-phenyl, 4-(1-methyl-1H-indol-5-yl)-phenyl, 3-(1H-indol-5-yl)-phenyl or 4-(1H-indol-5-yl)-phenyl.

In another aspect the invention provides a compound represented by Formula II

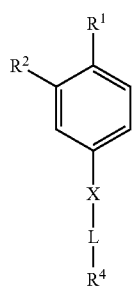

any of its enantiomers or any mixture of its enantiomers, or a prodrug, or a pharmaceutically-acceptable addition salt thereof, wherein $R^1$ represents OH, CN, —(CO)OH, —CO—R', —(CO)NH—R', —CHNO—R', —NH(CO)—R', —(SO$_2$)NH—R' or —NH(SO$_2$)—R'; wherein R' represents hydrogen, alkyl, cycloalkyl, cycloalkyl-alkyl, alkyl-cycloalkyl, alkyl-cycloalkyl-alkyl, haloalkyl;

$R^2$ represents halo, haloalkyl, hydroxy, alkoxy, cycloalkoxy, cycloalkyl-alkoxy, amino, nitro or cyano;

X represents O, O(CO), CO, (CO)O, NH, NH(CO), (CO)NH, N═CH, CH$_2$, CH═N, N═N, S, (SO$_2$)NH or NH(SO$_2$);

L may be absent or present, and represents a linking group selected from alkyl, cycloalkyl, cycloalkyl-alkyl, alkyl-cycloalkyl, alkyl-cycloalkyl-alkyl, alkenyl, alkynyl, aryl, aryl-alkyl or heteroaryl; and $R^4$ represents hydrogen, alkyl, cycloalkyl, cycloalkyl-alkyl, alkoxy-alkyl, cycloalkoxy-alkyl, cycloalkoxy-cycloalkyl, cycloalkoxy-cycloalkoxy, alkoxy-alkoxy-alkyl, cycloalkoxy-alkoxy-alkyl, alkenyl, alkynyl, hydroxy-alkyl, dihydroxy-alkyl, —CO—R''', —NH—R''', —NH—CO— R''', —NH(SO$_2$)R''', —(SO$_2$)NH—R''', wherein R''' represents hydrogen, alkyl, cycloalkyl, cycloalkyl-alkyl, haloalkyl; or R''' represents aryl, biaryl, aryl-alkyl or heteroaryl, which aryl or heteroaryl groups may be mono-, bi- or poly-cyclic, and which aryl or heteroaryl groups may optionally be substituted one or more times with substituents selected from the group consisting of halo, alkyl, haloalkyl, cycloalkyl, cycloalkyl-alkyl, hydroxy, alkoxy, cycloalkoxy, haloalkoxy, nitro and amino; or $R^4$ represents a non-aromatic mono-, bi- or poly-cyclic, heterocyclic group, which non-aromatic heterocyclic group may optionally be substituted once or twice with substituents selected from the group consisting of alkyl, cycloalkyl or cycloalkyl-alkyl; or $R^4$ represents aryl, biaryl, aryl-alkyl, aryl-carbonyl, aryl-aryl-alkyl, aryl-carbonyl-aryl, heteroaryl, heteroaryl-alkyl, heteroaryl-aryl-alkyl, which aryl or heteroaryl groups may be mono-, bi- or poly-cyclic, and which aryl or heteroaryl groups may optionally be substituted one or more times with substituents selected from the group consisting of halo, alkyl, haloalkyl, cycloalkyl, cycloalkyl-alkyl, hydroxy, alkoxy, haloalkoxy, cycloalkoxy, hydroxyalkyl, alkenyloxy, nitro, amino, N-alkyl-amino, N,N-dialkyl-amino, cyano, carboxy, alkyl-carbonyl, alkyloxalyl, alkoxyoxalyl, alkyloxalyl-amino, alkoxyoxalyl-amino, alkoxy-carbonyl, carbamoyl, N-alkylcarbamoyl, N-(alkyl-carbonyl)amino, N,N-di(alkyl-carbonyl)amino, alkoxyoxalyl-amino, sulfamoyl, N-alkyl-sulfamoyl, N,N-dialkyl-sulfamoyl, N-aryl-sulfamoyl, N-heteroaryl-sulfamoyl, methylenedioxy, ethylenedioxy, aryl, aryloxy, aralkyl or aralkyloxy.

In a preferred embodiment the compound of the invention is a compound of Formula II, wherein $R^1$ represents OH, CN, —(CO)OH, —COCH$_3$, —(CO)NH$_2$, —CHNOH; —NH(CO)CF$_3$ or —NH(SO$_2$)CH$_3$.

In another preferred embodiment the compound of the invention is a compound of Formula II, wherein $R^2$ represents halo, hydroxy, alkoxy or cycloalkoxy.

In a third preferred embodiment the compound of the invention is a compound of Formula II, wherein X represents O, O(CO), (CO)O, NH, NH(CO), (CO)NH, N═CH, N═N or (SO$_2$)NH.

In a fourth preferred embodiment the compound of the invention is a compound of Formula II, wherein L is absent.

In a fifth preferred embodiment the compound of the invention is a compound of Formula II, wherein L represents a linking group selected from alkyl, alkenyl, phenyl or benzyl.

In a sixth preferred embodiment the compound of the invention is a compound of Formula II, wherein $R^4$ represents hydrogen, alkyl, cycloalkyl, cycloalkyl-alkyl, alkoxy-alkyl, alkoxy-alkoxy-alkyl, alkenyl, hydroxy-alkyl, dihydroxy-alkyl, —CO—R''', —(CO)O—R''', —NH—R''', —NH(CO)R''', —NH(SO$_2$)—R''' or —(SO$_2$)NH—R''', wherein R''' represents hydrogen, alkyl, cycloalkyl, cycloalkyl-alkyl, haloalkyl; or R''' represents phenyl, biphenyl or benzyl, which aryl groups may optionally be substituted one or more times with halo, nitro and/or amino; or R''' represents a 5- or 6-membered heteroaryl group; which heteroaryl group may optionally be substituted once or twice with substituents selected from the group consisting of halo, alkyl, cycloalkyl, cycloalkyl-alkyl, alkoxy, cycloalkoxy, nitro, amino and phenyl; or $R^4$ represents a non-aromatic 5- or 6-membered monocyclic heterocyclic group selected from pyrrolidinyl, imidazolidinyl, tetrahydropyranyl, pyrazolidinyl, piperidinyl, morpholinyl and piperazinyl, which non-aromatic heterocyclic group may optionally be substituted once or twice with substituents selected from the group consisting of alkyl, cycloalkyl or cycloalkyl-alkyl; or $R^4$ represents phenyl, biphenyl, benzyl, benzoyl, benzoylphenyl or phenyl-benzyl, which aryl groups may optionally be substituted once or twice with substituents selected from the group consisting of halo, nitro, amino, cyano, hydroxy, alkoxy, haloalkoxy, hydroxyalkyl, alkenyloxy, carboxy, alkyl-carbonyl, alkyloxalyl, alkoxyoxalyl, alkyl-amino, alkyloxalyl-amino, alkoxyoxalyl-amino, N,N-dialkyl-amino, N-(alkyl-carbonyl)amino, N,N-di(alkyl-carbonyl)amino, alkoxyoxalyl-amino, methylenedioxy, phenyl, phenoxy, benzyl or benzyloxy; or $R^4$ represents a 5- or 6-membered monocyclic heteroaryl, heteroaryl-alkyl or heteroaryl-aryl-alkyl group, which heteroaryl groups may optionally be substituted once or twice with substituents selected from the group consisting of halo, alkyl, cycloalkyl, cycloalkyl-alkyl, alkoxy, cycloalkoxy, nitro, amino, carboxy, alkyl-carbonyl, alkyloxalyl, alkoxyoxalyl, alkyloxalyl-amino, alkoxyoxalyl-amino, alkoxy-carbonyl, carbamoyl, methylenedioxy, phenyl, phenoxy, benzyl or benzyloxy; or $R^4$ represents a bicyclic heteroaryl group, which may optionally be substituted once or twice with substituents selected from the group consisting of halo, alkyl, cycloalkyl, cycloalkyl-alkyl, alkoxy, cycloalkoxy, nitro, amino, carboxy, alkyl-carbonyl, alkyloxalyl, alkoxyoxalyl, alkyloxalyl-amino, alkoxyoxalyl-amino, alkoxy-carbonyl, carbamoyl, methylenedioxy, phenyl, phenoxy, benzyl or benzyloxy.

In a seventh preferred embodiment the compound of the invention is a compound of Formula II, wherein $R^4$ represents hydrogen, methyl, heptyl, octyl, methoxy-ethyl, methoxyethoxy-ethyl, butenyl, hexenyl, octenyl, octa-2,6-dienyl, hydroxyhexyl, hydroxyoctyl, 2,3-dihydroxypropyl, 3,4-dihydroxybutyl, 5,6-dihydroxyhexyl, 7,8-dihydroxyoctyl, 7,7-dihydroxy-3,6-dimethyl-octyl, —CO)OH, 2-pyridinylsulfamoyl.

In a most preferred embodiment the compound of the invention is
4-Octyloxy-benzene-1,2-diol;
2-Hydroxy-4-octyloxy-benzaldehyde;
1-(2-Hydroxy-4-octyloxy-phenyl)ethanone;
4-(3-Carboxy-acryloylamino)-2-hydroxy-benzoic acid;
4-Carboxymethoxy-2-hydroxy-benzoic acid;
4-[(Biphenyl-4-carbonyl)amino]-2-methoxy-benzoic acid;
4-[(Biphenyl-4-carbonyl)-amino]-2-hydroxy-benzoic acid;
2-Hydroxy-4-octyloxy-benzoic acid;
2-Hydroxy-4-octanyloxy-benzoic acid;
2-Hydroxy-4-octyloxy-benzamide;
2-Hydroxy-4-octyloxy-benzaldehyde oxime;
2-Hydroxy-4-octyloxy-benzonitrile;
2,2,2-Trifluoro-N-(2-hydroxy-4-octyloxy-phenyl)-acetamide;
N-(2-Hydroxy-4-octyloxy-phenyl)-methanesulfonamide;
4-(3,4-Dihydroxybutoxy)-2-hydroxy-benzoic acid;
4-Hex-5-enyloxy-2-hydroxy-benzoic acid;
4-(5,6-Dihydroxhexoxy)-2-hydroxy-benzoic acid;
2-Hydroxy-4-oct-7-enyloxy-benzoic acid;
4-(3,7-Dimethyl-octa-2,6-dienyloxy)-2-hydroxybenzoic acid;
2-Hydroxy-4-(6-hydroxyhexyloxy) benzoic acid;
2-Hydroxy-4-(2-methoxy-ethoxy)-benzoic acid;
4-(7,8-Dihydroxyoctyloxy)-2-hydroxy-benzoic acid;
4-(2,3-Dihydroxypropoxy)-2-hydroxy-benzoic acid;
2-Hydroxy-4-(8-hydroxy-octyloxy) benzoic acid;
2-Chloro-4-oct-7-enyloxy-benzoic acid;
2-Chloro-4-(7,8-dihydroxy-octyloxy) benzoic acid;
4-(7,7-Dihydroxy-3,6-dimethyl-octyloxy)-2-hydroxy benzoic acid;
2-Fluoro-4-oct-7-enyloxy-benzoic acid;
2-Fluoro-4-(7,8-dihydroxy-octyloxy) benzoic acid; or
5-Octyloxy-2-(1H-tetrazol-5-yl)-phenol;
or a pharmaceutically-acceptable addition salt thereof.

In an eighth preferred embodiment the compound of the invention is a compound of Formula II, wherein $R^4$ represents —CO—R''', —(CO)O—R''', —NH—R''', —NH(CO)—R''', —NH(SO$_2$)—R''' or —(SO$_2$)NH—R''', wherein R''' represents a heteroaryl group selected from furanyl, in particular 2- or 3-furanyl; thienyl, in particular 2-thienyl; pyridinyl, in particular 2-, 3- or 4-pyridinyl; isoxazolyl, in particular 3-, 4- or 5-isoxazolyl; pyrazolyl, in particular 1-, 3- or 4-pyrazolyl; triazolyl, in particular [1,2,3]triazolyl or [1,2,4]triazolyl; which heteroaryl groups may optionally be substituted once or twice with substituents selected from the group consisting of halo, alkyl, cycloalkyl, cycloalkyl-alkyl, alkoxy, cycloalkoxy, nitro, amino and phenyl.

In a most preferred embodiment the compound of the invention is
2-Hydroxy-5-[4-(pyridin-2-ylsulfamoyl)-phenylazo]-benzoic acid;
or a pharmaceutically-acceptable addition salt thereof.

In a ninth preferred embodiment the compound of the invention is a compound of Formula II, wherein $R^4$ represents tetrahydropyranyl or 1-piperidinyl.

In a most preferred embodiment the compound of the invention is
2-Hydroxy-4-(tetrahydro-pyran-4-yloxy)benzoic acid; or
2-Hydroxy-4-(3-piperidin-1-yl-propoxy)benzoic acid;
or a pharmaceutically-acceptable addition salt thereof.

In a tenth preferred embodiment the compound of the invention is a compound of Formula II, wherein $R^4$ represents phenyl, 3-hydroxy-phenyl, 3-methoxy-phenyl, 3-carboxy-phenyl, 3-amino-phenyl, 2-cyano-phenyl, 3-(N-acetylamino)-phenyl, 3-nitro-phenyl, 4-difluoromethoxy-phenyl, 4-hydroxymethyl-phenyl, 4-carboxy-phenyl, 4-nitro-phenyl, 4-fluorophenyl, 4-amino-phenyl, 4-(3-N-acetylamino)-phenyl, 3,4-dimethoxy-phenyl, 3,4-methylenedioxy-phenyl, 4-(ethoxyoxalyl-amino)-phenyl, phenoxy-phenyl, benzoyl-phenyl, 2-biphenyl, 3-biphenyl, 4-(3-amino)-biphenyl, 4-(3-nitro)biphenyl, 4-(3-ethoxyoxalyl-amino)-biphenyl, 4-(3-N,N-diacetylamino)-biphenyl, 4-(3-N,N-dimethylamino)-biphenyl, 4-(3'-acetyl)biphenyl, benzyl, benzoyl-benzyl, phenyl-benzyl, phenoxy-benzyl, 2-allyloxybenzyl or 2-hydroxy-4-benzyloxy-phenyl.

In a most preferred embodiment the compound of the invention is
2-Hydroxy-4-(4-nitro-phenoxy)-benzoic acid;
4-(4-Fluoro-benzylamino)-2-hydroxy-benzoic acid;
4-(4-Amino-phenoxy)-2-hydroxy-benzoic acid;
2-Hydroxy-4-(3-nitro-biphenyl-4-yloxy)benzoic acid;
4-(3-Amino-biphenyl-4-yloxy)-2-hydroxy-benzoic acid;
4-[3-(Ethoxyoxalyl-amino)-biphenyl-4-yloxy]-2-hydroxy-benzoic acid;
4-(3-Diacetylamino-biphenyl-4-yloxy)-2-hydroxy-benzoic acid;
4-(3-Dimethylamino-biphenyl-4-yloxy)-2-hydroxy-benzoic acid;
4-(Biphenyl-3-ylmethoxy)-2-hydroxy-benzoic acid;
4-(3'-Acetyl-biphenyl-4-ylmethoxy)-2-hydroxy-benzoic acid;
4'-(4-Carboxy-3-hydroxy-phenoxymethyl)-biphenyl-3-carboxylic acid;
2-Hydroxy-4-(3'-hydroxy-biphenyl-4-ylmethoxy)-benzoic acid;

2-Hydroxy-4-(3'methoxy-biphenyl-4-ylmethoxy)-benzoic acid;
2-Hydroxy-4-(3'-nitro-biphenyl-4-ylmethoxy)-benzoic acid;
4-[3',4'-(Methylenedioxy)-biphenyl-4-ylmethoxy]-2-hydroxy-benzoic acid;
4-(3'-Amino-biphenyl-4-ylmethoxy)-2-hydroxy-benzoic acid;
4-(3'-Acetylamino-biphenyl-4-ylmethoxy)-2-hydroxy-benzoic acid;
2-Hydroxy-4-(4'-hydroxymethyl-biphenyl-4-ylmethoxy) benzoic acid;
4'-(4-Carboxy-3-hydroxy-phenoxymethyl)biphenyl-4-carboxylic acid;
2-Hydroxy-4-(3',4'-dimethoxy-biphenyl-4-ylmethoxy)-benzoic acid;
Biphenyl-4-carboxylic acid 4-carboxy-3-hydroxy-phenyl ester;
4-(Biphenyl-2-ylmethoxy)-2-hydroxy-benzoic acid;
4-[3',4'-(Methylenedioxy)-biphenyl-3-ylmethoxy]-2-hydroxy-benzoic acid;
2,2,2-Trifluoro-N-[4-(4-fluoro-benzyloxy)-2-hydroxy-phenyl]-acetamide;
4-(2'-Cyano-biphenyl-4-ylmethoxy)-2-hydroxy-benzoic acid;
4-(4-Fluoro-benzyloxy)-2-hydroxy-benzoic acid;
4-(4-Acetylamino-benzylamino)-2-hydroxy-benzoic acid;
4-(4-Difluoromethoxy-benzylamino)-2-hydroxy-benzoic acid;
2-Hydroxy-4-(3-nitro-benzylamino)-benzoic acid;
2-Hydroxy-5-(4-nitro-phenylazo)-benzoic acid;
4-(3-Bromo-benzyloxy)-2-hydroxy-benzoic acid;
4-(4-Bromo-benzyloxy)-2-hydroxy-benzoic acid;
2-Hydroxy-4-[2-(2-methoxy-ethoxy]-ethoxy]-benzoic acid;
4-But-3-enyloxy-2-hydroxy-benzoic acid;
4-(Biphenyl-4-ylmethoxy)-2-hydroxy-benzoic acid; or
4-(4-Benzoyl-benzyloxy)-2-hydroxy benzoic acid;
  or a pharmaceutically-acceptable addition salt thereof.

In an eleventh preferred embodiment the compound of the invention is a compound of Formula II, wherein $R^4$ represents a 5- or 6-membered monocyclic heteroaryl, heteroaryl-alkyl or heteroaryl-aryl-alkyl group, which heteroaryl groups are selected from furanyl, particular 2- or 3-furanyl; thienyl, in particular 2-thienyl; pyridinyl, in particular 2-, 3- or 4-pyridinyl; isoxazolyl, in particular 3-, 4- or 5-isoxazolyl; pyrazolyl, in particular 1-, 3- or 4-pyrazolyl; in particular [1,2,3]triazolyl or [1,2,4]triazolyl; which heteroaryl groups may optionally be substituted once or twice with substituents selected from the group consisting of halo, alkyl, cycloalkyl, cycloalkyl-alkyl, alkoxy, cycloalkoxy, nitro, amino, carboxy, alkyl-carbonyl, alkyloxalyl-amino, alkoxyoxalyl-amino, alkoxy-carbonyl, carbamoyl, methylenedioxy and phenyl.

In a twelfth preferred embodiment the compound of the invention is a compound of Formula II, wherein $R^4$ represents 2-furanyl, 3-furanyl, 2-(5-acetyl)-thienyl, 3-pyridinyl, 3-(4-methoxy)-pyridinyl, 4-pyridinyl or 4-[1,2,4]triazolyl.

In a most preferred embodiment the compound of the invention is
2-Hydroxy-4-(4-[1,2,4]triazol-1-yl-benzyloxy)-benzoic acid;
2-Hydroxy-4-(4-pyridin-3-yl-benzyloxy)-benzoic acid;
2-Hydroxy-4-(4-pyridin-4-yl-benzyloxy)-benzoic acid;
2-Hydroxy-4-[4-(4-methoxy-pyridin-3-yl)-benzyloxy]-benzoic acid;
4-(4-Furan-3-yl-benzyloxy)-2-hydroxy-benzoic acid;
4-[4-(5-Acetyl-thiophen-2-yl)-benzyloxy]-2-hydroxy-benzoic acid;
4-(4-Furan-2-yl-benzyloxy)-2-hydroxy-benzoic acid; or
2-Hydroxy-4-(3,5-dimethyl-isoxazol-4-yl-methyloxy)-benzoic acid;
  or a pharmaceutically-acceptable addition salt thereof.

In a thirteenth preferred embodiment the compound of the invention is a compound of Formula II, wherein $R^4$ represents a bicyclic heteroaryl group selected from the group consisting of benzo[b]furanyl, in particular 2-, 5- or 6-benzofuranyl; benzo[b]thienyl, in particular 2-, 5- or 6-benzothienyl; benzimidazolyl, in particular 2-, 5- or 6-benzoimidazolyl; quinolinyl, in particular 2-, 3-, 6- or 7-quinolinyl; isoquinolinyl, in particular 3-, 6- or 7-isoquinolinyl; and cinnolinyl, in particular 6- or 7-cinnolinyl; which bicyclic heteroaryl group may optionally be substituted once or twice with substituents selected from the group consisting of halo, alkyl, cycloalkyl, cycloalkyl-alkyl, alkoxy, cycloalkoxy, nitro, amino, carboxy, alkyl-carbonyl, alkyloxalyl-amino, alkoxyoxalyl-amino, alkoxy-carbonyl, carbamoyl, methylenedioxy and phenyl.

In a fourteenth preferred embodiment the compound of the invention is a compound of Formula II, wherein $R^4$ is 2-quinolinyl.

In a most preferred embodiment the compound of the invention is
2-Hydroxy-4-(quinolin-2-ylmethoxy)-benzoic acid;
  or a pharmaceutically-acceptable addition salt thereof.

Finally any combination of two or more of the embodiments described herein is considered within the scope of the present invention.

DEFINITION OF SUBSTITUENTS

In the context of this invention halo represents fluoro, chloro, bromo or iodo.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to ten carbon atoms ($C_{1-10}$-alkyl), including decyl and nonyl, even more preferred of from one to eight carbon atoms ($C_{1-8}$alkyl), including octyl, heptyl, hexyl and pentyl. In a preferred embodiment alkyl represents a $C_{1-4}$-alkyl group, including butyl, isobutyl, secondary butyl, and tertiary butyl.

In the context of this invention a haloalkyl group designates an alkyl group as defined herein, which alkyl group is substituted one or more times with halo. Preferred haloalkyl groups of the invention include dihalomethyl and trihalomethyl, in particular difluoromethyl and trifluoromethyl.

In the context of this invention a hydroxyalkyl group designates an alkyl group as defined above, which alkyl group is substituted one or more times with hydroxy. Preferred monohydroxyalkyl groups of the invention include methanol and 2-ethanol, and preferred dihydroxyalkyl groups of the invention include 2,3-dihydroxy-propyl, 7,7-dihydroxy-octyl and 7,8-dihydroxy-propyl.

In the context of this invention an alkenyl group designates a straight or branched carbon chain containing one or more double bonds, including di-enes, tri-enes and poly-enes. In a preferred embodiment the alkenyl group of the invention comprises of from two to ten carbon atoms ($C_{2-10}$alkenyl), more preferred of from two to eight atoms ($C_{2-8}$alkenyl), including at least one double bond. In a most preferred embodiment the alkenyl group of the invention is ethenyl; 1- or 2-propenyl (allyl); 1-, 2- or 3-butenyl, or 1,3-butdienyl; 1-, 2-, 3-, 4- or 5-hexenyl, or 1,3-hexdienyl, or 1,3,5-hextrienyl; 1-, 2-, 3-, 4-, 5-, 6-, or 7-octenyl, or 1,3-octdienyl, or 2,6-octdienyl, or 1,3,5-octtrienyl, 1,3,5,7-octtetraenyl or 3,7-dimethyl-octa-2,6-dienyl.

In the context of this invention an alkynyl group designates a carbon chain containing one or more triple bonds, including di-ynes, tri-ynes and poly-ynes. In a preferred embodiment the alkynyl group of the invention comprises of from two to ten carbon atoms ($C_{2-10}$-alkynyl), more preferred of from two to eight carbon atoms ($C_{2-8}$-alkynyl), including at least one triple bond. In is most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4, or 5-hexynyl, or 1,3-hexdiynyl or 1,3,5-hextriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5-octtriynyl, or 1,3,5,7-octtetraynyl.

In the context of this invention a cycloalkyl group designates a cyclic alkyl group, preferably containing of from three to ten carbon atoms ($C_{3-10}$-cycloalkyl), including cyclopropyl, cyclobutyl, cyclopentyl, cyclohexyl, cycloheptyl and cyclooctyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkyl-cycloalkyl group designates an alkyl group as defined above, which alkyl group is substituted on a cycloalkyl group as also defined above. Examples of preferred alkyl-cycloalkyl groups of the invention include methylcyclohexyl and ethylcyclohexyl.

In the context of this invention an alkyl-cycloalkyl-alkyl group designates an alkyl group as defined above, which alkyl group is substituted on a cycloalkyl group as also defined above, which cycloalkyl group is substituted on another alkyl group as defined above. Examples of preferred alkyl-cycloalkyl-alkyl groups of the invention include methylcyclopropylmethyl, ethylcyclopropylmethyl, ethylcyclopropylethyl and ethylcyclopropylethyl.

In the context of this invention an alkoxy group designates an "alkyl-O—" group, wherein alkyl is as defined above. Examples of preferred alkoxy groups of the invention include methoxy and ethoxy.

In the context of this invention an alkoxy-alkyl group designates an "alkyl-O-alkyl-" group, wherein alkyl is as defined above. Examples of preferred alkoxy-alkyl groups of the invention include methoxy-methyl, ethoxy-methyl, methoxy-ethyl and ethoxy-ethyl.

In the context of this invention an alkoxy-alkoxy-alkyl group designates an "alkyl-O-alkyl-O-alkyl-" group, wherein alkyl is as defined above. Examples of preferred alkoxy-alkoxy-alkyl groups of the invention include methoxy-methoxy-methyl, ethoxy-methoxy-methyl, methoxy-methoxy-ethyl, ethoxy-methoxy-ethyl, methoxy-ethoxy-methyl, ethoxy-ethoxy-methyl, methoxy-ethoxy-ethyl and ethoxy-ethoxy-ethyl.

In the context of this invention a haloalkoxy group designates an alkyl group as defined herein, which alkyl group is substituted one or more times with halo. Preferred haloalkoxy groups of the invention include dihalomethoxy and trihalomethyl, in particular difluoromethoxy and trifluoromethoxy.

In the context of this invention a cycloalkoxy group designates a "cycloalkyl-O—" group, wherein cycloalkyl is as defined above.

In the context of this invention a cycloalkoxy-alkyl group designates a "cycloalkyl-O-alkyl-" group, wherein cycloalkyl and alkyl are as defined above.

In the context of this invention a cycloalkoxy-alkoxy-alkyl group designates a "cycloalkyl-O-alkyl-O-alkyl-" group, wherein cycloalkyl and alkyl are as defined above.

In the context of this invention a cycloalkoxy-cycloalkyl group designates a "cycloalkyl-O-cycloalkyl-" group, wherein cycloalkyl is as defined above.

In the context of this invention a cycloalkyl-alkoxy group designates a "cycloalkyl-alkyl-O-" group, wherein alkyl and cycloalkyl are as defined above.

In the context of this invention a cycloalkoxy-cycloalkoxy group designates a "cycloalkyl-O-cycloalkyl-" group, wherein cycloalkyl is as defined above.

In the context of this invention an amino group may be a primary (—NH$_2$), secondary (—NH-alkyl), or tertiary (—N(alkyl)$_2$) amino group, i.e. it may be substituted once or twice with an alkyl group as defined above (i.e. N-alkyl-amino or N,N-dialkyl-amino). Preferred amino groups of the invention are primary amino groups.

In the context of this invention an N-(alkyl-carbonyl)amino group designates a secondary amino group N-substituted with an alkylcarbonyl group as defined below. A preferred N-(alkyl-carbonyl)amino group of the invention is acetylamino.

In the context of this invention an N,N-di(alkyl-carbonyl) amino group designates a tertiary amino group N,N-di-substituted with two alkylcarbonyl groups as defined below. A preferred N,N-di(alkyl-carbonyl)amino group of the invention is diacetylamino.

In the context of this invention an acyl group designates a carboxy group (—COOH) or an alkyl-carbonyl group (alkyl-CO—), wherein alkyl is as defined above. Examples of preferred acyl groups of the invention include carboxy, acetyl, and propionyl.

In the context of this invention an alkyl-carbonyl group designates an "alkyl-CO—" group, wherein alkyl is as defined above.

In the context of this invention an alkoxy-carbonyl group designates an "alkyl-O—CO—" group, wherein alkyl is as defined above.

In the context of this invention an N-alkyl-carbamoyl group designates a "alkyl-NH—CO)—" group, and an N,N-dialkyl-sulfamoyl group designates a "N,N-di-alkyl-N—(CO)—" group, wherein alkyl is as defined above.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl. In a most preferred embodiment an aryl group of the invention is phenyl.

In the context of this invention an aryloxy group designates a "aryl-O—" group, wherein aryl is as defined above. Examples of preferred aryloxy groups of the invention include phenoxy and naphthoxy.

In the context of this invention a biaryl group designates a "aryl-aryl-" group, wherein aryl is as defined above. A preferred biaryl group of the invention is biphenyl.

In the context of this invention an aryl-alkyl (aralkyl) group designates an aryl group as defined above, which aryl group is attached to an alkyl group as also defined above. A preferred aryl-alkyl group of the invention is benzyl.

In the context of this invention an aryl-aryl-alkyl group designates an aryl group, which aryl group is attached to another aryl group, which aryl group again is attached to an alkyl group, wherein aryl and alkyl are as defined above. Examples of preferred aryl-aryl-alkyl groups of the invention include 4-(4-biphenyl)-benzyl.

In the context of this invention an aryl-carbonyl group designates an aryl group, which aryl group is attached to a carbonyl group, aryl is as defined above. Examples of preferred aryl-carbonyl groups of the invention include benzoyl.

In the context of this invention an aryl-carbonyl-aryl group designates an aryl group, which aryl group is attached to a carbonyl group, which carbonyl group again is attached to an aryl group, wherein aryl is as defined above. Examples of preferred aryl-carbonyl-aryl groups of the invention include benzoyl-phenyl.

In the context of this invention a heteroaryl group designates a mono-, bi- or poly-heterocyclic group, which holds one or more heteroatoms in its ring structure. The term "bi- and poly-heterocyclic groups" includes benzo-fused five- and six-membered heterocyclic rings containing one or more heteroatoms. Preferred heteroatoms include nitrogen (N), oxygen (O), and sulphur (S).

Preferred monocyclic heteroaryl groups of the invention include aromatic 5- and 6-membered heterocyclic monocyclic groups, including furanyl, in particular 2- or 3-furanyl; thienyl, in particular 2- or 3-thienyl; pyrrolyl (azolyl), in particular 2- or 3-pyrrolyl; oxazolyl, in particular oxazol-2-, 4- or 5-yl; imidazolyl, in particular 2- or 4-imidazolyl; pyrazolyl, in particular 1-, 3- or 4-pyrazolyl; isoxazolyl, in particular isoxazol-3-, 4- or 5-yl; pyridinyl, in particular 2-, 3- or 4-pyridinyl; pyridazinyl, in particular 3- or 4-pyridazinyl; pyrimidinyl, in particular 2-, 4- or 5-pyrimidinyl; pyrazinyl, in particular 2- or 3-pyrazinyl; which heteroaryl group may optionally be substituted one or more times with substituents selected from the group consisting of alkyl, cycloalkyl, cycloalkyl-alkyl, alkoxy, cycloalkoxy and phenyl.

Preferred bicyclic heteroaryl groups of the invention include benzo[b]furanyl, in particular 2-, 5- or 6-benzofuranyl; benzo[b]thienyl, in particular 2-, 5- or 6-benzothienyl; benzimidazolyl, in particular 2-, 5- or 6-benzoimidazolyl; quinolinyl, in particular 2-, 3-, 6- or 7-quinolinyl; isoquinolinyl, in particular 3-, 6 or 7-isoquinolinyl; and cinnolinyl, in particular 6- or 7-cinnolinyl; which heteroaryl group may optionally be substituted one or more times with substituents selected from the group consisting of alkyl, cycloalkyl, cycloalkyl-alkyl, alkoxy, cycloalkoxy and phenyl.

In the context of this invention a heteroaryl-alkyl group designates a heteroalkyl group as defined above, substituted on an alkyl group as defined above. Preferred heteroaryl-alkyl groups of the invention include 3-pyridinyl-methyl, 4-pyridinyl-methyl, 4-isoxazolyl-methyl, 2-1H-benzimidazolyl-methyl and 2-quinolinyl-methyl.

In the context of this invention a heteroaryl-aryl group designates a heteroalkyl group as defined above, substituted on an aryl group as defined above. Preferred heteroaryl-aryl groups of the invention include 4-(1-pyrazolyl)-phenyl, 4-(1-[1,2,4]triazolyl)-phenyl, 4-(3-pyridinyl)-phenyl, 4-(4-pyridinyl)-phenyl, 4-(2-furanyl)-phenyl, 4-(3-furanyl)-phenyl and 4-(2-thienyl)-phenyl.

In the context of this invention a heteroaryl-aryl-alkyl group designates a heteroalkyl group as defined above, substituted on an aryl group as defined above, which aryl group is substituted on an alkyl group as defined above. Preferred heteroaryl-aryl-alkyl groups of the invention include 4-(1-pyrazolyl)-benzyl, 4-(1-[1,2,4]triazolyl)-benzyl, 4-(3-pyridinyl)-benzyl, 4-(4-pyridinyl)-benzyl, 4-(2-furanyl)-benzyl, 4-(3-furanyl)-benzyl and 4-(2-thienyl)-benzyl.

In the context of this invention an N-aryl-sulfamoyl group designates a "aryl-NH—(CO)—" group, and an N-heteroaryl-sulfamoyl group designates a "heteroaryl-N—(CO)—" group, wherein aryl and heteroaryl are as defined above. Preferred N-aryl-sulfamoyl groups of the invention include phenylsulfamoyl, and preferred N-heteroaryl-sulfamoyl groups of the invention include 2-pyridinylsulfamoyl and 3-pyridinylsulfamoyl.

In the context of this invention a non-aromatic 5- or 6-membered monocyclic heterocyclic group represents a heterocyclic group selected from pyrrolidinyl, imidazolidinyl, tetrahydropyranyl, pyrazolidinyl, tetrahydropyranyl, piperidinyl, morpholinyl and piperazinyl. Preferred non-aromatic heterocyclic groups of the invention include tetrahydropyranyl and piperidinyl.

In the context of this invention a linking group, if present, is a divalent group linking the substituent $R^4$ with the rest of the molecule. Preferred linking groups of the invention include the poly-methylene groups, in particular methylene, ethylene, propylene and butylidene, and the poly-vinylidene groups, in particular vinylidene, allyl and butenyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic add addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysine, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts (aza-onium salts). Preferred aza-onium salts include the alkyl-onium salts, in particular the methyl- and the ethyl-onium salts; the cycloalkyl-onium salts, in particular the cyclopropyl-onium salts; and the cycloalkylalkyl-onium salts, in particular the cyclopropyl-methyl-onium salts.

Steric Isomers

The chemical compounds of the present invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Preparation

The compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The compounds of the invention have been found useful as modulators of the KCNQ potassium channels. At present five such channels are known, i.e. the KCNQ1 channel, the KCNQ2 channel, the KCNQ3 channel, the KCNQ4 channel, and the KCNQ5 channel, and heteromeric combinations hereof. Moreover, the modulator activity may be inhibitory (i.e. inhibitory activity) or stimulating (i.e. activating activity).

In a preferred embodiment the compound of the invention show stimulating activity at the KCNQ2, KCNQ3, KCNQ4 and/or the KCNQ5 potassium channels, and the heteromeric combinations hereof.

The modulator activity may be determined using conventional methods, e.g. binding or activity studies, known in the art, or as described in the working examples.

Accordingly, the compounds of the invention are useful for treatment, prevention or alleviation of a disease or a disorder or a condition of a living animal body, including a human, which disorder, disease or condition is responsive to modulation of a KCNQ potassium channel.

Due to the distribution of KCNQ channels within the organism, KCNQ channel modulators are considered potentially useful for the treatment or alleviation of conditions as diverse as pain, migraine, tension type headache, PNS disorders, CNS disorders, CNS damage caused by trauma, stroke or neurodegenerative illness or diseases, learning and cognitive disorders, motion and motor disorders, multiple sclerosis, heart failure, cardiomyopathia, cardiac disorders, inflammatory diseases, ophthalmic conditions, progressive hearing loss or tinnitus, obstructive or inflammatory airway diseases, for inducing or maintaining bladder control including the treatment or prevention of urinary incontinence.

In a preferred embodiment the compounds of the invention are useful for treatment, prevention or alleviation of a disease, disorder or adverse condition of the CNS. In a more specific embodiment, the disease, disorder or condition is an affective disorder, a neuro-physiological disorder, anxiety, depression, a bipolar disorder, mania, a sleep disorder, addiction, an eating disorder, a phobia, Parkinson's disease, a mood disorder, a psychotic disorder, a compulsive behaviour, mania, psychosis or schizophrenia.

In another preferred embodiment the compounds of the invention are useful for treatment, prevention or alleviation of a CNS damage caused by trauma or by a spinal cord damage, stroke, a neurodegenerative illness or disease, dementia, Alzheimer's disease, a motor neuron disease, a Parkinson-like motor disorder, multiple sclerosis, amyelotrophic lateral sclerosis (ALS), HIV dementia, Huntington's disease, Pick's disease, torsades de pointes, tremor, muscle spasms, myasthenia gravis, convulsions, ataxia, myokymia, seizures, epilepsy or spasticity.

In a third preferred embodiment the compounds of the invention are useful for treatment, prevention or alleviation of pain, including acute and chronic pain, neuropathic pain, central pain, or pain related to diabetic neuropathy, to postherpetic neuralgia, to peripheral nerve injury or drug addiction, migraine and migraine-related disorders and to tension-type headache. In a more specific embodiment the pain is somatic pain, incl. visceral pain or cutaneous pain, or pain caused by inflammation or by infection. In another specific embodiment the pain is neuropathic, e.g. caused by injury to the central or peripheral nervous system, e.g. due to tissue trauma, infection, diabetes, an autoimmune disease, arthritis or neuralgia.

In a fourth preferred embodiment the compounds of the invention are useful for treatment, prevention or alleviation of a learning and cognitive disorder, memory dysfunction, memory impairment or age-associated memory loss.

In a fifth preferred embodiment the compounds of the invention are useful for treatment, prevention or alleviation of a disease, disorder or condition associated with the heart or skeletal muscle, heart failure, cardiomyopathia, cardiac arrhythmia, cardiac ischaemia or long QT syndrome.

In a sixth preferred embodiment the compounds of the invention are useful for treatment, prevention or alleviation of an inflammatory disease or condition, inflammatory bowel disease, Crohn's disease, ulcerative colitis or Creutzfeld-Jacobs disease.

In a seventh preferred embodiment the compounds of the invention are useful for treatment, prevention or alleviation of asthma, an obstructive or inflammatory airway disease, an airway hyper reactivity, a pneumoconiosis such as aluminosis, anthracosis, asbestosis, chalicosis, ptilosis, siderosis, silicosis, tabacosis and byssinosis, a chronic obstructive pulmonary disease (COPD), excerbation of airways hyper reactivity or cystic fibrosis.

In an eight preferred embodiment the compounds of the invention are useful for treatment, prevention or alleviation of progressive hearing loss or tinnitus, an ophthalmic disorder, a drug-dependence or drug-addiction disorder, hyperactive gastric motility or urinary incontinence.

Pharmaceutical Compositions

Viewed from one aspect the invention relates to the use of a compound of the invention, or a pharmaceutically-acceptable addition salt thereof, for the manufacture of a pharmaceutical composition for the treatment, prevention or alleviation of a disease or a disorder or a condition of a mammal, including a human, which disease, disorder or condition is responsive to modulation of KCNQ channels.

Viewed from another aspect, the invention provides pharmaceutical compositions comprising a therapeutically-effective amount of a compound of the invention, or a pharmaceutically-acceptable addition salt thereof, together with at least one pharmaceutically-acceptable carrier or diluent, for the treatment, prevention or alleviation of a disease or a disorder or a condition that is responsive to modulation of KCNQ channels.

While a compound for use according to the invention may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising a compound of the invention, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route which suite the desired therapy. Preferred routes of administration include oral administration, in particular in tablet, in capsule, in drags, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of KCNQ channels, and which method comprises administering to such a living animal body, including a human, in need thereof an effective amount of a compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

The compounds of the present invention can be prepared using readily available starting materials or known intermediates.

The salicylic acids shown in Table 1 may be prepared by reacting a 2,4-dihydroxy benzoic acid ester with e.g. a halide and succeeding de-esterification in alkaline solution (see Scheme 1). Alternatively a 2-halo-4-hydroxy benzoic acid ester (see Scheme 1; X=OH, Cl, F, Br) may be used to yield 2-halo-4-alkyloxy benzoic acids. General and specific procedures for preparation of the present compounds are provided in the examples below.

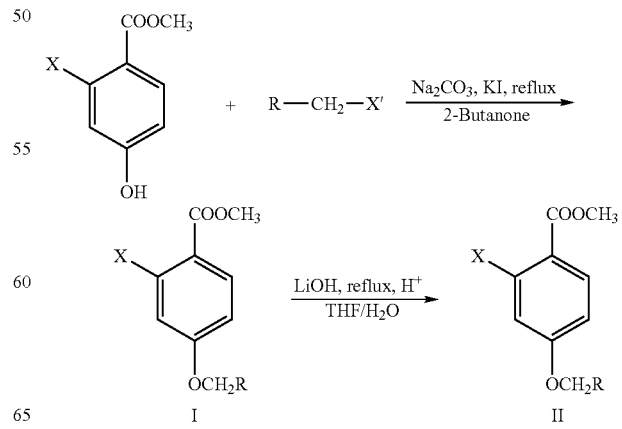

General Method for the Preparation of Compounds of Type II

2-Hydroxy-4-(3,5-dimethyl-isoxazol-4-yl-methyloxy)-benzoic acid (Compound 1-1)

Methyl-2,4-dihydroxy benzoate (259 mg; 1.54 mmol) and 4-(chloromethyl)-3,5-dimethyl-isoxazole (0.17 mL; 1.37 mmol) was dissolved in dry 2-butanone (10 mL). To the clear solution was added $Na_2CO_3$ (196 mmol; 1.80 mmol), and a catalytic amount of KI. The slurry was then refluxed for 24 hours and evaporated to dryness. The remainder was dissolved in 2 mL THF/4 mL $H_2O$ and LiOH (250 mg; 10 mmol) added. The resulting slurry was refluxed for 72 hours, acidified using 4 M HCl (aq.) and extracted with EtOAc/PE35-50° C. (5:1). A precipitate formed in the organic layer, which was filtered and washed with EtOAc/PE80-100° C. (1:1) yielding, after drying, 300 mg (83%) of a pure white solid. Mp. 201-203° C.; MS (ESI−): 262 (MH−).

Additional compounds were synthesized in a similar manner (see Table 1).

TABLE 1

| Entry | Chemical Structure | Chemical Name | Physical data |
|---|---|---|---|
| 1-1 | 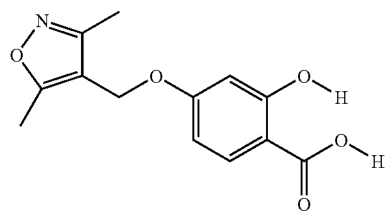 | 2-Hydroxy-4-(3,5-dimethyl-isoxazol-4-yl-methyloxy)-benzoic acid | Mp. = 201-203° C., MS (ESI−): 262 (MH−) |
| 1-2 | 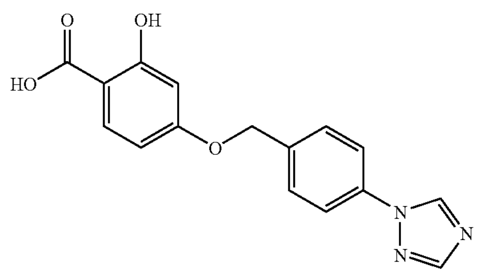 | 2-Hydroxy-4-(4-[1,2,4]triazol-1-yl-benzyloxy)-benzoic acid | Mp. = 229° C. (decomposes), MS (ESI−): 310 (MH−) |
| 1-3 | 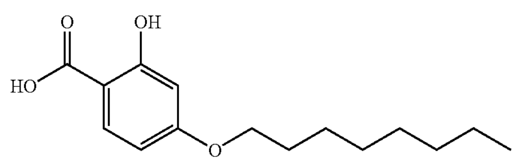 | 2-Hydroxy-4-octyloxy-benzoic acid | Mp. = 100-102° C., MS (ESI−): 265 (MH−) |
| 1-4 | 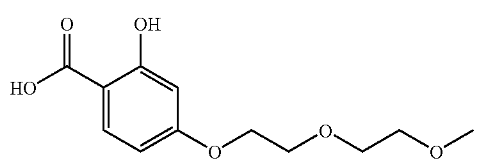 | 2-Hydroxy-4-[2-(2-methoxy-ethoxy)-ethoxy]-benzoic acid | Mp. = 110-112° C., MS (ESI−): 255 (MH−) |
| 1-5 | 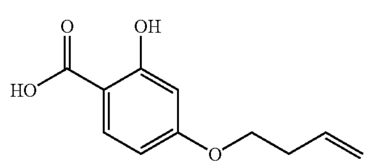 | 4-But-3-enyloxy-2-hydroxy-benzoic acid | Mp. = 143-144° C., MS (ESI−): 207 (MH−) |
| 1-6 | 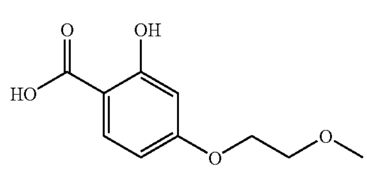 | 2-Hydroxy-4-(2-methoxy-ethoxy)-benzoic acid | Mp. = 127-128° C., MS (ESI−): 221 (MH−) |

TABLE 1-continued

| Entry | Chemical Structure | Chemical Name | Physical data |
|---|---|---|---|
| 1-7 | 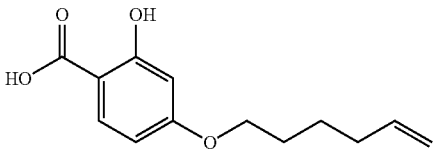 | 4-Hex-5-enyloxy-2-hydroxy-benzoic acid | Mp. = 105° C., MS (ESI–): 235 (MH⁻) |
| 1-8 | 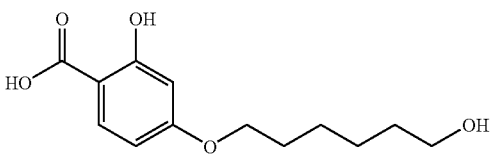 | 2-Hydroxy-4-(6-hydroxyhexyloxy) benzoic acid | Mp. = 139° C., MS (ESI–): 253 (M⁻) (MH⁻) |
| 1-9 | 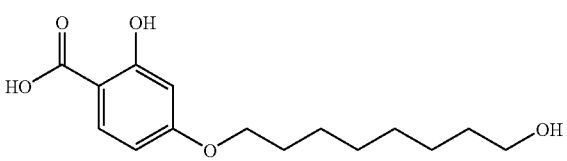 | 2-Hydroxy-4-(8-hydroxy-octyloxy) benzoic acid | Mp. = 119-121° C., MS (ESI–): 281 (M⁻) (MH⁻) |
| 1-10 | 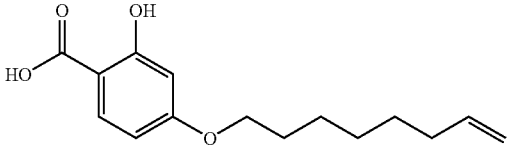 | 2-Hydroxy-4-oct-7-enyloxy-benzoic acid | Mp. = 102-111° C., MS (ESI–): 263 (MH⁻) |
| 1-11 | 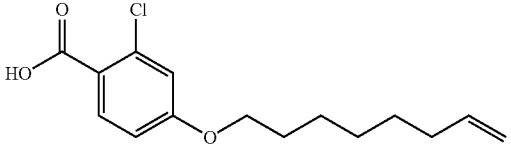 | 2-Chloro-4-oct-7-enyloxy-benzoic acid | MS (ESI–): 281/283 (MH⁻) |
| 1-12 | 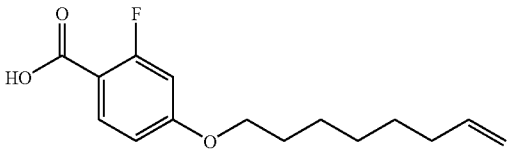 | 2-Fluoro-4-oct-7-enyloxy-benzoic acid | MS (ESI–): 265 (MH⁻) |
| 1-13 | 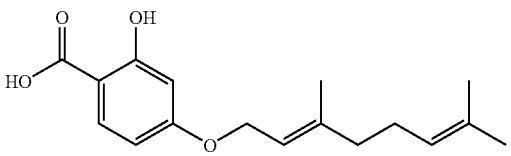 | 4-(3,7-Dimethyl-octa-2,6-dienyloxy)-2-hydroxy-benzoic acid | Mp. = 97-106° C., MS (ESI–): 289 (MH⁻) |
| 1-14 | 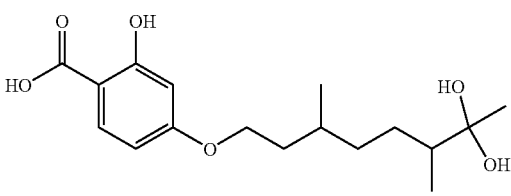 | 4-(7,7-Dihydroxy-3,6-dimethyl-octyloxy)-2-hydroxy benzoic acid | MS (ESI–): 325 (MH⁻) |
| 1-15 | 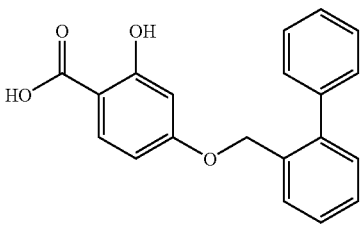 | 4-(Biphenyl-2-yl-methoxy)-2-hydroxy-benzoic acid | MS (ESI–): 319 (MH⁻) |

TABLE 1-continued

| Entry | Chemical Structure | Chemical Name | Physical data |
|---|---|---|---|
| 1-16 | 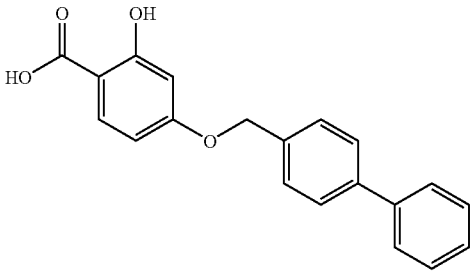 | 4-(Biphenyl-4-yl-methoxy)-2-hydroxy-benzoic acid | Mp. = 216-219° C. (decomposes); MS (ESI−): 319 (MH−) |
| 1-17 | 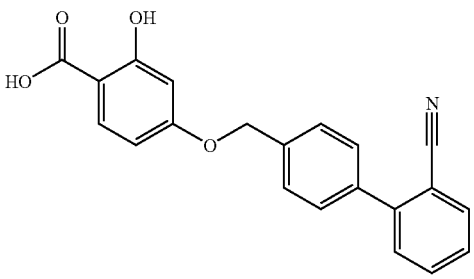 | 4-(2'-Cyano-biphenyl-4-yl-methoxy)-2-hydroxy-benzoic acid | Mp. = 220° C. (decomposes) |
| 1-18 | 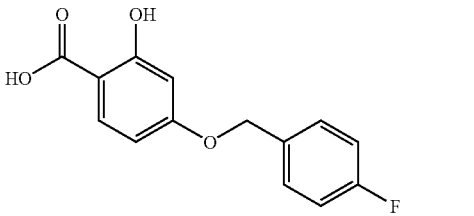 | 4-(4-Fluoro-benzyloxy)-2-hydroxy-benzoic acid | Mp. = 196-198° C. |
| 1-19 | 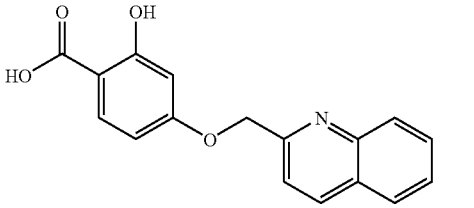 | 2-Hydroxy-4-(quinolin-2-yl-methoxy)-benzoic acid | Mp. = 197° C. (decomposes) |
| 1-20 | 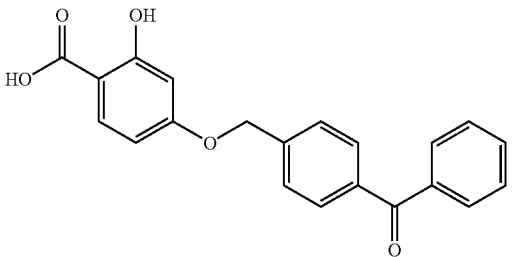 | 4-(4-Benzoyl-benzyl-oxy)-2-hydroxy benzoic acid | Mp. = 198-199° C., MS (ESI−): 347 (MH−) |
| 1-21 | 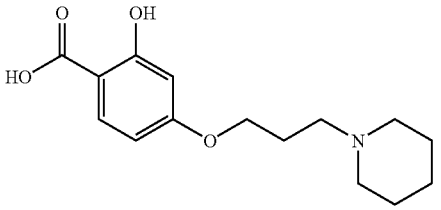 | 2-Hydroxy-4-(3-piperidin-1-yl-propoxy)-benzoic acid | Mp. = 194° C. (decomposes) |

TABLE 1-continued

| Entry | Chemical Structure | Chemical Name | Physical data |
|---|---|---|---|
| 1-22 | 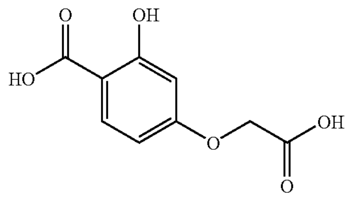 | 4-Carboxymethoxy-2-hydroxy-benzoic acid | MS (ESI–): 211 (MH⁻) |
| 1-23 | 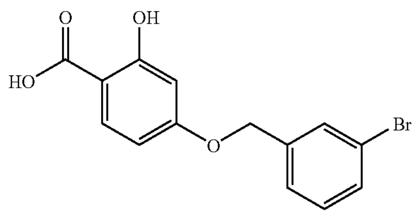 | 4-(3-Bromo-benzyloxy)-2-hydroxy-benzoic acid | Mp. = 191-197° C. |
| 1-24 | 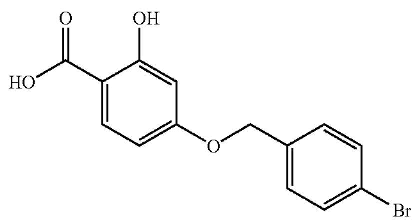 | 4-(4-Bromo-benzyloxy)-2-hydroxy-benzoic acid | |

Compounds of Type I may be further derivatized as shown for the precursor of Compound 1-5 or Compound 1-23 (see Scheme 2a-b, Table 2).

Scheme 2a

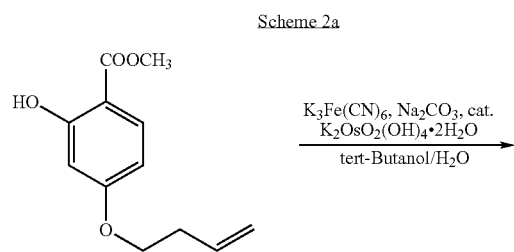

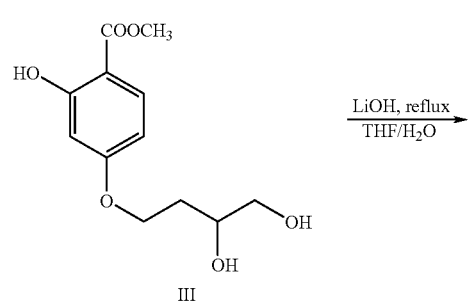

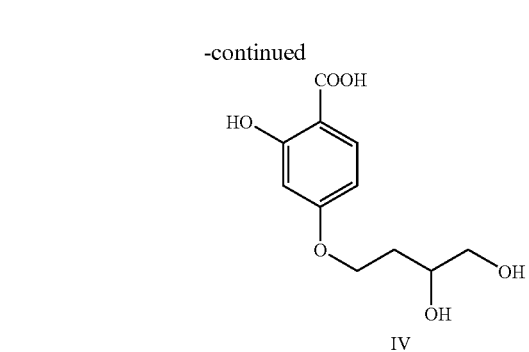

General Method for the Preparation of Compounds of Type IV

Methyl-4-(2,3-dihydroxypropoxy)-2-hydroxy-benzoate

A solution of methyl-4-prop-2-enyloxy-2-hydroxy-benzoic acid ester (850 mg; 4.0 mmol), $K_2Fe(CN)_6$ (3.63 g; 12.4 mmol), $K_2CO_3$ (1.51 g; 12.4 mmol) and $K_2OsO_2(OH)_4 \cdot 2H_2O$ (15 mg; 1 mol %) in tert-butanol (4 mL)/$H_2O$ (4 mL) was stirred vigorously for 18 hours. The mixture was then added $Na_2SO_3$ (615 mg; 4.88 mmol) and stirred for another hour. The aqueous phase was extracted with EtOAc (3×) and the combined organic fractions washed with brine, dried ($Na_2SO_4$), filtered and evaporated to dryness to yield 1.08 g (quantitative yield) of methyl 4-(2,3-dihydroxypropoxy)-2-hydroxy-benzoic acid ester as a solid white compound.

4-(2,3-dihydroxypropoxy)-2-hydroxy-benzoic acid (Compound 2-1)

A slurry of methyl-4-(2,3-dihydroxypropoxy)-2-hydroxy-benzoic acid ester (270 mg; 1.12 mmol) in 10% LiOH in $H_2O$ (w/w; 3.3 mL) and THF (1.15 mL) was refluxed for 2 hours. Additional of 10% LiOH in $H_2O$ (1 mL; w/w) was added and the mixture refluxed for another hour. On cooling and acidification using 1 M HCl (aq) a precipitate formed which was filtered off and dried to yield 181 mg (66%) of a white solid. Mp. 151-153° C.; MS (ESI−): 227 (MH−).

In analogy herewith compounds 2-2 to 2-6 were made (see Table 2).

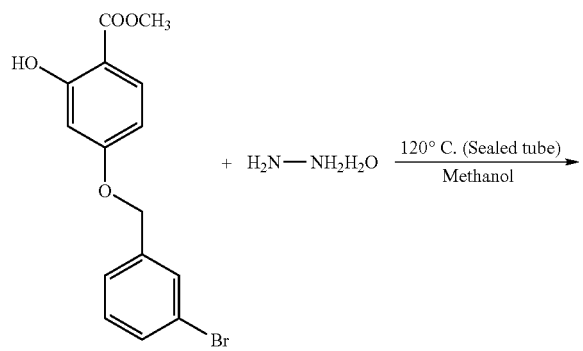

Scheme 2b

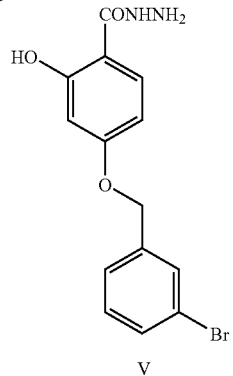

V

General Method for the Preparation of Compounds of Type V 4-(3-Bromo-benzyloxy)-2-hydroxy-benzoic acid hydrazide (Compound 2-7)

A slurry of 4-(3-bromo-benzyloxy)-2-hydroxy-benzoic acid (2.15 g; 6.4 mmol) in MeOH (10 mL) was added hydrazine hydrate (3 mL; 62 mmol) and heated to 120° C. in a sealed metal cylinder for 40 min. The cylinder was cooled on ice and the slurry diluted with THF in order to dissolve precipitate. The clear solution was evaporated onto $SiO_2$, and purified by filtration through a plug of Silica gel ($SiO_2$—PE80-100° C./EtOAc=4:1; EtOAc then EtOAc/$CH_2Cl_2$=3:2) to yield after evaporation 0.9 g (42%). The compound was further purified by crystallization from MeOH/THF to yield 350 mg pure product. Mp. 201-203° C.; MS (ESI−): 335/337 (MH−).

TABLE 2

| Entry | Chemical Structure | Chemical Name | Physical data |
| --- | --- | --- | --- |
| 2-1 | 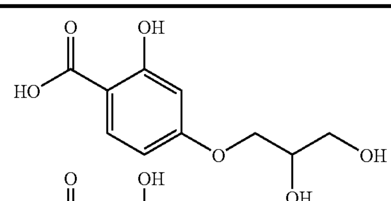 | 4-(2,3-Di-hydroxypropoxy)-2-hydroxy-benzoic acid | Mp. = 151-153° C.; MS (ESI−): 227 (MH−) |
| 2-2 | 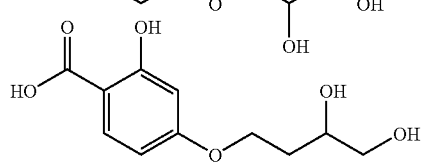 | 4-(3,4-Di-hydroxybutoxy)-2-hydroxy-benzoic acid | Mp. = 140-148° C.; MS (ESI−): 241 (MH−) |
| 2-3 | 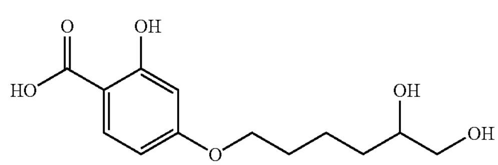 | 4-(5,6-Di-hydroxyhexoxy)-2-hydroxy-benzoic acid | Mp. = 152° C.; MS (ESI−): 269 (MH−) |
| 2-4 | 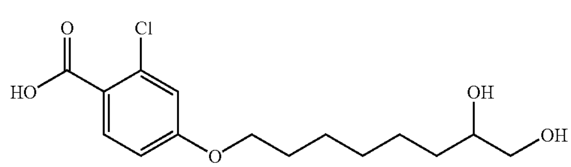 | 2-Chloro-4-(7,8-di-hydroxy-octyloxy)benzoic acid | MS (ESI−): 315/317 (MH−) |

TABLE 2-continued

| Entry | Chemical Structure | Chemical Name | Physical data |
|---|---|---|---|
| 2-5 | 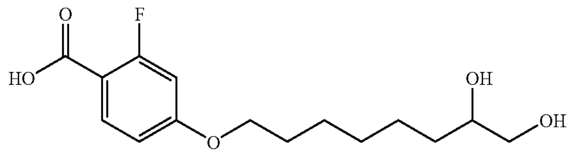 | 2-Fluoro-4-(7,8-di-hydroxy-octyloxy)benzoic acid | MS(ESI−): 299 (MH−) |
| 2-6 | 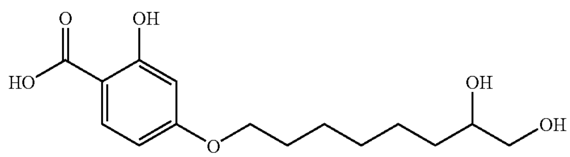 | 4-(7,8-Di-hydroxyoctyloxy)-2-hy-droxy-benzoic acid | Mp. = 168-170° C.; MS(ESI−): 297 (MH−) |
| 2-7 | 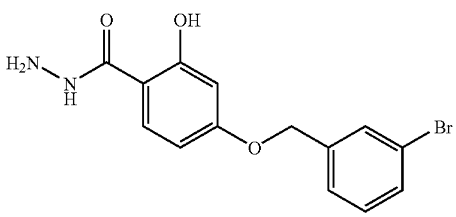 | 4-(3-Bromo-benzyloxy)-2-hy-droxy-benzoic acid hydrazide | Mp. = 201-203° C.; MS (ESI−): 335/335 (MH−) |

The previously described compounds may be further derivatized, e.g. under Suzuki conditions, to give Compounds 3-1 to 3-42 (see Scheme 3, X=any substituent; Table 3).

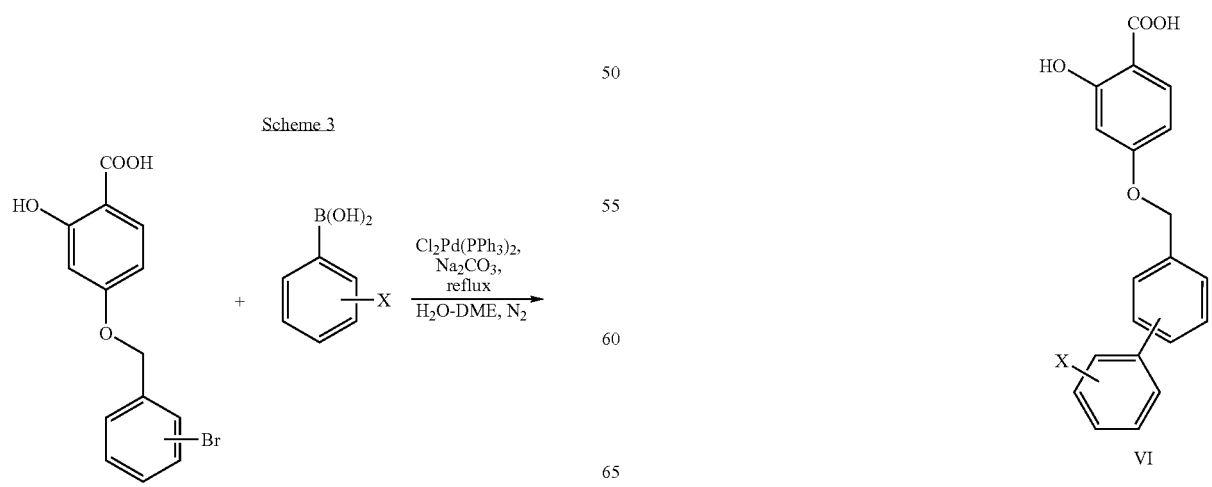

General Method for the Preparation of Compounds of Type VI 4-(3'-Acetyl-biphenyl-4-ylmethoxy)-2-hydroxy-benzoic acid (Compound 3-6)

A mixture of 4-(4-bromo-benzyloxy)-2-hydroxy-benzoic acid (196.3 mg; 0.6075 mmol), 3-acetylbenzene boronic acid (99.7 mg; 0.6080 mmol) and $Na_2CO_3$ (~4 eq.) was dissolved in dimethoxymethane (4 mL) and $H_2O$ (2 mL). The solution was flushed with argon, $Cl_2Pd(PPh_3)_2$ (~2.5 mol %) was added and the mixture stirred under an atmosphere of argon at 100° C. for 16 hours. The resulting black solution was filtered (Gelman Acrodisc GHP, Ø25 mm) and slowly added to a cold 1 M HCl (aq.; 15 mL) solution. The precipitate was filtered off and thoroughly washed with water. Drying in vacuo yielded 195 mg (88%) of a greyish, solid compound with satisfactorily purity. Mp. 215-220° C. (decomposes); MS (ESI-): 361 (MH-)

In analogy herewith compounds of Table 3 were synthesized.

TABLE 3

| Entry | Chemical Structure | Chemical Name | Physical data |
|---|---|---|---|
| 3-1 | 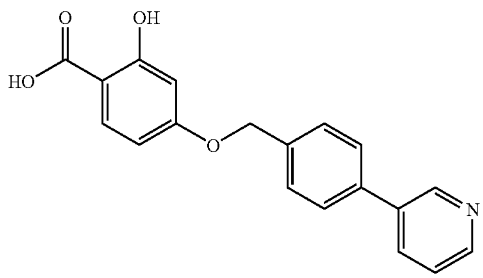 | 2-Hydroxy-4-(4-pyridin-3-yl-benzyloxy)-benzoic acid | Mp. = 209-211° C. (decomposes); MS (ESI-): 320 (MH-) |
| 3-2 | 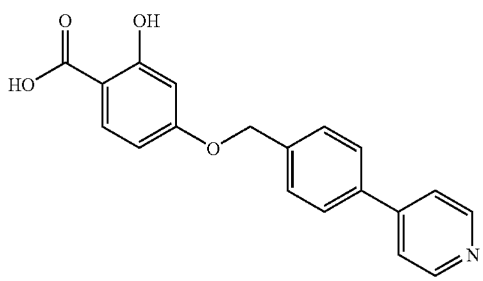 | 2-Hydroxy-4-(4-pyridin-4-yl-benzyloxy)-benzoic acid | Mp. = 252-257° C. (decomposes); MS (ESI-): 320 (MH-) |
| 3-3 | 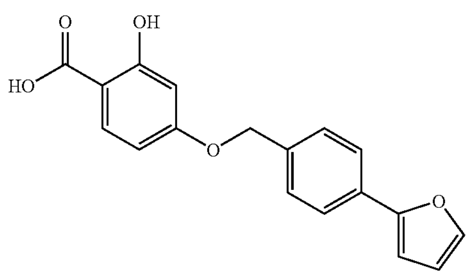 | 4-(4-Furan-2-yl-benzyloxy)-2-hydroxy-benzoic acid | Mp. = 201-205° C. (decomposes); MS (ESI-): 309 (MH-) |
| 3-4 | 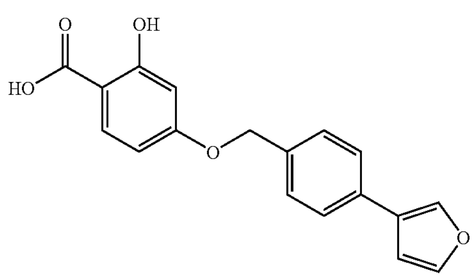 | 4-(4-Furan-3-yl-benzyloxy)-2-hydroxy-benzoic acid | Mp. = 202-206° C. (decomposes); MS (ESI-): 309 (MH-) |

TABLE 3-continued

| Entry | Chemical Structure | Chemical Name | Physical data |
|---|---|---|---|
| 3-5 | 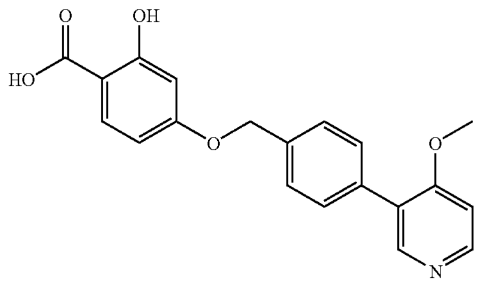 | 2-Hydroxy-4-[4-(4-methoxy-pyridin-3-yl)-benzyloxy]-benzoic acid | Mp. = 197-200° C. (decomposes); MS (ESI−): 350 (MH−) |
| 3-6 | 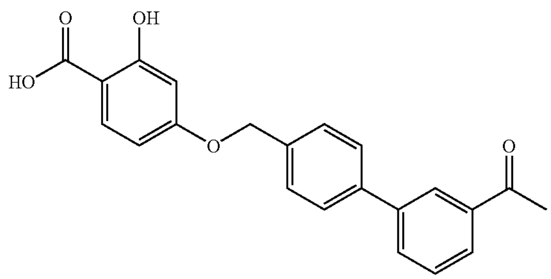 | 4-(3'-Acetyl-biphenyl-4-yl-methoxy)-2-hydroxy-benzoic acid | Mp. = 215-220° C. (decomposes); MS (ESI−): 361 (MH−) |
| 3-7 | 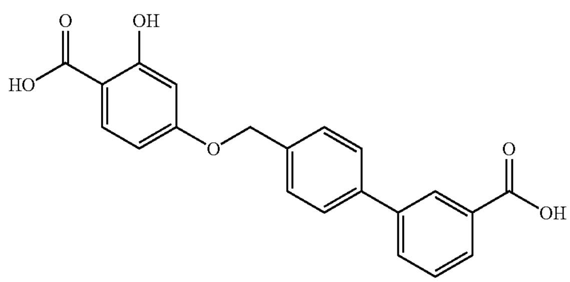 | 4'-(4-Carboxy-3-hydroxy-phenoxymethyl)-biphenyl-3-carboxylic acid | Mp. = 249-255° C. (decomposes); MS (ESI−): 363 (MH−) |
| 3-8 | 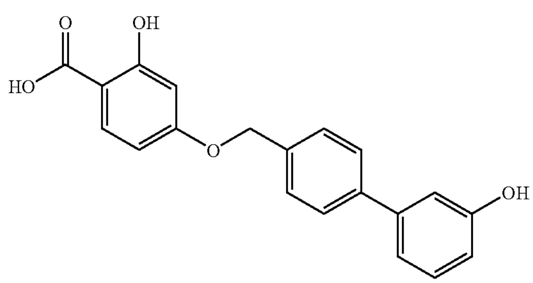 | 2-Hydroxy-4-(3'-hydroxy-biphenyl-4-yl-methoxy)-benzoic acid | Mp. = 209-212° C. (decomposes); MS (ESI−): 335 (MH−) |
| 3-9 | 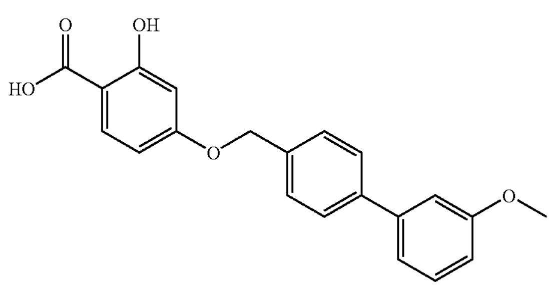 | 2-Hydroxy-4-(3'methoxy-biphenyl-4-yl-methoxy)-benzoic acid | Mp. = 197-199° C. (decomposes); MS (ESI−): 349 (MH−) |

TABLE 3-continued

| Entry | Chemical Structure | Chemical Name | Physical data |
|---|---|---|---|
| 3-10 | 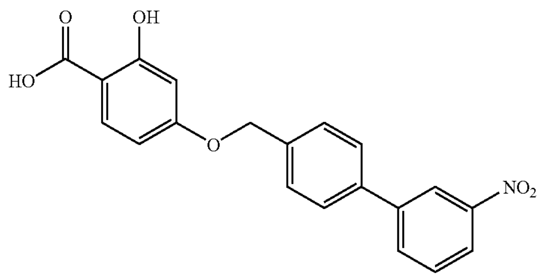 | 2-Hydroxy-4-(3'-nitro-biphenyl-4-yl-methoxy)-benzoic acid | Mp. = 211-214° C. (decomposes); MS (ESI−): 364 (MH−) |
| 3-11 | 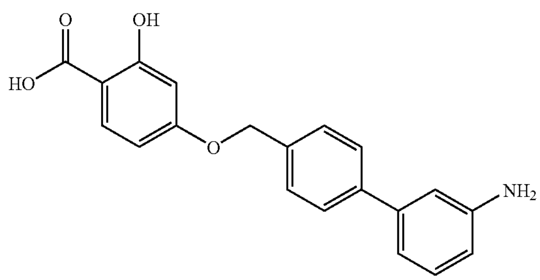 | 4-(3'-Amino-biphenyl-4-yl-methoxy)-2-hydroxy-benzoic acid | Mp. = 207-210° C. (decomposes); MS (ESI−): 334 (MH−) |
| 3-12 | 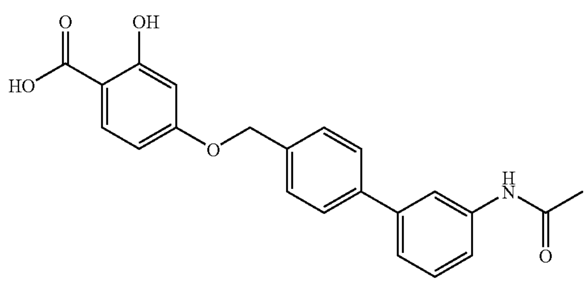 | 4-(3'-Acetylamino-biphenyl-4-yl-methoxy)-2-hydroxy-benzoic acid | Mp. = 231-233° C. (decomposes); MS (ESI−): 376 (MH−) |
| 3-13 | 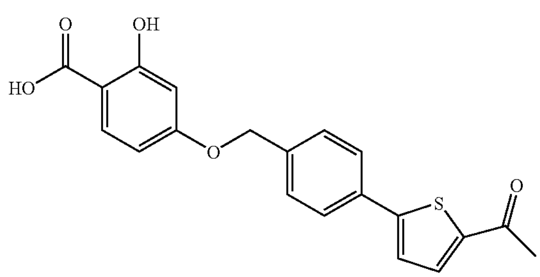 | 4-[4-(5-Acetyl-thiophen-2-yl)-benzyl-oxy]-2-hydroxy-benzoic acid | Mp. = 244-248° C. (decomposes); MS (ESI−): 367 (MH−) |
| 3-14 | 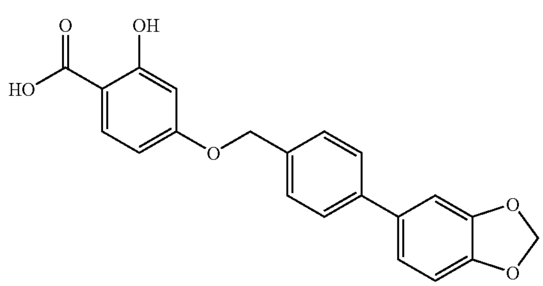 | 4-[3',4'-(Methylenedioxy)-biphenyl-4-yl-methoxy]-2-hydroxy-benzoic acid | Mp. = 222-226° C. (decomposes); MS (ESI−): 363 (MH−) |

TABLE 3-continued

| Entry | Chemical Structure | Chemical Name | Physical data |
|---|---|---|---|
| 3-15 | 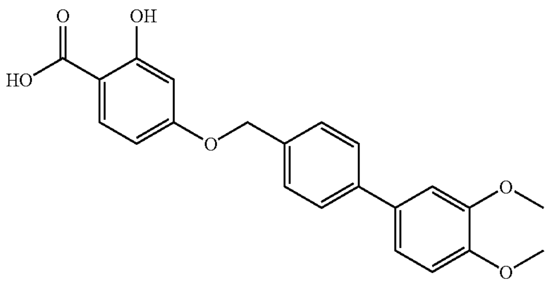 | 2-Hydroxy-4-(3',4'-di-methoxy-biphenyl-4-yl-methoxy)-benzoic acid | Mp. = 200-204° C. (decomposes); MS (ESI−): 379 (MH−) |
| 3-16 | 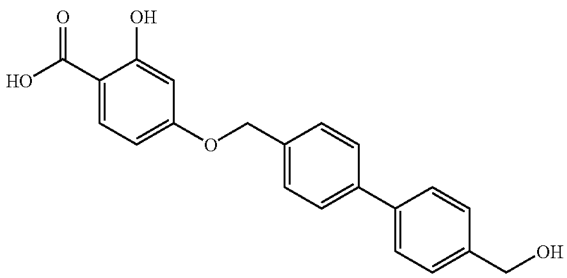 | 2-Hydroxy-4-(4'-hydroxymethyl-biphenyl-4-yl-methoxy)-benzoic acid | Mp. = 222-226° C. (decomposes); MS (ESI−): 349 (MH−) |
| 3-17 | 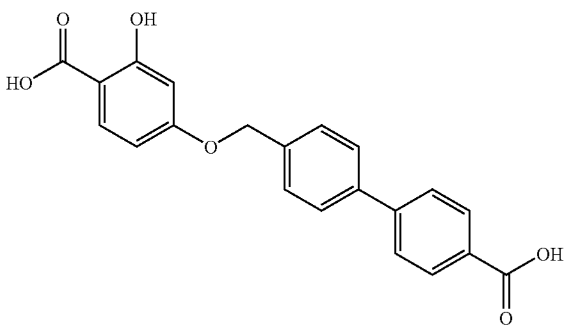 | 4'-(4-Carboxy-3-hydroxy-phenoxymethyl)-biphenyl-4-carboxylic acid | Mp. = 279-284° C. (decomposes); MS (ESI−): 363 (MH−) |
| 3-18 | 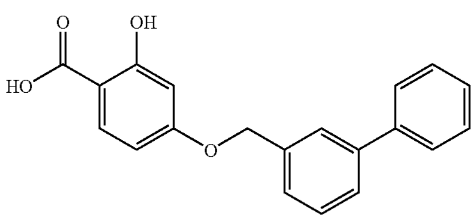 | 4-(Biphenyl-3-yl-methoxy)-2-hydroxy-benzoic acid | Mp. = 184° C. (decomposes); MS (ESI−): 319 (MH−) |
| 3-19 | 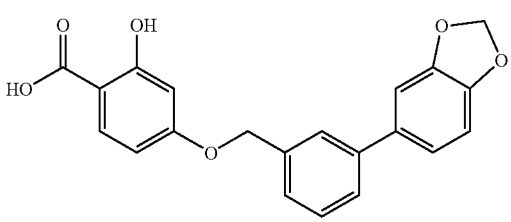 | 4-[3',4'-(Methylenedioxy)-biphenyl-3-yl-methoxy]-2-hydroxy-benzoic acid | Mp. = 195-198° C. (decomposes); MS (ESI−): 363 (MH−) |
| 3-20 | 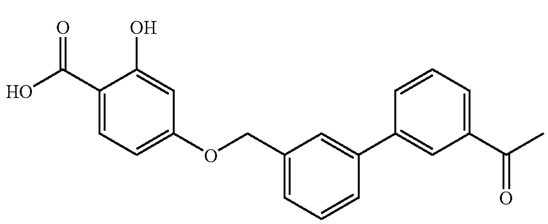 | 4-(3'-Acetyl-biphenyl-3-yl-methoxy)-2-hydroxy-benzoic acid | Mp. = 173-180° C. (decomposes); MS (ESI−): 361 (MH−) |

TABLE 3-continued

| Entry | Chemical Structure | Chemical Name | Physical data |
|---|---|---|---|
| 3-21 | 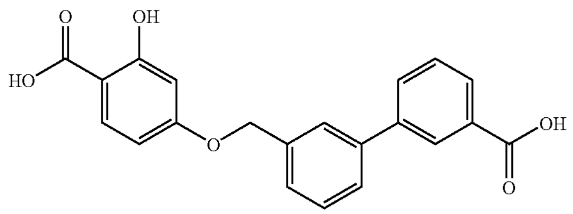 | 3'-(4-Carboxy-3-hydroxy-phenoxy-methyl)-bi-phenyl-3-carboxylic acid | Mp. = 211-227° C. (decomposes); MS (ES−): 363 (MH−) |
| 3-22 | 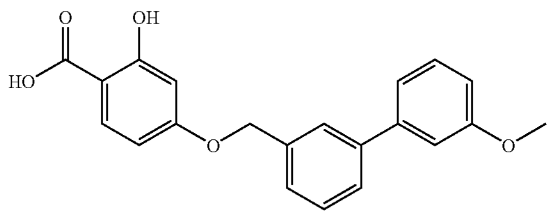 | 2-Hydroxy-4-(3'-methoxy-biphenyl-3-yl-methoxy)-benzoic acid | Mp. = 103-115° C. (decomposes); MS (ESI−): 349 (MH−) |
| 3-23 | 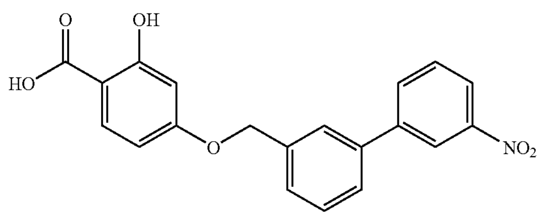 | 2-Hydroxy-4-(3'-nitro-biphenyl-3-yl-methoxy)-benzoic acid | Mp. = 188-193° C. (decomposes); MS (ESI−): 364 (MH−) |
| 3-24 | 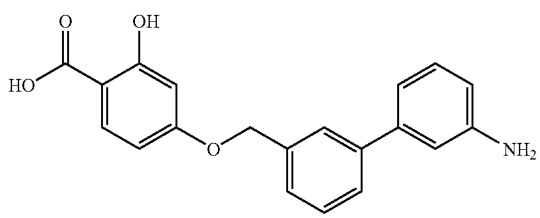 | 4-(3'-Amino-biphenyl-3-yl-methoxy)-2-hydroxy-benzoic acid | Mp. = 205-208° C. (decomposes); MS (ESI−): 334 (MH−) |
| 3-25 | 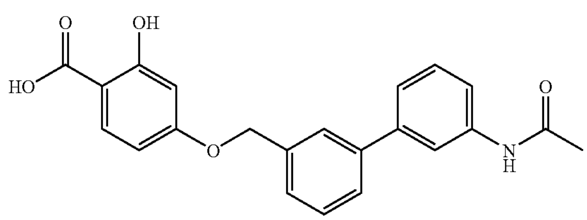 | 4-(3'-Carboxyamino-biphenyl-3-yl-methoxy)-2-hydroxy-benzoic acid | Mp. = 170-172° C. (decomposes); MS (ESI−): 376 (MH−) |
| 3-26 | 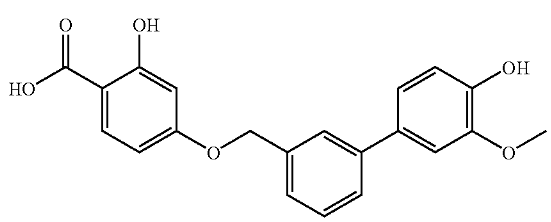 | 2-Hydroxy-4-(4'-hydroxy-3'-methoxy-biphenyl-3-yl-methoxy)-benzoic acid | Mp. = 153-157° C. (decomposes); MS (ESI−): 365 (MH−) |
| 3-27 | 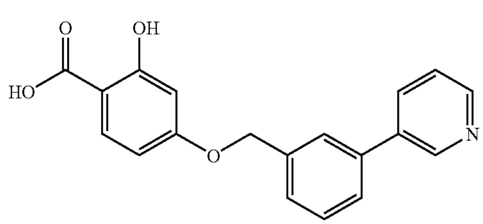 | 2-Hydroxy-4-(3-pyridin-3-yl-benzyloxy)-benzoic acid | Mp. = 189-195° C. (decomposes); MS (ESI−): 320 (MH−) |

TABLE 3-continued

| Entry | Chemical Structure | Chemical Name | Physical data |
|---|---|---|---|
| 3-28 | 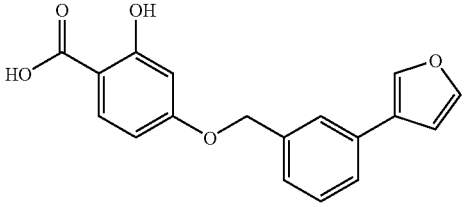 | 4-(3-Furan-3-yl-benzyloxy)-2-hydroxy-benzoic acid | Mp. = 187-190° C. (decomposes); MS (ESI–): 320 (MH–) |
| 3-29 | 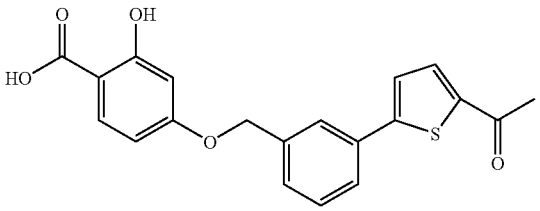 | 4-[3-(5-Acetyl-thiophen-2-yl)-benzyloxy]-2-hydroxy-benzoic acid | Mp. = 210-215° C. (decomposes); MS (ESI–): 367 (MH–) |
| 3-30 | 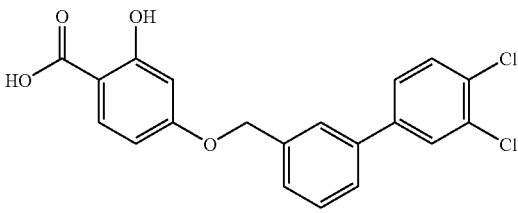 | 4-(3',4'-Dichloro-biphenyl-3-yl-methoxy)-2-hydroxy-benzoic acid | Mp. = 211-215° C. (decomposes); MS (ESI–): 388 (MH–) |
| 3-31 | 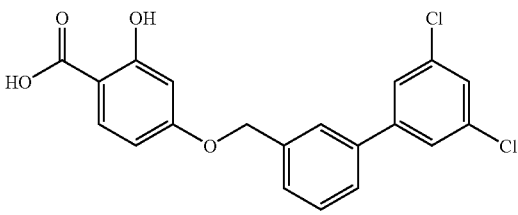 | 4-(3',5'-Dichloro-biphenyl-3-yl-methoxy)-2-hydroxy-benzoic acid | Mp. = 194-197° C. (decomposes); MS (ESI–): 388 (MH–) |
| 3-32 | 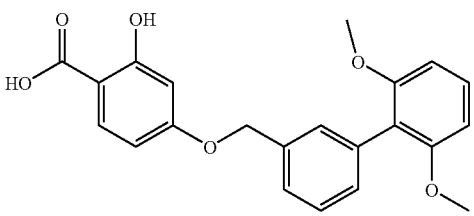 | 4-(2',6'-Dimethoxy-biphenyl-3-yl-methoxy)-2-hydroxy-benzoic acid | MS (ESI–): 379 (MH–) |
| 3-33 | 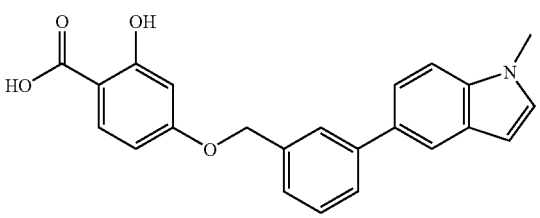 | 2-Hydroxy-4-[3-(1-methyl-1H-indol-5-yl)-benzyloxy]-benzoic acid | Mp. = 181-183° C. (decomposes); MS (ESI–): 372 (MH–) |
| 3-34 | 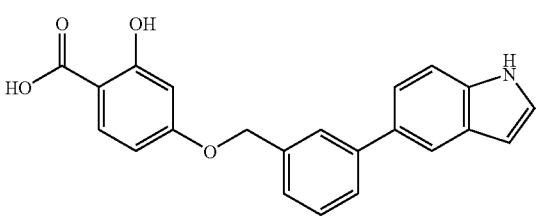 | 2-Hydroxy-4-[3-(1H-indol-5-yl)-benzyloxy]-benzoic acid | Mp. = 193-196° C. (decomposes); MS (ESI–): 358 (MH–) |

TABLE 3-continued

| Entry | Chemical Structure | Chemical Name | Physical data |
|---|---|---|---|
| 3-35 | 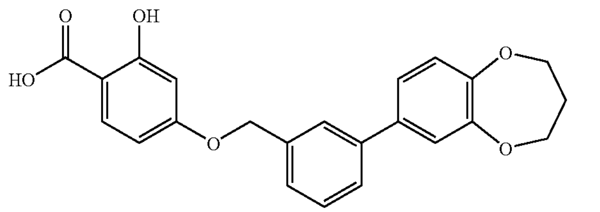 | 4-[3-(3,4-Dihydro-2H-benzo[b][1,4]dioxepin-7-yl)-benzyloxy]-2-hydroxy-benzoic acid | Mp. = 188-192° C. (decomposes); MS (ESI−): 391 (MH−) |
| 3-36 | 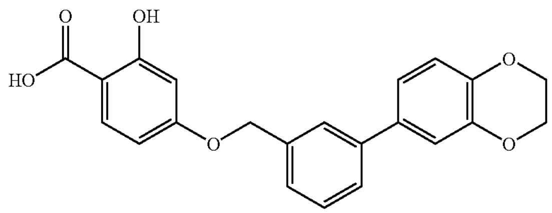 | 4-[3-(2,3-Dihydro-benzo[1,4]dioxin-6-yl)-benzyloxy]-2-hydroxy-benzoic acid | Mp. = 170-175° C. (decomposes); MS (ESI−): 377 (MH−) |
| 3-37 | 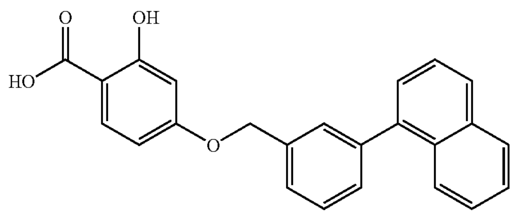 | 2-Hydroxy-4-(3-naphthalen-1-yl-benzyloxy)-benzoic acid | Mp. = 156-164° C. (decomposes); MS (ESI−): 369 (MH−) |
| 3-38 | 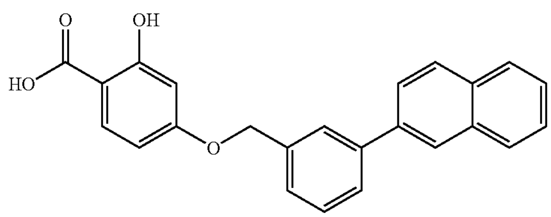 | 2-Hydroxy-4-(3-naphthalen-2-yl-benzyloxy)-benzoic acid | Mp. = 190-194° C. (decomposes); MS (ESI−): 369 (MH−) |
| 3-39 | 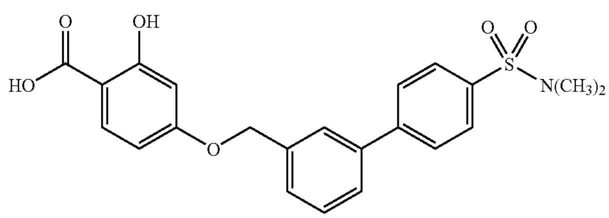 | 4-(4'-Dimethylsulfamoyl-biphenyl-3-yl-methoxy)-2-hydroxy-benzoic acid | Mp. = 196-204° C. (decomposes); MS (ESI−): 426 (MH−) |
| 3-40 | 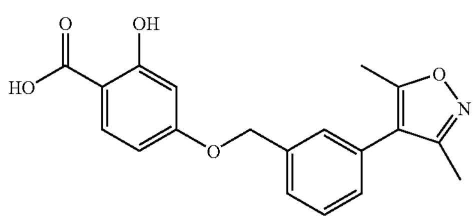 | 4-[3-(3,5-Dimethyl-isoxazol-4-yl)-benzyloxy]-2-hydroxy-benzoic acid | Mp. = 155-176° C. (decomposes); MS (ESI−): 338 (MH−) |
| 3-41 | 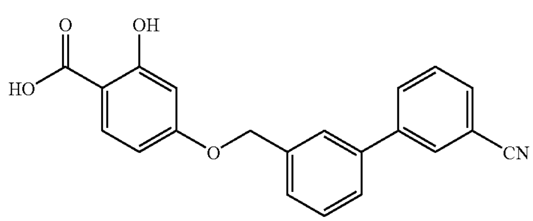 | 4-(3'-Cyano-biphenyl-3-yl-methoxy)-2-hydroxy-benzoic acid | Mp. = 155-170° C. (decomposes); MS (ESI−): 345 (MH−) |

TABLE 3-continued

| Entry | Chemical Structure | Chemical Name | Physical data |
|---|---|---|---|
| 3-42 | 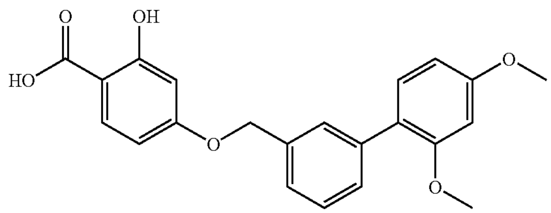 | 4-(2',4'-Dimethoxy-biphenyl-3-yl-methoxy)-2-hydroxy-benzoic acid | Mp. = 176-178° C. (decomposes); MS (ESI−): 379 (MH−) |

As an alternative a Mitsunobu reaction may be performed to yield the alkyl-arylether (see Scheme 4).

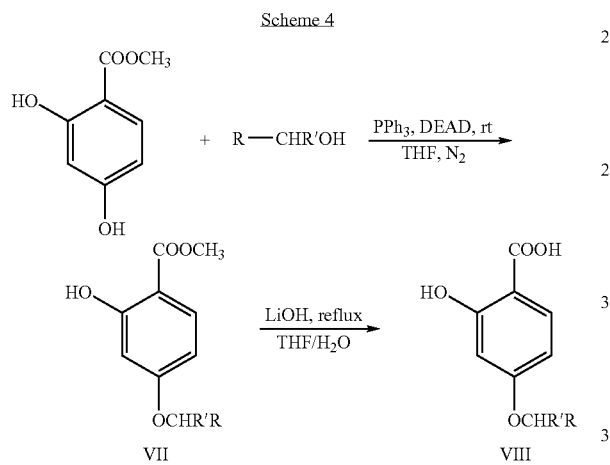

Scheme 4

General Method for the Preparation of Compounds of Type VIII

Methyl-2-hydroxy-4-(tetrahydro-pyran-4-yloxy)-benzoic acid ester

To a cooled (0-5° C.) solution of methyl-2,4-dihydroxy benzoic acid ester (3.36 g; 20 mmol), PPh$_3$ (5.77 g; 22 mmol) and ±tetrahydro-2H-pyran-4-ol (2.1 mL; 22 mmol) in dry THF (20 mL) was added diethyl azodicarboxylate (3.46 mL; 22 mmol) drop-wise over 1 hour. The reaction mixture was allowed to warm to room temperature and stirred for 2 days overnight after which time it was evaporated to a yellow in-homogenous mixture which was diluted with diethyl ether and added PE35-50° C. The precipitate formed was removed by filtration and thoroughly washed with diethyl ether/PE35-50° C. (1:1; 4×). The combined organic fractions were evaporated to an yellow oil which was worked up by column chromatography (SiO$_2$—PE80-100° C./EtOAc=9:1) to yield 2.15 g.

(±)-2-Hydroxy-4-(tetrahydro-pyran-4-yloxy)-benzoic acid (Compound 4-1)

The arylalkylether ester mixture (2.15 g) was dissolved in 2 M LiOH (THF/H$_2$O=1:1; 10 mL+10 mL) and refluxed for 16 hours, acidified, evaporated to dryness and the remainder extracted with EtOAc (2×). The combined organic fractions were filtered through a silicone filter, evaporated to dryness and re-crystallized from 2-propanol/H$_2$O to yield 650 mg (13% overall) of a white solid.

Additional compounds were synthesized in a similar manner (see Table 4).

TABLE 4

| Entry | Chemical Structure | Chemical Name | Physical data |
|---|---|---|---|
| 4-1 | 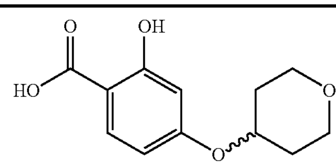 | 2-hydroxy-4-(tetrahydro-pyran-4-yloxy)-benzoic acid | Mp. = 179-181° C. (decomposes); MS (ESI−): 237 (MH−) |
| 4-2 | 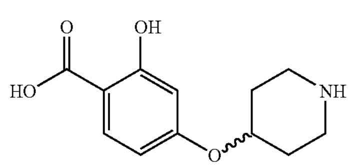 | 2-hydroxy-4-(piperidin-4-yloxy)-benzoic acid | |

The 4-hydroxy group of the compounds in the present invention may be otherwise derivatized e.g. to yield the acylated derivative (see Scheme 5; X=a leaving group e.g. halide).

Scheme 5

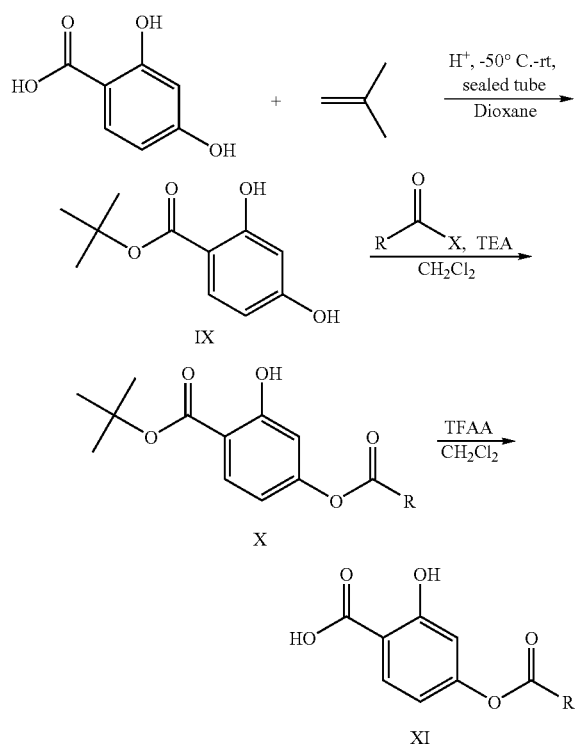

General Method for the Preparation of Compounds of Type XI 2,4-Dihydroxy benzoic acid tert-butyl ester To a solution of 2,4-dihydroxy benzoic acid (3.08 g; 20 mmol) in dioxane (50 mL) was added conc. $H_2SO_4$ (3 mL) and the solution was cooled to −50° C. Isobutene (40 g) was added, the reaction flask sealed and allowed to warm to room temperature. The reaction mixture was stirred overnight, cooled to −30° C. and pH adjusted to 8 using saturated $NaHCO_3$ (aq). The organic phase was Isolated, dried, evaporated to dryness and purified by column chromatography ($SiO_2$-heptane/EtOAc=4:1) to yield 2.3 g (54%). MS (LC-MS): 209 ($MH^-$).

4-(4-Phenyl-benzoyloxy)-2-hydroxy benzoic acid tert-butyl ester

A solution of 2,4-dihydroxy benzoic acid tert-butyl ester (420 mg; 2 mmol), triethylamine (202 mg; 2 mmol) and p-phenyl benzoyl chloride (415 mg; 1.9 mmol) in dry $CH_2Cl_2$ was stirred under argon atmosphere at room temperature overnight after which time $H_2O$ was added. The organic phase was isolated, dried, evaporated to dryness and re-crystallized from 2-propanol to yield 195 mg (25%). MS (LC-MS): 389 ($MH^-$).

4-(4-Phenyl-benzoyloxy)-2-hydroxy benzoic acid (Compound 5-1)

A solution of 4-(4-phenyl-benzoyloxy)-2-hydroxy benzoic acid tert-butyl ester (195 mg; 0.5 mmol) in $CH_2Cl_2$ (5 mL) and trifluoroacetic acid (2.5 mL) was stirred for 2 hours after which time the reaction mixture was evaporated to dryness. The remainder was re-dissolved in $H_2O$/EtOAc and the organic layer isolated, washed with saturated aqueous $NaHCO_3$, dried and evaporated to yield 150 mg (88%) of a white solid. Mp.>275° C.

TABLE 5

| Entry | Chemical Structure | Chemical Name | Physical data |
|---|---|---|---|
| 5-1 | 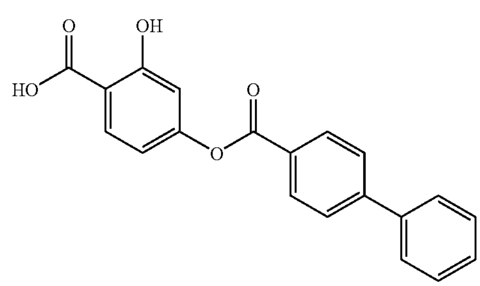 | 4-(4-Phenyl-benzoyloxy)-2-hydroxy benzoic acid | Mp. = >275° C.; |

In order to investigate another embodiment of this invention, 4-amino-salicylic acids were prepared by reacting the 4-amino-salicylic acid with an aldehyde and sodium triethoxyborohydride in dichloroethane at room temperature overnight (see Scheme 6a; X=any substituent). Succeeding acidification and Isolation usually yielded product of satisfactorily purity, although some compounds needed additional column chromatography purification.

Scheme 6a

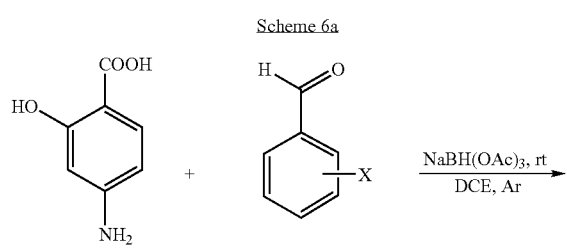

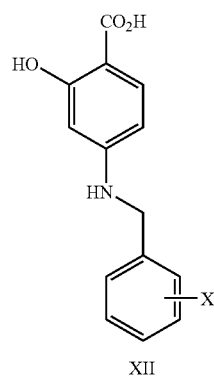

General Method for the Preparation of Compounds of Type XII

2-Hydroxy-4-(3-nitro-benzylamino)-benzoic acid (Compound 6-1)

To a solution of 4-amino salicylic acid (153 mg; 1 mmol) in 1,2-dichloroethane (4 mL) under argon atmosphere was added sodium triacetoxyborohydride (317 mg; 1.5 mmol) and 3-nitrobenzaldehyde (226 mg; 1.5 mmol). The mixture was stirred at room temperature under argon overnight after which time 1 M NaOH (sq.; 5 mL) was added and the two layers separated. The aqueous layer was acidified with 2 M HCl (aq) and the precipitate formed filtered off and dried to yield 160 mg (55%) of a yellowish powder with satisfactorily purity. Mp. 189° C. (decomposes); MS (ESI−): 287 (MH−).

In analogy herewith Compounds 6-2 to 6-14 were synthesized.

In order to prepare compounds as represented in 6-15 it was necessary to protect the carboxylic acid functionality prior to Sonogashira coupling (Scheme 6b)

Scheme 6b

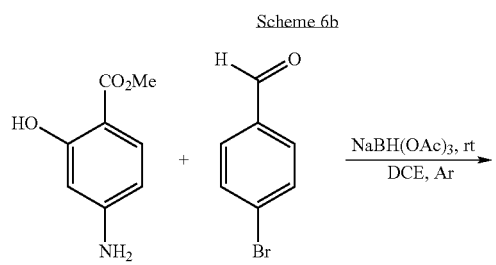

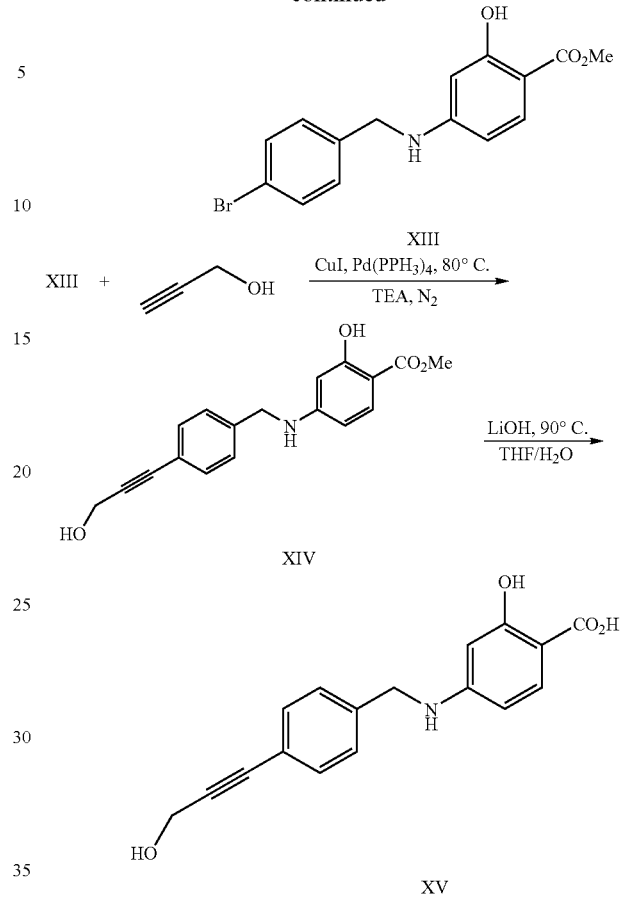

General Method for the Preparation of Compounds of Type XV 4-(4-Bromo-benzylamino)-2-hydroxy-benzoic acid methyl ester To a solution of 4-amino-2-hydroxy benzoic acid methyl ester (836 mg; 5 mmol) and 4-bromobenzaldehyde (926 mg; 5 mmol) in 1 M HOAc in 1,2-dichloroethane (5 mL) was added at once NaBH(OAc)$_3$ (1.49 g; 7 mmol) and the reaction mixture was stirred at room temperature overnight. Water (25 mL) was added and the inhomogeneous mixture was neutralized using solid NaHCO$_3$. The organic layer was isolated, dried, evaporated to dryness and recrystallised from isopropyl ether/dichloromethane/heptane to yield 970 mg (58%) of a yellow solid. NMR and GC-MS in accordance with structure.

2-Hydroxy-4-[4-(3-hydroxy-prop-1-ynyl)benzylamino]-benzoic acid methyl ester

A slurry of 4-(4-Bromo-benzylamino)-2-hydroxy-benzoic acid methyl ester (340 mg; 1 mmol) and propargyl alcohol (90 μL; 1.5 mmol) was heated to 80° C. in N$_2$ purged triethylamine (5 mL). 1,2-Dichloromethane (2 mL) was added and a clear solution appeared after which CuI (4 mg; 2 mol %) and tetrakis (23 mg; 2 mol %) was added. The black solution was stirred at 80° C. for 3 hours, added dichloromethane (20 mL) and 1M HCl (aq.; 30 mL). The organic phase was isolated, dried by filtering through a silicone filter and evaporated onto SiO$_2$. Flash column chromatography (SiO$_2$-PE80-100° C./EtOAc=1:1) yielded 22 mg (7%) pure product.

2-Hydroxy-4-[4-(3-hydroxy-prop-1-ynyl)-benzylamino]-benzoic acid (Compound 6-15)

2-Hydroxy-4-[4-(3-hydroxy-prop-1-ynyl)-benzylamino]-benzoic acid methyl ester (22 mg; 0.07 mmol) was dissolved in THF/H$_2$O (1 mL/0.25 mL) and LiOH was added (17 mg; 0.7 mmol). The reaction mixture was heated to 90° C. for 1 hour. THF was removed by evaporation and EtOAc (3 mL) and H$_2$O (0.5 mL) was added. The organic phase was isolated, dried (Na$_2$SO$_4$), filtered, evaporated to dryness and purified by flash column chromatography (SiO$_2$-PE80-100° C./EtOAc/CH$_3$COOH=1:1:1%) to yield 3.6 mg (17%) of pure product.

TABLE 6

| Entry | Chemical Structure | Chemical Name | Physical data |
|---|---|---|---|
| 6-1 | 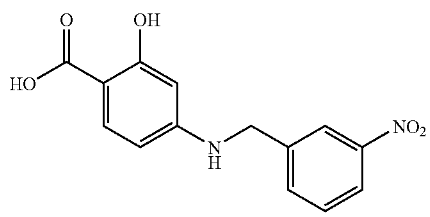 | 2-Hydroxy-4-(3-nitro-benzylamino)-benzoic acid | Mp. = 189° C. (decomposes); MS (ESI−): 287 (MH−) |
| 6-2 | 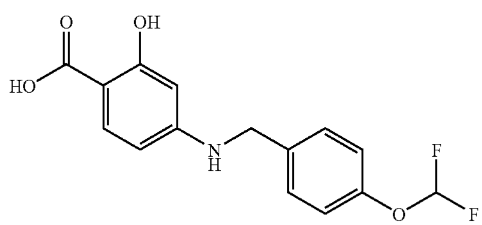 | 4-(4-Difluoromethoxy-benzylamino)-2-hydroxy-benzoic acid | Mp. = 161-162° C.; MS (ESI−): 308 (MH−) |
| 6-3 | 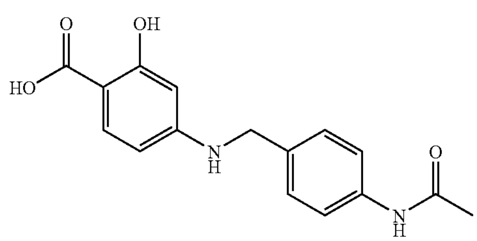 | 4-(4-Acetylamino-benzylamino)-2-hydroxy-benzoic acid | Mp. = 154° C.; MS (ESI−): 299 (MH−) |
| 6-4 | 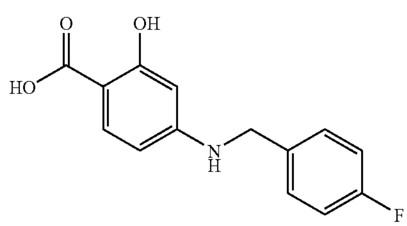 | 4-(4-Fluoro-benzylamino)-2-hydroxy-benzoic acid | Mp. = 175° C. (decomposes); MS (ESI−): 260 (MH−) |
| 6-5 | 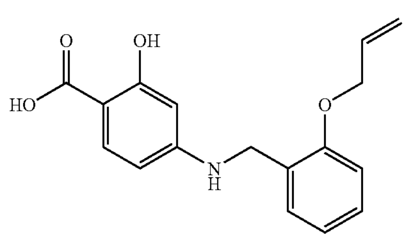 | 4-(2-Allyloxy-benzylamino)-2-hydroxy-benzoic acid | |

TABLE 6-continued

| Entry | Chemical Structure | Chemical Name | Physical data |
|---|---|---|---|
| 6-6 | 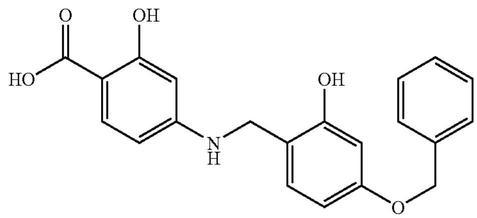 | 4-(2-Hydroxy-4-benzyloxy-benzylamino)-2-hydroxy-benzoic acid | |
| 6-7 | 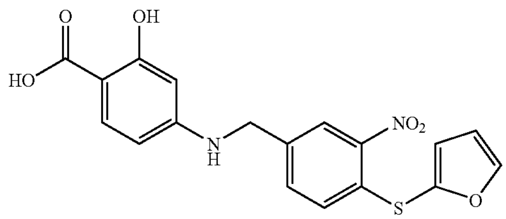 | 4-[4-(Furan-2-yl-sulfanyl)-3-nitro-benzylamino]-2-hydroxy-benzoic acid | MS (ESI−): 399 (MH−) |
| 6-8 | 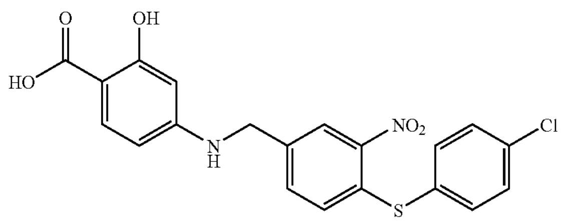 | 4-[4-(4-Chloro-phenylsulfanyl)-3-nitro-benzylamino]-2-hydroxy-benzoic acid | MS (ESI−): 429 (MH−) |
| 6-9 | 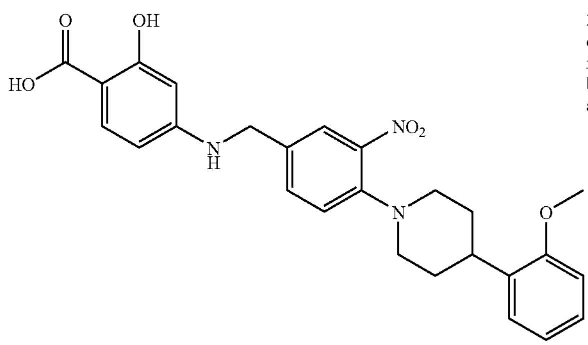 | 2-Hydroxy-4-{4-[4-(2-methoxy-phenyl)-piperidin-1-yl]-3-nitro-benzylamino}-benzoic acid | MS (ESI−): 476 (MH−) |
| 6-10 | 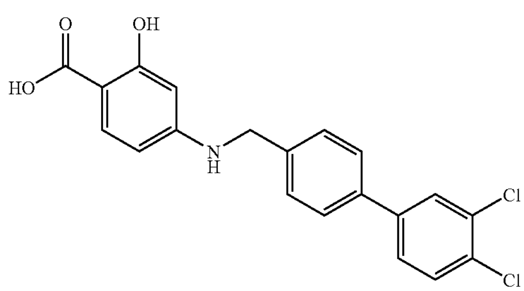 | 4-[(3',4'-Dichloro-biphenyl-4-ylmethyl)-amino]-2-hydroxy-benzoic acid | MS (ESI−): 387 (MH−) |
| 6-11 | 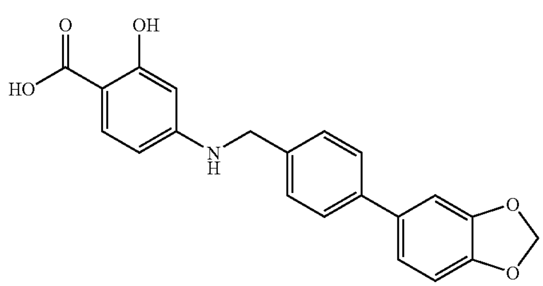 | 4-(4-Benzo[1,3]dioxol-5-yl-benzylamino)-2-hydroxy-benzoic acid | MS (ESI−): 362 (MH−) |

TABLE 6-continued

| Entry | Chemical Structure | Chemical Name | Physical data |
|---|---|---|---|
| 6-12 | 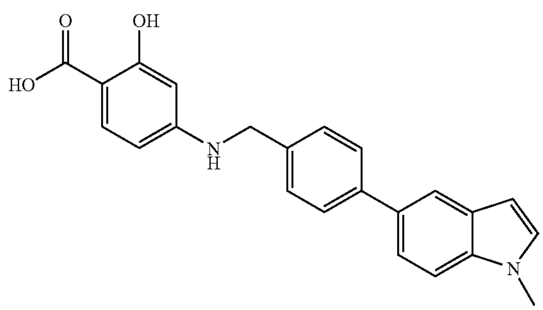 | 2-Hydroxy-4-[4-(1-methyl-1H-indol-5-yl)-benzyl-amino]-benzoic acid | MS (ESI−): 371 (MH−) |
| 6-13 | 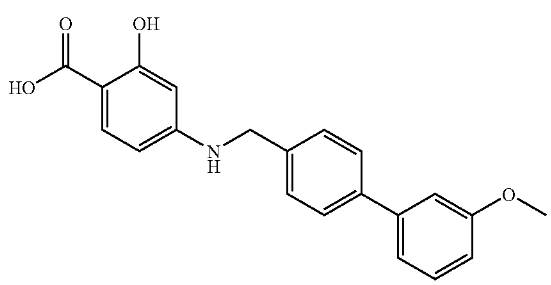 | 2-Hydroxy-4-[(3'-methoxy-biphenyl-4-yl-methyl)-amino]-benzoic acid | MS (ESI−): 348 (MH−) |
| 6-14 | 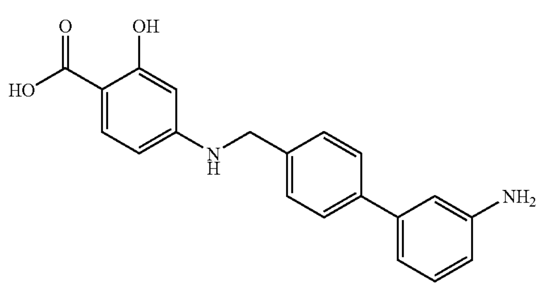 | 4-[(3'-Amino-biphenyl-4-ylmethyl)-amino]-2-hydroxy-benzoic acid | MS (ESI−): 333 (MH−) |
| 6-15 | 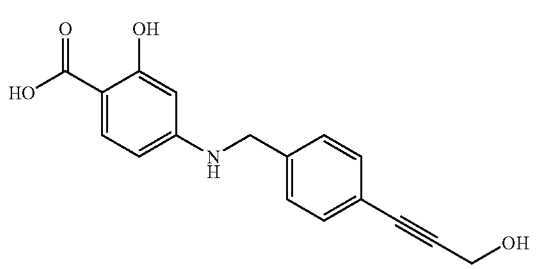 | 2-Hydroxy-4-[4-(3-hydroxy-prop-1-ynyl)-benzyl-amino]-benzoic acid | MS (ESI−): 296 (MH−) |

The 4-amino group of the compounds in the present invention may be otherwise derivatized e.g. to yield the acylated derivative (see Scheme 7; X=a leaving group e.g. halide).

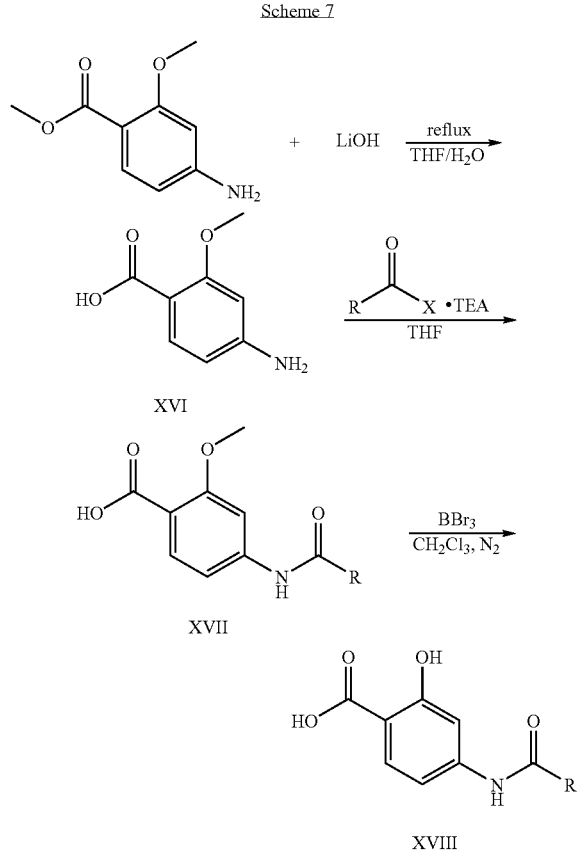

Scheme 7

General Method for the Preparation of Compounds of Type XVIII

4-Amino-2-methoxy benzoic acid

To a solution of 4-amino-2-methoxy benzoic acid methyl ester (5 g; 27 mmol) in THF/H$_2$O (125 mL/25 mL) was added LiOH (4.8 g; 200 mmol) and the slurry was refluxed for 3.5 hours. The reaction mixture was neutralized using 4 M HCl (aq) and the resulting precipitate isolated by filtration and washed with H$_2$O (2×15 mL) to give 3.26 g (80%) of an off-white solid. Mp. 144-146° C.

4-[(Biphenyl-4-carbonylamino]-2-methoxy benzoic acid (Compound 7-1)

To a cooled (5-10° C.) solution of 4-amino-2-methoxy benzoic add (3.25 g; 19.5 mmol) in THF (40 mL) was added diisopropyl ethylamine (3.3 mL; 19 mmol) and 4-biphenyl-carbonylchloride (4.85 g; 22.4 mmol) while the temperature was maintained at 5-10° C. The reaction mixture was stirred for 2 hours and washed with 0.5 M HCl (aq.; 75 mL). The organic phase was isolated, dried by silicone filter filtration, evaporated to dryness and triturated in EtOAc to yield after filtration 3.56 g (52%) of a white solid. Mp. 179-181° C.

4-[(Biphenyl-4-carbonyl)-amino]-2-hydroxy benzoic acid (Compound 7-2)

A solution of 4-[(biphenyl-4-carbonyl)amino]-2-methoxy benzoic acid (2.78 g; 8 mmol) in CHCl$_3$ (175 mL) was cooled until it became cloudy (approx. 40° C.) and BBr$_3$ (1.5 mL; 16 mmol) was added over 2 minutes. The mixture was allowed to warm slightly with stirring for 2 hours after which time another 1.5 mL BBr$_3$ (16 mmol) was added and the reaction mixture was left to warm to room temperature overnight. The resulting slurry was added brine (50 mL) and the organic solvent was removed in vacuo. The resulting solid was Isolated by filtration, washed with H$_2$O, air dried, refluxed in 99% EtOH (100 mL), cooled and filtered to yield 2.2 g (82%) of a white solid. Mp. 266° C. (decomposes).

TABLE 7

| Entry | Chemical Structure | Chemical Name | Physical data |
|---|---|---|---|
| 7-1 | 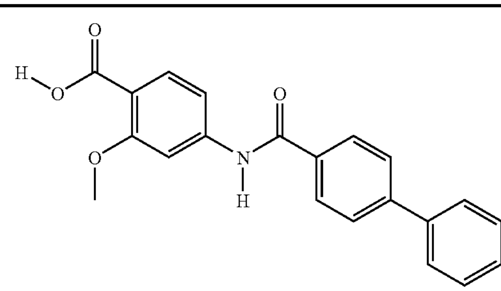 | 4-[(Biphenyl-4-carbonyl)-amino]-2-hydroxy benzoic acid | Mp. = 179-181° C. |
| 7-2 | 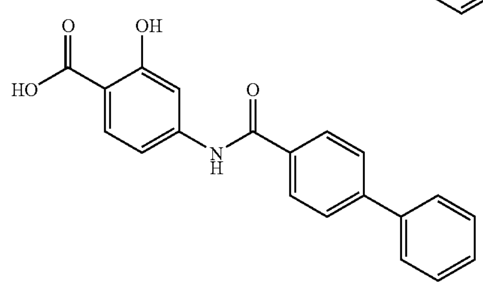 | 4-[(Biphenyl-4-carbonyl)-amino]-2-hydroxy benzoic acid | Mp. = 266° C. (decomposes) |

In order to investigate yet another embodiment of this invention, 4-aryloxy salicylic acids were prepared by the reaction of methyl 4-hydroxy salicylic acid ester in a nucleophilic displacement reaction and succeeding de-sterification in alkaline solution (see Scheme 8; X=typically F, NO$_2$, Cl, etc; EWG=electron attracting group). Likewise 4-arylaminoyl salicylic acids were prepared by reaction with unprotected 4-amino-salicylic acid.

The compounds can be further derivatized, e.g. on the free hydroxy before de-esterification, by known methods for those skilled in the art (see Scheme 8 and Table B).

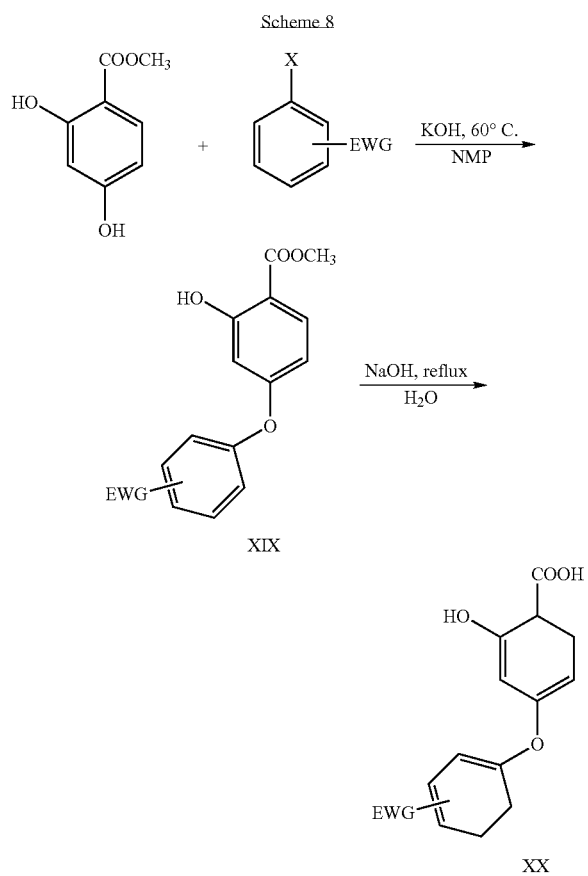

General Method for the Preparation of Compounds of Type XX

Methyl-2-hydroxy-4-(4-nitro-phenoxy)-benzoic acid ester

Solid KOH (0.84 g; 15 mmol) was added to a solution of methyl-4-hydroxy sallcylic acid (2.52 g; 15 mmol) in N-methylpyrrolidon (30 mL) and dissolved by heating (50-100° C.). The resulting orange solution was cooled to room temperature, added 4-fluoronitrobenzene (2.11 g; 15 mmol) and reheated to 60° C. for 19 hours. The reaction mixture was poured onto H$_2$O (150 mL), extracted with EtOAc (2×100 mL), washed with aqueous NaCl, dried (silicone-filter) and chromatographied (SiO$_2$-PE80-100° C./EtOAc=10:1) to yield 1.35 g (31%) of a pure white solid.

2-Hydroxy-4-(4-nitro-phenoxy)-benzoic acid

A slurry of methyl 2-hydroxy-4-(4-nitro-phenoxy)-benzoic acid ester (1.26 g; 4.4 mmol) in 4 M NaOH (aq.; 100 mL) was refluxed for 1 hour and then placed on an ice/water bath. The alkaline slurry was acidified under stirring with 12 M HCl (aq), filtered, washed H$_2$O and dried in vacuo to yield 950 mg (78%) of a pure white solid. Mp. 195-197° C.; MS (ESI−): 274 (MH$^-$).

2-Hydroxy-4-(4-amino-phenoxy)-benzoic acid (Compound 8-2)

A slurry of 2-hydroxy-4-(4-nitro-phenoxy)benzoic acid (950 mg; 3.5 mmol) in 99% EtOH (30 mL) and THF (0.5 mL) was added 5% Pd/C (100 mg) and stirred under H$_2$ atmosphere (1 atm.) for 25 minutes. The black solution was filtered through celite and evaporated to dryness yielding 300 mg (35%) of a brown powder. Mp. 187-188° C.; MS (ESI+): 246 (MH$^+$).

2-Hydroxy-4-(4-ethoxyoxalylamino)-phenoxy benzoic acid (Compound 8-3)

To a slurry of 2-hydroxy-4-(4-amino-phenoxy)-benzoic acid (24.5 mg; 0.1 mmol) in CH$_2$Cl$_2$ (2 mL) was added diisopropylethylamine (35 μL; 0.2 mmol) and ethyl oxalylchloride (17 μL; 0.15 mmol). The resulting solution was stirred at room temperature for 1 hour and evaporated to dryness. The yellow oil was flash chromatographied (SiO$_2$—CH$_2$Cl$_2$/MeOH=20:1) to yield 10 mg of a pure white solid.

Additional compounds were synthesized in a similar manner (see Table 8).

TABLE 8

| Entry | Chemical Structure | Chemical Name | Physical data |
|---|---|---|---|
| 8-1 | 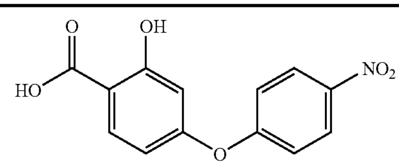 | 2-Hydroxy-4-(4-nitro-phenoxy)-benzoic acid | Mp. = 195-197° C.; MS (ESI−): 274 (MH$^-$) |
| 8-2 | 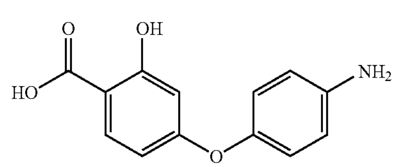 | 4-(4-Amino-phenoxy)-2-hydroxy-benzoic acid | Mp. = 187-188° C.; MS (ESI+): 246 (MH$^+$) |

TABLE 8-continued

| Entry | Chemical Structure | Chemical Name | Physical data |
|---|---|---|---|
| 8-3 | 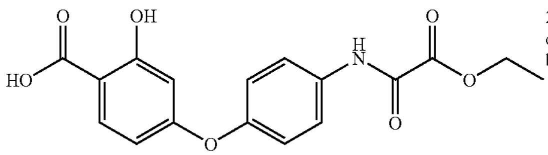 | 2-Hydroxy-4-(4-ethoxyoxalyl-amino)-phenoxy benzoic acid | |
| 8-4 | 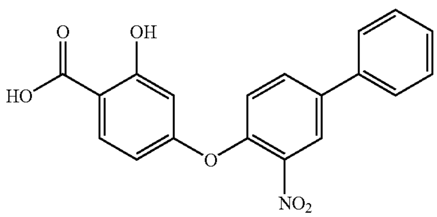 | 2-Hydroxy-4-(3-nitro-biphenyl-4-yloxy)-benzoic acid | Mp. = >200 °C. (decomposes); MS (ESI−): 250 (MH−) |
| 8-5 | 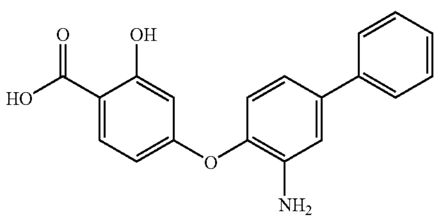 | 4-(3-Amino-biphenyl-4-yl-oxy)-2-hydroxy-benzoic acid | MS (ESI−): 320 (MH−) |
| 8-6 | 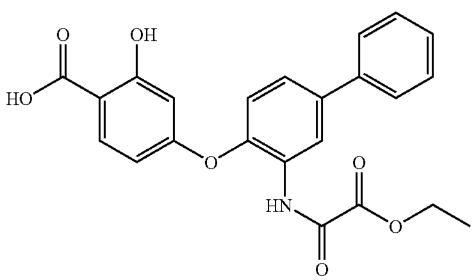 | 4-[3-(Ethoxyoxazolyl-amino)-biphenyl-4-yl-oxy]-2-hydroxy-benzoic acid | MS (ESI−): 420 (MH−) |
| 8-7 | 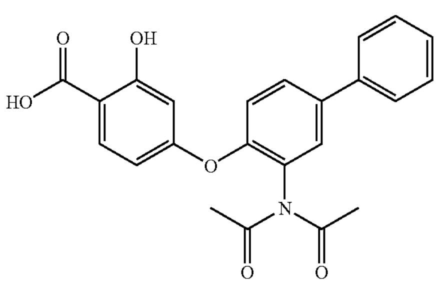 | 4-(3-Diacetylamino-biphenyl-4-yloxy)-2-hydroxy-benzoic acid | MS (ESI−): 404 (MH−) |
| 8-8 | 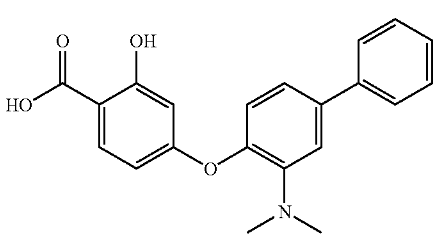 | 4-(3-Dimethylamino-biphenyl-4-yloxy)-2-hydroxy-benzoic acid | MS (ESI−): 448 (MH−) |

TABLE 8-continued

| Entry | Chemical Structure | Chemical Name | Physical data |
|---|---|---|---|
| 8-9 | 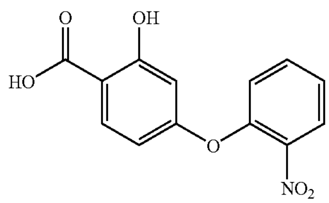 | 2-Hydroxy-4-(2-nitro-phenoxy)-benzoic acid | MS (ESI−): 274 (MH⁻) |
| 8-10 | 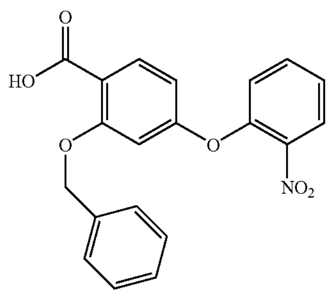 | 2-Benzyloxy-4-(2-nitro-phenoxy)-benzoic acid | MS (ESI−): 264 (MH⁻) |
| 8-11 | 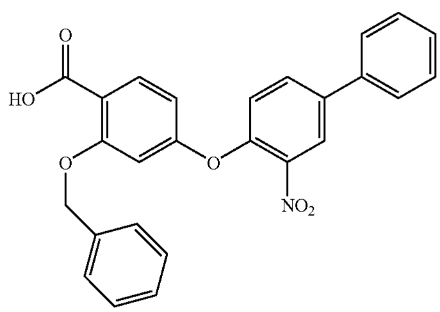 | 2-Benzyloxy-4-(3-nitro-biphenyl-4-yl-oxy)-benzoic acid | MS (ESI−): 444 (MH⁻) |
| 8-12 | 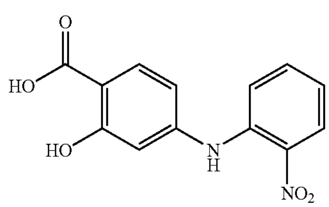 | 2-Hydroxy-4-(2-nitro-phenylamino)-benzoic acid | Mp. = 190° C.; (decomposes) MS (ESI+): 273 (MH⁺) |

In order to investigate yet another embodiment of this invention, 4-alkoxy-2-hydroxy anilides were prepared by the acylation or sulfonylation of 2,4-dimethoxy aniline, succeeding demethylation and final alkylation using e.g. a halide (see Scheme 9; X=leaving group).

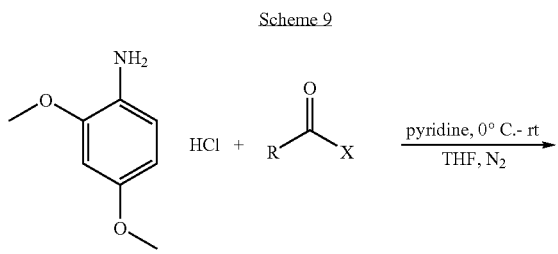

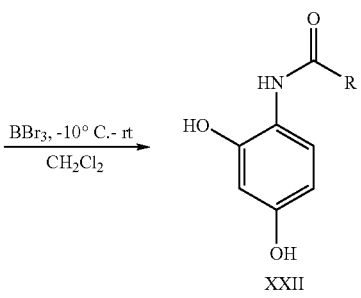

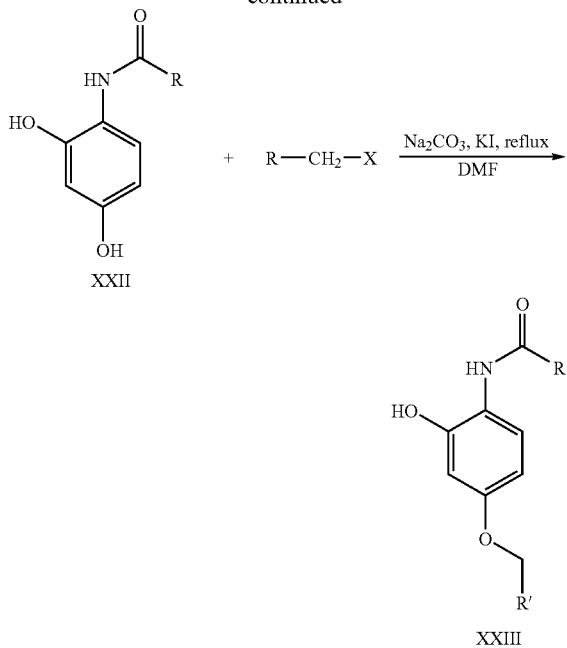

General Method for the Preparation of Compounds of Type XXIII

N-(2,4-Dimethoxyphenyl)-2,2,2-trifluoro-acetamide

A slurry of 2,4-dimethoxyaniline hydrochloride (1.90 g; 10 mmol) in THF (20 mL) was added pyridine (1.6 mL; 20 mmol) and cooled on an ice/water bath (0-5° C.). The mixture was then added trifluoroacetic anhydride (1.56 mL; 11 mmol) and left to slowly warm to room temperature overnight. The reaction mixture was evaporated to approx. 5 mL, added diethylether (40 mL) and H$_2$O (30 mL). The organic layer was isolated, dried (MgSO$_4$), filtered and evaporated to dryness to yield the desired compound in quantitative yield.

N-(2,4-Dihydroxyphenyl)-2,2,2-trifluoro-acetamide

To a solution of N-(2,4-dimethoxy phenyl)-2,2,2-trifluoro-acetamide (2.50 g; 10 mmol) in CH$_2$Cl$_2$ (20 mL) cooled to −10° C. was added 1 M BBr$_3$ (CH$_2$Cl$_2$; 24 mL; 24 mmol) under N$_2$ atmosphere. The mixture was allowed to warm to room temperature over 2 hours and poured onto H$_2$O (150 mL). Saturated aqueous NaHCO$_3$ (100 mL) and diethylether (100 mL) was added to dissolve any precipitated material. The organic layer was Isolated, washed with H$_2$O (50 mL), dried (MgSO$_4$), filtered and the eluate evaporated to dryness to yield 1.85 g (83%) of the desired compound as a greyish solid.

N-(2-Hydroxy-4-octyloxy-phenyl)-2,2,2-trifluoro-acetamide (Compound 1)

To a solution of N-(2,4-dihydroxy phenyl)-2,2,2-trifluoro-acetamide (0.44 g; 2 mmol) in DMF (4 mL) was added K$_2$CO$_3$ and 1-bromooctane (0.37 mL; 2.1 mmol). The slurry was stirred for 2 days at room temperature, poured onto 0.1 M HCl (aq.; 50 mL) and then extracted with diethylether (30 mL). The organic phase was dried (MgSO$_4$), filtered and the eluate evaporated to leave 550 mg of black solid which was purified by chromatography (SiO2; PE80-100° C./EtOAc=4:1) to leave 100 mg (15%) of a pure white solid. Mp. 114-116° C.; MS (GC-MS; CI): 334 (MH$^+$).

Similar compound were synthesized in an analogous manner (see Table 9).

TABLE 9

| Entry | Chemical Structure | Chemical Name | Physical data |
|---|---|---|---|
| 9-1 | 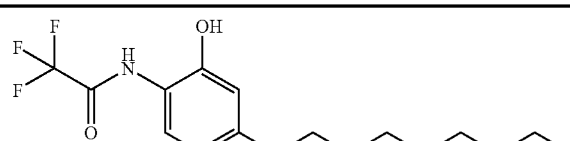 | 2,2,2-trifluoro-N-(2-hydroxy-4-octyloxy-phenyl)-acetamide | Mp. = 114-116° C.; MS (GC-MS; CI): 334 (MH$^+$) |
| 9-2 | 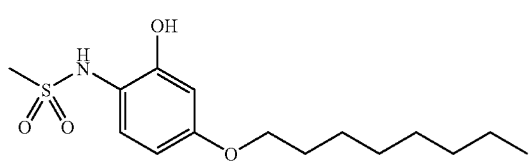 | N-(2-hydroxy-4-octyloxy-phenyl)-methanesulfonamide | Mp. = 98-101° C.; MS (GC-MS; CI): 316 (MH$^+$) |
| 9-3 | 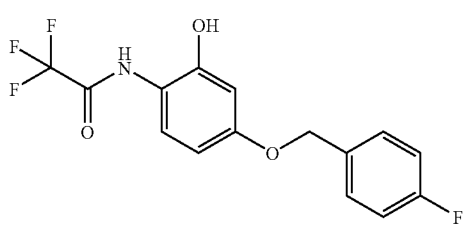 | 2,2,2-trifluoro-N-[4-(4-fluorobenzyloxy)-2-hydroxyphenyl]-acetamide | Mp. = 143-145° C.; MS (EI+); 329 (M$^+$) |

4-alkoxy catechols may be prepared from 3,4-methylendioxyphenol by initial alkylation and then ether cleavage (see Scheme 10).

4-alkyl-salicylic acids can be prepared from m-methoxy benzaldehyde by a initial Grignard reaction. Reduction of the styrene formed, bromination of the aromatic nucleus and succeeding Grignard reaction yields the 4-alkoxy-O-methyl benzoic acid. Ether cleavage yields the desired 4-alkyl salicylic acids (see Scheme 11).

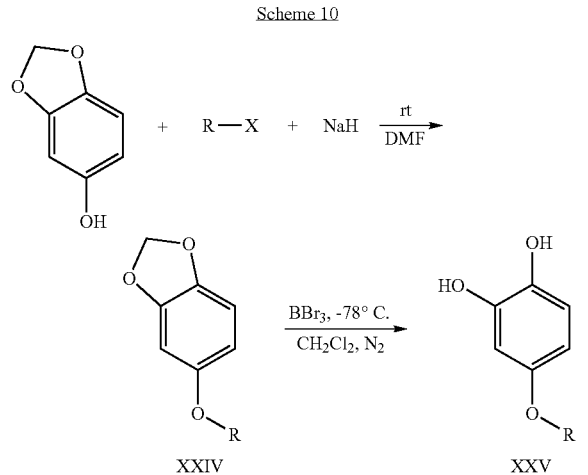

Scheme 10

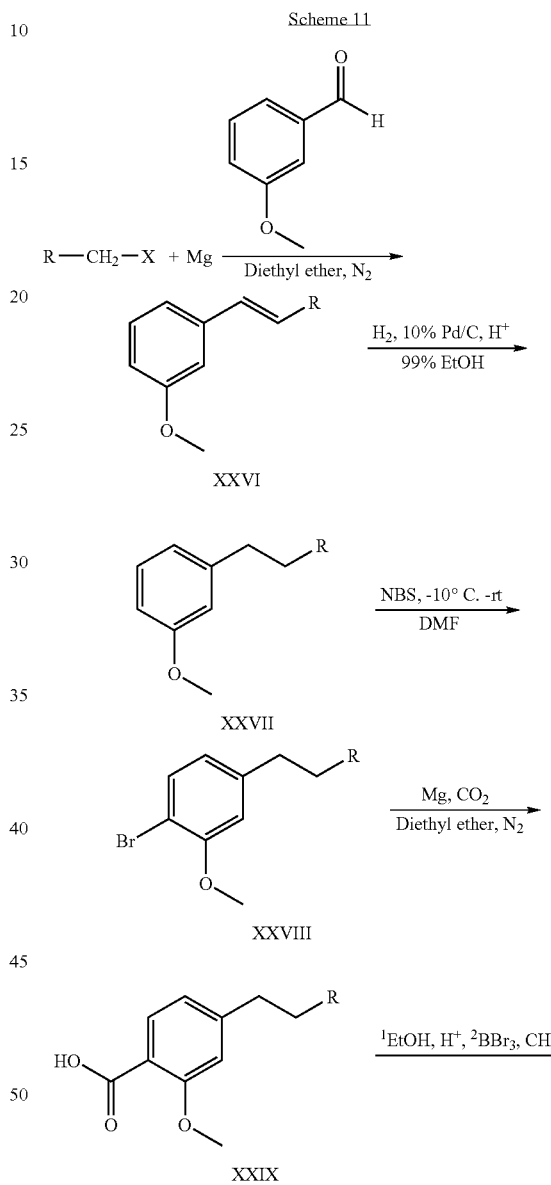

Scheme 11

General Method for the Preparation of Compounds of Type XXV

4-Octyloxy-benzo[1,3]dioxole

A solution of sesamol (6.9 g; 50 mmol) in DMF (100 mL) under $N_2$ was cooled to 0° C. and sodium hydride (60% w/w dispersion; 2.3 g; 60 mmol) carefully added. The slurry was allowed to warm to room temperature over 1 hour after which time 1-bromooctane (13 mL; 75 mmol) was added. The mixture was stirred for 5 days, poured onto $H_2O$ and extracted with diethylether (2×). The combined organic fractions were dried ($MgSO_4$), filtered and evaporated in vacuo to yield 12.8 g (quantitative yield) of a white solid. Mp. 120° C.

4-Octyloxy-benzene-1,2-diol (Compound 10-1)

A solution of 4-octyloxy-benzo[1,3]dioxole (2.5 g; 10 mmol) in $CH_2Cl_2$ (25 mL) was cooled to −78° C. and 1 M $BBr_3$ ($CH_2Cl_2$; 22 mL; 22 mmol) was added drop wise over 1 hour. The viscous reaction mixture was stirred for another 1.5 hours, poured onto $H_2O$ (100 g) and quickly extracted with EtOAc (3×). The combined organic fractions were dried ($MgSO_4$), filtered and evaporated at room temperature. The crude product was triturated with EtOAc, filtered and evaporated to give 2.49 g of a solid which was further purified by column chromatography ($SiO_2$; EtOAc/PE80-100° C.=1:4) to yield 1.29 g (54%) pure product which turns dark in air/light. Mp. 108-115° C.

TABLE 10

| Entry | Chemical Structure | Chemical Name | Physical data |
|---|---|---|---|
| 10-1 | (structure) | 4-Octyloxy-benzene-1,2-diol | Mp. = 108-115° C. (decomposes) |

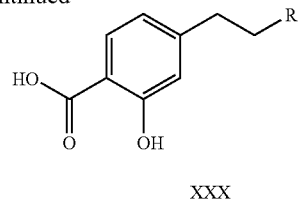

XXX

General Method for the Preparation of Compounds of Type XXX

1-Methoxy-3-non-1-enyl benzene

To dry diethyl ether (50 mL) containing Mg turnings (1.22 g; 50 mmol) under $N_2$ was added 1-bromononane (8.6 mL; 50 mmol) at a rate sufficient to maintain slow reflux. The reaction mixture was stirred for 45 minutes after the end of addition, cooled on an ice/water bath and 3-methoxy benzaldehyde (6.1 mL; 50 mmol) was then added drop wise. The reaction mixture was allowed to warm to room temperature overnight, added saturated aqueous $NH_4Cl$ (50 mL) and then 4 M HCl (aq.; 10 mL). The organic phase was isolated, dried ($MgSO_4$), filtered and purified by column chromatography ($SiO_2$; EtOAc/PE80-100° C.=1:10) to yield 7.4 g (64%) pure product.

1-Methoxy-3-nonyl benzene

A solution of 1-methoxy-3-non-1-enyl benzene (7.4 g 32 mmol) in 99% EtOH (50 mL) was added 6 M HCl (aq.; 0.5 mL) and stirred with 10% Pd/C under $H_2$-atmosphere (1 atm) to give 7.5 g (quantitative yield) of the desired product, after filtration through Celite and evaporation to dryness of the eluate.

1-Bromo-2-methoxy-nonyl benzene

A solution of 1-methoxy-3-nonyl benzene (7.5 g; 32 mmol) in DMF (60 mL) was cooled to −10° C. and N-bromosuccinimide (5.42 g; 30 mmol) was added under stirring over 30 minutes. The MeOH/ice bath was removed after 1 hour and the reaction mixture was left overnight with stirring. The reaction mixture was poured onto $H_2O$ (100 mL) and 10 M NaOH (aq) was added. The alkaline slurry was extracted with EtOAc (2×) and the combined organic fractions washed with 1 M NaOH (aq.; 2×), dried ($MgSO_4$), filtered and evaporated to dryness. The crude product was further purified by column chromatography ($SiO_2$; EtOAc/PE80-100° C.=0: 1→1:20) to yield 9.8 g (quantitative) of product with satisfactory purity.

2-Methoxy-4-nonyl benzoic acid

To dry diethyl ether (10 mL) containing Mg turnings (0.24 g; 10 mmol) under $N_2$ was added 1-bromo-2-methoxy-nonyl benzene (3.1 g; 10 mmol). 1,2-Dioiodoethane was added to initiate the reaction. Solid dry Ice (excess) was added after stirring for 1 hour and after additional stirring for 1 hour was added sat. $NH_4Cl$ (aq.; 20 mL) and then 4 M HCl (aq.; 2 mL). The organic phase was isolated, dried ($MgSO_4$), filtered and purified by column chromatography ($SiO_2$; EtOAc/PE80-100° C.=1:5) to yield 600 mg (20%) pure product.

4-Nonyl salicylic acid (Compound 11-1)

A solution of 2-methoxy-4-nonyl benzoic acid (600 mg; 2.15 mmol) was refluxed overnight in 6 M HCl [50% (w/w) EtOH/$H_2O$; 35 mL). The reaction mixture was extracted with EtOAc (3×) dried ($MgSO_4$), filtered and evaporated to dryness. The crude ester was dissolved in $CH_2Cl_2$ (10 mL), cooled to −10° C. and then added 1 M $BBr_3$ ($CH_2Cl_2$; 10 mL; 10 mmol). The reaction mixture was allowed to warm to room temperature overnight and then poured onto $H_2O$. Succeeding extraction with EtOAc, drying ($MgSO_4$), filtering, evaporation to dryness and column chromatography ($SiO_2$) yielded 130 mg (23%) product. Mp. 94-97° C.

TABLE 11

| Entry | Chemical Structure | Chemical Name | Physical data |
|---|---|---|---|
| 11-1 | 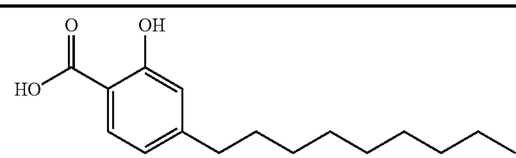 | 4-Nonyl salicylic acid | Mp. = 94-97° C. |

In another embodiment of this invention, the carboxylic acid group may be substituted with other polar groups, which in addition may be derivatized by conventional methods. As described earlier the initial reaction is that of a e.g. alkyl halide and a 4-substituted resorcinol (see Scheme 12; Y=polar substituent).

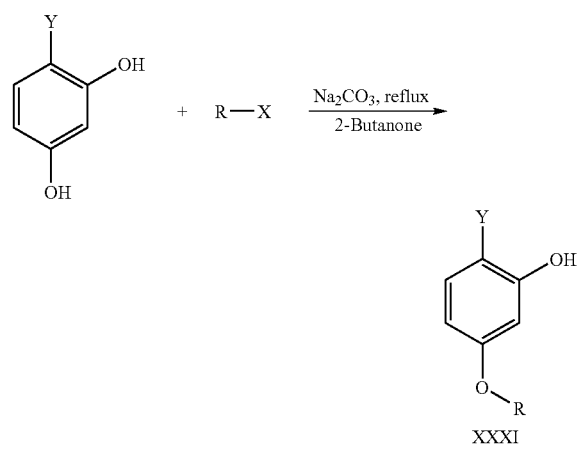

Scheme 12

XXXI

In the following the preparation of examples of such compounds are described.

1-(2-Hydroxy-4-octyloxy-phenyl)-ethanone (Compound 12-1)

A slurry of 2,4-dihydroxy actophenone (3.8 g; 25 mmol) and KHCO$_3$ (2.75 g; 27.5 mmol) in DMF (50 mL) was stirred at 50° C. for 1 hour and then added 1-bromooctane (4.75 mL; 27.5 mmol). The reaction mixture was stirred at 50-60° C. for 7 days, poured onto H$_2$O (100 mL) and the aqueous phase extracted with diethyl ether (3×). The combined organic fractions was dried (MgSO$_4$), filtered, evaporated to dryness and purified by column chromatography (SiO$_2$; EtOAc/PE80-100° C.=1:10) to yield 4.39 g (66%) as yellow oil. MS (direct; Cl): 265 (MH$^+$).

2-Hydroxy-4-octyloxy-benzaldehyde oxime (Compound 12-3)

To a solution of 2-hydroxy-4-octyloxy-benzaldehyde (3.64 g; 14.5 mmol) in abs. EtOH (30 mL) was added hydroxylamine hydrochloride [50% H$_2$O (w/w)] and the slurry was stirred for 2 hours. The reaction mixture was evaporated to dryness and the resulting solid triturated in H$_2$O (20 mL) and EtOAc/diethylether (20 mL+10 mL) to give 1.8 g (47%) as a white solid. MS (direct; EI): 265 (M).

2-Hydroxy-4-octyloxy-benzamide (Compound 12-4)

A slurry of methyl-4-octyloxy salicylic acid ester (8.11 g; 29 mmol) in conc. aqueous NH$_3$ (25% w/w; 100 mL) was heated to 110° C. in a sealed reactor under stirring for 11 hours and cooled. The precipitate was dissolved by addition of brine (100 mL) and EtOAc (100 mL). The organic phase was isolated and the aqueous extracted twice with EtOAc. The combined organic fractions were dried (Na$_2$SO$_4$), filtered, evaporated to dryness and the remainder purified by column chromatography (SiO$_2$; CH$_2$Cl$_2$/MeOH=30:1-20:1) to yield 5.7 g (74%) product as a white solid with satisfactorily purity). Mp. 123-124° C. MS (GC-MS; Cl): 266 (MH$^+$).

2-Hydroxy-4-octyloxy-benzonitrile (Compound 12-5)

A solution of 2-hydroxy-4-octyloxy-benzamide (5.21 g; 19.7 mmol) and dibutyltinoxide (3.65 g; 14.6 mmol) was refluxed in toluene (60 mL) for 12 days. The reaction mixture was evaporated to dryness on SiO$_2$ and purified by column chromatography (SiO$_2$; EtOAc/PE80-100° C.=1:4) to yield 700 mg (14%) product as yellow crystals. Mp. 69-71° C. MS (Direct; Cl): 248 (MH$^+$).

5-Octyloxy-2-(1H-tetrazol-5-yl)-phenol (Compound 12-6)

A slurry of 2-hydroxyoctyloxy-benzonitrile (247 mg; 1 mmol), sodium azide (195 mg; 3 mmol), triethylamine hydrochloride (411 mg; 3 mmol) was refluxed in toluene (5 mL) under N$_2$ for 4 hours after which time the reaction mixture was poured onto H$_2$O 0 (10 mL). The precipitate formed was dissolved by addition of 10 M NaOH (aq) and EtOAc. The organic phase was isolated and extracted with 4 M NaOH (aq). The combined aqueous phases was acidified using 12 M HCl (aq) and the precipitate formed isolated by filtration to yield 240 mg (82%) as a purple solid after drying. Mp. 142-146° C. MS (Direct; Cl): 291 (MH$^+$).

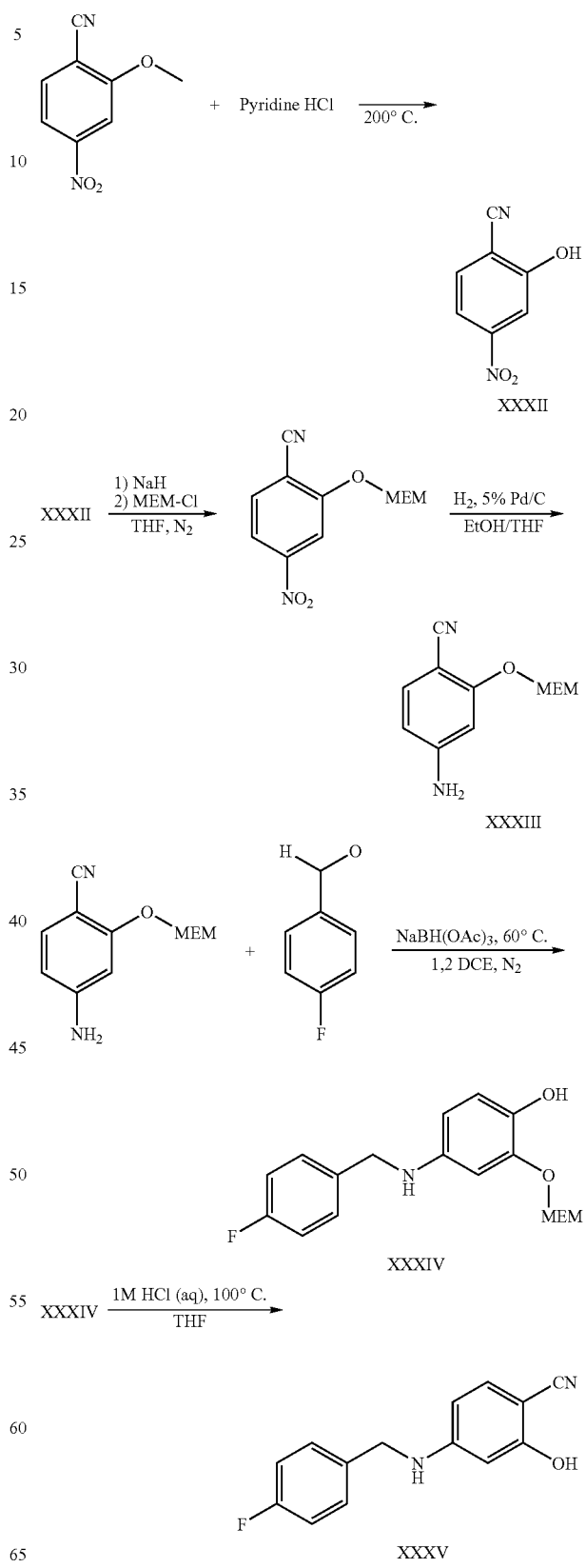

Scheme 13

General Method for the Preparation of Compounds of Type XXXV

2-Hydroxy-4-nitro-benzonitrile

Pyridine hydrochloride (100 g; 0.87 mol) and 2-methoxy-4-nitro-benzonitrile (17 g; ca 96 mmol) was heated to 200° C. for 2 hours, cooled to room temperature and carefully added H$_2$O and EtOAc. The slurry was stirred until all solid dissolved. The organic layer was isolated, washed twice with H$_2$O, brine then dried, filtered and evaporated to dryness to yield 15 g (95%) pure product 2-(2-Methoxy-ethoxymethoxy)-4-nitro-benzonitrile To a solution of 2-hydroxy nitro-benzonitrile (1.5 g; 9 mmol) in THF (75 mL) under argon was carefully added NaH (60% dispersion in mineral oil; 400 mg; 10 mmol) and then methoxyethoxymethyl chloride (2.5 g; 19.8 mmol). The reaction mixture was stirred for 2 h at room temperature, carefully added H$_2$O and then EtOAc. The organic phase was isolated, dried, filtered and evaporated to dryness to give a quantitative yield of product.

4-Amino-2-(2-methoxy-ethoxymethoxy)-benzonitrile

To a solution of 2-(2-Methoxy-ethoxymethoxy)-4-nitro-benzonitrile (2.35 g; 9 mmol) in EtOH/THF (25 mL/1 mL) was added a catalytic amount of 5% Pd/C. The reaction mixture was stirred under H$_2$ atmosphere for 18 hours, filtered through kiselguhr evaporated to dryness and purified by column chromatography (SiO$_2$—MeOH/CH$_2$Cl$_2$=0:1 to 5:95) to yield after evaporation 1.8 g (88%).

4-(4-Fluoro-benzylamino)-2-(2-methoxy-ethoxymethoxy)-benzonitrile

To a solution of 4-amino-2-(2-methoxy-ethoxymethoxy)-benzonitrile (666 mg; 3 mmol) in 1,2-dichloroethan (15 mL) was added 4-fluorobenzaldehyd (496 mmol; 4 mmol) and carefully sodium triacetoxyborohydride (933 mg; 4.4 mmol). The mixture was stirred at 60° C. for 6 hours. The reaction mixture was added 1 M NaOH (aq.), dried by filtering through a silicone filter, evaporated onto SiO$_2$ and purified by column chromatography (SiO$_2$-heptane/EtOAc=2:1) to yield 700 mg pure product.

4-(4-Fluoro-benzylamino)-2-hydroxy-benzonitrile (Compound 12-7)

To a solution of 4-(4-fluoro-benzylamino)-2-(2-methoxy-ethoxymethoxy)-benzonitrile (15 mg; 0.05 mmol) in THF (1 mL) was added 4 M HCl (aq.; 0.5 mL). The mixture was refluxed for 2 h, cooled and the precipitate filtered off. Purification by flash column chromatography (SiO$_2$—MeOH/CH$_2$Cl$_2$=0:1 to 5:95) yielded 2.5 mg pure product.

To those skilled in the art it is known that nitrile compounds such as Compound 12-7 may be further derivatized by conventional methods to yield compounds such as those represented by compound 12-8 through 12-11.

TABLE 12

| Entry | Chemical Structure | Chemical Name | Physical data |
|---|---|---|---|
| 12-1 | 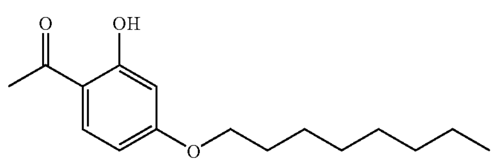 | 1-(2-hydroxy-4-octyloxy-phenyl)-ethanone | MS (direct; Cl): 265 (MH$^+$) |
| 12-2 | 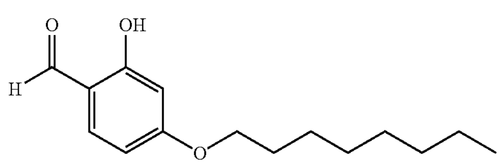 | 2-hydroxy-4-octyloxy-benzaldehyde | MS (direct; Cl): 251 (MH$^+$) |
| 12-3 | 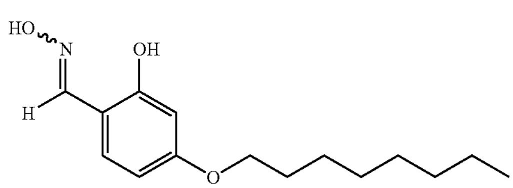 | 2-hydroxy-4-octyloxy-benzaldehyde oxime | MS (direct; El): 265 (M) |
| 12-4 | 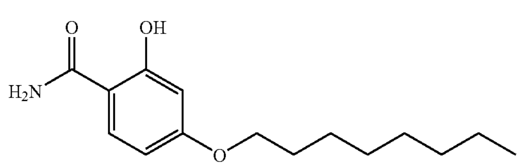 | 2-hydroxy-4-octyloxy-benzamide | Mp. = 123-124° C. MS (GC-MS; Cl): 266 (MH$^+$) |

TABLE 12-continued

| Entry | Chemical Structure | Chemical Name | Physical data |
| --- | --- | --- | --- |
| 12-5 | 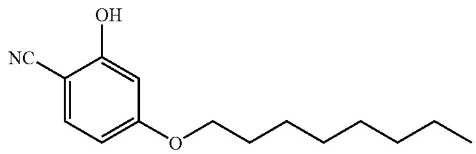 | 2-hydroxy-4-octyloxy-benzonitrile | Mp. = 69-71° C.<br>MS (Direct; Cl):<br>248 (MH$^+$) |
| 12-6 | 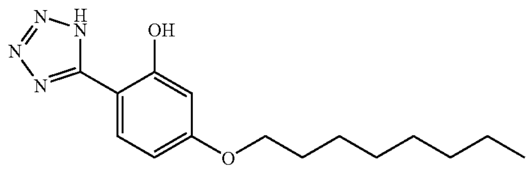 | 5-Octyloxy-2-(1H-tetrazol-5-yl)-phenol | Mp. = 142-146° C.<br>MS (Direct; Cl):<br>291 (MH$^+$) |
| 12-7 | 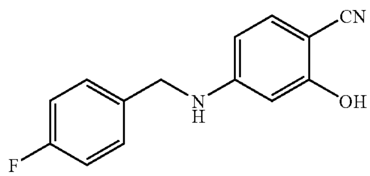 | 4-(4-Fluoro-benzylamino)-2-hydroxy-benzonitrile | |
| 12-8 | 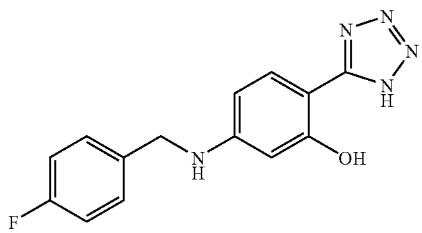 | 5-(4-Fluoro-benzylamino)-2-(1H-tetrazol-5-yl)-phenol | |
| 12-9 | 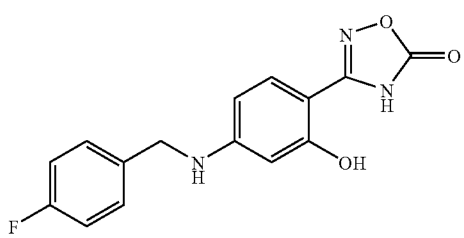 | 3-[4-(4-Fluoro-benzylamino)-2-hydroxy-phenyl]-4H-[1,2,4]oxadiazol-5-one | |
| 12-10 | 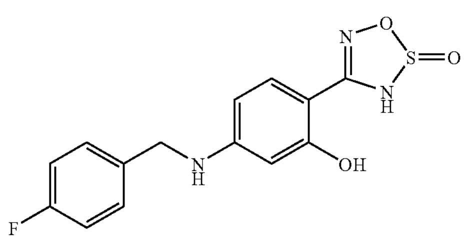 | 5-(4-Fluoro-benzylamino)-2-(2-oxo-2,3-dihydro-2$\lambda^4$-[1,2,3,5]oxathiadiazol-4-yl)-phenol | |
| 12-11 | 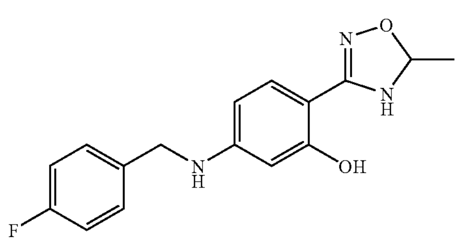 | 5-(4-Fluoro-benzylamino)-2-(5-methyl-4,5-dihydro-[1,2,4]oxadiazol-3-yl)-phenol | |

TABLE 12-continued

| Entry | Chemical Structure | Chemical Name | Physical data |
|---|---|---|---|
| 12-12 | 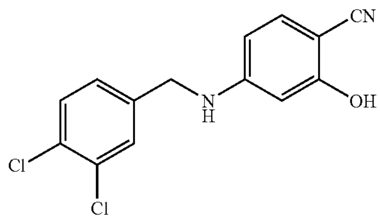 | 4-(3,4-Dichloro-benzylamino)-2-hydroxy-benzonitrile | |
| 12-13 | 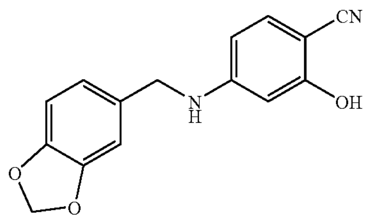 | 4-[(Benzo[1,3]dioxol-5-yl-methyl)-amino]-2-hydroxy-benzonitrile | |
| 12-14 | 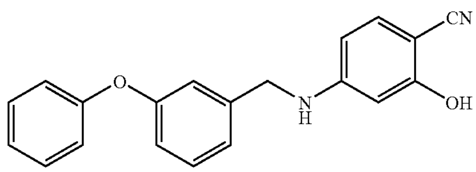 | 2-Hydroxy-4-(3-phenoxy-benzylamino)-benzonitrile | |
| 12-15 | 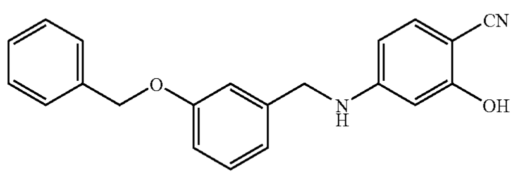 | 4-(3-Benzyloxy-benzylamino)-2-hydroxy-benzonitrile | |
| 12-16 | 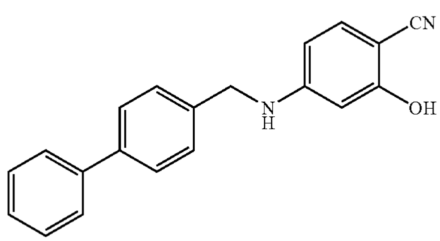 | 4-[(Biphenyl-4-yl-methyl)-amino]-2-hydroxy-benzonitrile | Mp. = 196-197° C.<br>MS (ESI–): 299 (MH⁻) |

Example 2

Biological Activity

KCNQ channels constitute a subfamily of the voltage-dependent potassium (K) channels. Five members of this family have been cloned (1-5) and they have been heterologously expressed in various homo- and heteromeric combinations. The ionic current through the channels is recorded in the whole-cell mode of the patch-clamp technique. The KCNQ currents are activated by a depolarising voltage step and it is investigated whether the test compound change the amount of basal current. Compounds that induce an increase in the voltage-activated current are called activators and the effect obtained by these activators is described as a percentage increase in baseline current at a given concentration.

In a first experiment, two compounds, Compounds 3-11 and 3-17, representative of the compounds of the invention, were subjected to electrophysiological investigations.

A HEK293 cell line stably expressing the human KCNQ4 channel was obtained as described by Søgaard et al. [Søgaard R, Ljungstrøm T. Pedersen K A, Olesen S-P, Jensen B S: KCNQ4 channels expressed in mammalian cells: Functional characteristics and pharmacology; *Am. J. Phys.* 2000 280 C859-C866].

Experiments are carried out on a patch-clamp set-up. Cells plated on cover slips (Ø3.5 mm) are placed in a 15 µl perfusion chamber (flow rate ~1 ml/min) mounted on an IMT-2 or IX-70 microscope equipped with Nomarski or Hoffmann optics. The microscope is placed on a vibration-free table in a grounded Faraday cage. All experiments are performed at room temperature (20-22° C.). The EPC-9 patch-clamp amplifier (HEKA-electronics, Lambrecht, Germany) is connected to a Macintosh computer via an ITC16 interface. Data are stored directly on the hard disk and analysed using IGOR software (Wavemetrics, Lake Oswego, USA).

The whole-cell configuration of the patch clamp technique is applied. In short: The Up of a borosilicate pipette (resistance 24 MΩ) is gently (remote control system) placed on the cell membrane. Light suction results in a giga seal (pipette resistance increases to more than 1 GΩ) and the cell membrane is then ruptured by more powerful suction. Cell capacitance is electronically compensated and the resistance between the pipette and the cell interior (the series resistance, Rs) is measured and compensated for. Usually the cell capacitance ranges from 5 to 20 pF (depending on cell size) and the series resistance is in the range 3 to 6 MΩ. Rs- as well as capacitance compensation are updated during the experiments (before each stimulus). All experiments with drifting Rs-values are discharged. Leak-subtractions are not performed but the leak is estimated by a hyper-polarisation voltage step.

The extracellular (bath) solution contains 144 mM NaCl, 2 mM CaCl$_2$, 1 mM MgCl$_2$, 10 mM HEPES (pH=7.4). Test compounds are usually dissolved as 1000 times concentrated stock solutions in DMSO and then diluted in the extracellular solution. The intracellular (pipette) solution has the following composition 144 mM KCl, 5.37 mM CaCl$_2$, 1.75 mM MgCl$_2$, 4 mM NaATP, 0.4 mM NaGTP, 10 mM EGTA, and 10 mM HEPES (pH=7.2). By use of the program EqCal the concentration of free Ca$^{2+}$ have been calculated to 100 nM, the free Mg$^{2+}$ is 1 mM, and MgATP is 1.45 mM.

After establishment of the whole-cell configuration a voltage protocol is applied to the cell every 5 seconds from a holding potential of –90 mV. The current is zero at the holding potential, since this is the K reversal potential with the Ringer's employed. Further, most channels are closed at this negative potential. By a brief step to –150 the degree of leak current is estimated and experiments are discontinued if the current at this potential is larger than 200 pA. The subsequent depolarisation to –30 mV activates the channels, and this potential is kept for 1000 ms in order to obtain a steady-state activation. The potential is finally stepped to –60 mV. Just after the whole-cell configuration has been obtained the currents activated are very small, but they increases as the pipette solution dilutes the cytosol. A relatively stable baseline current is obtained within a period of 100-300 seconds and compounds are then added by changing to an extracellular solution containing the compound to be tested.

The amount of current activated at the end of the step to –30 mV is analysed as a function of time, exported and calculated using the IGOR software. Compounds are defined as activators or inhibitors, respectively, if they induce an increase or a decrease, respectively, in current.

In a first experiment, Compounds 3-11 and 3-17 were subjected to this assay and found to be activators of the KCNQ channel, and the results of this determination are presented in Table 13 below.

For channel activators the baseline current is defined as 100%, and an increase in current is expressed relative to this, i.e. an increase from 1 nA to 1.2 nA is reported as 120%.

TABLE 13

Electrophysiological Determination

| Test compound | $I_K$ (%) |
|---|---|
| Compound 3-11 | 115 |
| Compound 3-17 | 115 |

The invention claimed is:
1. A compound represented by Formula I

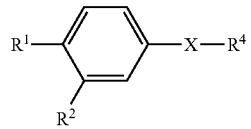

any of its enantiomers or any mixture of its enantiomers, or a prodrug, or a pharmaceutically-acceptable addition salt thereof, wherein
R$^1$ represents —CN;
R$^2$ represents halo, haloalkyl, hydroxyl or alkoxy;
X represents, NR" or NR"CH$_2$ (read in the stated direction); wherein
R" represents hydrogen;
R$^4$ represents aryl-alkyl, which is substituted one or more times with substituents selected from the group consisting of halo, or methylenedioxy; or
R$^4$ represents a group of formula -Z'-L"-Z"; wherein
Z' and Z", independently of one another, represent an aryl group, which aryl may be optionally substituted one or more times with halo; and
L" represents a single (covalent) bond, or a linker selected from O or OCH$_2$, with the proviso that when X represents NR", then R$^4$ represents aryl-alkyl and when X represents NR"CH$_2$, then R$^4$ represents a group of formula -Z'-L"-Z".

2. The compound of claim 1, wherein R$^4$ represents benzyl which is substituted one or two times with halo or one time with methylenedioxy.

3. The compound of claim 2, wherein R$^4$ represents 4-fluoro-benzyl, 3,4-dichloro-benzyl or benzo[1,3]dioxol-5-ylmethyl.

4. The compound of claim 3, which is
4-(4-Fluoro-benzylamino)-2-hydroxy-benzonitrile
4-(3,4-Dichloro-benzylamino)-2-hydroxy-benzonitrile or
4-[(Benzo[1,3]dioxol-5-ylmethyl)-amino]-2-hydroxy-benzonitrile;
or a pharmaceutically-acceptable addition salt thereof.

5. The compound of claim 1 wherein R$^4$ represents a group of formula -Z'-L"-Z"; wherein
Z' represents phenyl, or phen-4-yl;
which phenyl may optionally be substituted one or two times with halo; and
Z" represent phenyl;
which may optionally be substituted one or two times with halo; and
L" represents a single (covalent) bond, or a linker selected from alkyl, O, or OCH$_2$.

6. The compound of claim 5, wherein R$^4$ represents 3-phenoxy-phenyl, 3-benzyloxy-phenyl, or biphenyl-4-yl.

7. The compound of claim 6, which is
2-Hydroxy-4-(3-phenoxy-benzylamino)-benzonitrile;
4-(3-Benzyloxy-benzylamino)-2-hydroxy-benzonitrile;
or
4-[(Biphenyl-4-ylmethyl)-amino]-2-hydroxy-benzonitrile;
or a pharmaceutically-acceptable addition salt thereof.

8. A pharmaceutical composition comprising a therapeutically effective amount of a compound of claim 1, or a pharmaceutically-acceptable addition salt thereof.

* * * * *